US009340532B2

(12) United States Patent
Kirkpatrick et al.

(10) Patent No.: US 9,340,532 B2
(45) Date of Patent: May 17, 2016

(54) METHODS AND COMPOSITIONS FOR INHIBITING CNKSR1

(71) Applicant: PHUSIS THERAPEUTICS, INC., San Diego, CA (US)

(72) Inventors: D. Lynn Kirkpatrick, San Diego, CA (US); Martin Indarte, San Diego, CA (US); Nathan T. Ihle, San Diego, CA (US)

(73) Assignee: Phusis Therapeutics, Inc., San Diego, CA (US)

( * ) Notice: Subject to any disclaimer, the term of this patent is extended or adjusted under 35 U.S.C. 154(b) by 0 days.

(21) Appl. No.: 14/649,349

(22) PCT Filed: Dec. 16, 2013

(86) PCT No.: PCT/US2013/075505
§ 371 (c)(1),
(2) Date: Jun. 3, 2015

(87) PCT Pub. No.: WO2014/093988
PCT Pub. Date: Jun. 19, 2014

(65) Prior Publication Data
US 2015/0307482 A1    Oct. 29, 2015

Related U.S. Application Data

(60) Provisional application No. 61/737,658, filed on Dec. 14, 2012.

(51) Int. Cl.
C07D 409/14    (2006.01)
C07D 417/14    (2006.01)
C07D 409/12    (2006.01)
A61K 31/502    (2006.01)

(52) U.S. Cl.
CPC ............ *C07D 409/14* (2013.01); *C07D 409/12* (2013.01); *C07D 417/14* (2013.01)

(58) Field of Classification Search
CPC .. C07D 409/14; C07D 417/14; C07D 409/12; A61K 31/502
USPC ........................................................ 544/327
See application file for complete search history.

(56) References Cited

U.S. PATENT DOCUMENTS

| 3,821,222 | A | 6/1974 | Moore |
| 4,017,489 | A | 4/1977 | Lawrence |
| 4,251,528 | A | 2/1981 | Brittain et al. |
| 4,694,015 | A | 9/1987 | Sebille et al. |
| 4,939,140 | A | 7/1990 | Larson et al. |
| 6,066,311 | A | 5/2000 | Cheetham et al. |
| 6,924,284 | B2 * | 8/2005 | Beaton ............... A61K 41/0038 514/234.5 |
| 2004/0092524 | A1 | 5/2004 | Perez et al. |
| 2004/0102360 | A1 | 5/2004 | Barnett et al. |
| 2007/0213378 | A1 | 9/2007 | Thomas et al. |
| 2007/0293516 | A1 | 12/2007 | Knight et al. |
| 2011/0144066 | A1 | 6/2011 | Mahadevan et al. |
| 2012/0189670 | A1 | 7/2012 | Kirkpatrick et al. |
| 2013/0184317 | A1 | 7/2013 | Mahadevan et al. |
| 2015/0126563 | A1 | 5/2015 | Mahadevan et al. |

FOREIGN PATENT DOCUMENTS

| CA | 775563 A | 1/1968 |
| DE | 2556011 A1 | 6/1977 |
| DE | 3443225 A1 | 6/1985 |
| EP | 2428504 A1 | 3/2012 |
| EP | 2477625 | 7/2012 |
| GB | 828963 A | 2/1960 |
| WO | WO 90/15600 A2 | 12/1990 |
| WO | WO 00/18376 A1 | 4/2000 |
| WO | WO 02/083064 A2 | 10/2002 |
| WO | WO 03/076436 A | 9/2003 |
| WO | WO 03/084473 A2 | 10/2003 |
| WO | WO 2005/090461 A2 | 9/2004 |
| WO | WO 2005/000862 A | 1/2005 |
| WO | WO 2005/005421 A1 | 1/2005 |
| WO | WO 2005/097758 A | 10/2005 |
| WO | WO 2006/046914 A1 | 5/2006 |
| WO | WO 2007/039173 A1 | 4/2007 |
| WO | WO 2008/083158 A2 | 7/2008 |
| WO | WO 2009/129267 A2 | 10/2009 |
| WO | WO 2011/032169 A2 | 3/2011 |
| WO | WO 2014/093988 A2 | 6/2014 |

OTHER PUBLICATIONS

PubChem Compound (http://pubchem.ncbi.nlm.nih.gov/) CID 24283805 (Feb. 29, 2008).
PubChem Compound (http://pubchem.ncbi.nlm.nih.gov/) CID 3800302 (Feb. 29, 2008).
PubChem Compound (http://pubchem.ncbi.nlm.nih.gov/) CID 3268165 (Feb. 29, 2008).
Anwar et al. "Reactions of some 5-aryl-2-thiono-1, 3, 4-thiadiazoles" Jan. 1, 1981, *Romanian Journal of Chemistry* 26(8):1127-1134.
Carpten et al. "A Transforming Mutation in the Pleckstrin Homology Domain of AKT1 in Cancer" Jul. 26, 2007, *Nature* 448(7152):439-444.
Castillo et al. "Preferential Inhibition of Akt and Killing of Akt-dependent Cancer Cells by Rationally Designed Phosphatidylinositol Ether Lipid Analogues" Apr. 15, 2004, *Cancer Res.* 64(8):2782-92.
Catley et al. "Alkyl Phospholipids Perifosine Induces Myeloid Hyperplasia in a Murin Myeloma Model" Jul. 2007, *Exp. Hematol.* 35(7):1038-1046 (abstract).
Chemical Abstract Database compound (CAS RN 1022250-16-3) entering date May 25, 2008.
Chemical Abstract Database compound (CAS RN 1022557-01-2) entering date May 26, 2008.

(Continued)

*Primary Examiner* — Yevegeny Valenrod
(74) *Attorney, Agent, or Firm* — Pepper Hamilton LLP

(57) ABSTRACT

Embodiments include compositions and methods of inhibiting CNKSR1 and methods of identifying inhibitors of CNKSR1.

19 Claims, 19 Drawing Sheets

(56) References Cited

OTHER PUBLICATIONS

Chemical Abstract Database: compound (CAS RN 477482-99-8), entering date Dec. 12, 2002.
Chemical Abstract Database: compound (CAS RN 477483-04-8), entering date Dec. 12, 2002.
Chemical Abstract Database: compound (CAS RN 919458-54-1), entering date Feb. 6, 2007.
Database Pubchem (Online) NCBI: Sep. 11, 2005 Database accession No. CID3800302.
Database Pubchem (Online) NCBI: Sep. 7, 2005 Database accession No. CID3268165.
Database Pubchem (Online) NCBI; Feb. 29, 2008 Database accession No. CID24283805.
Dhe-Paganon et al. "Crystal Structure of the Pleckstrin Homology-phosphotyrosine Binding (PH-PTB) Targeting Region of Insulin Receptor Substrate 1" Jul. 20, 1999, *PNAS USA* 96(15):8378-8383.
Du-Cuny et al. "Computational modeling of novel inhibitors targteting the Akt pleckstrin homology domain" Aug. 19, 2009, *Bioorganic & Medicinal Chemistry* 17(19):6983-6992.
European Search Report and Written Opinion dated Feb. 2, 2012 for EP 11181871.
Feldman et al. "Novel Small Molecule Inhibitors of 3'-phosphoinositide-dependent Kinsase1 (PDK-1)" Sep. 30, 2004, *Eur. J. Cancer Supp.* 2(249):77.
Fengl "Enteric Coating" Oct. 22, 2002, *Enerex.ca* 5 pages.
Gills et al. "Spectrum of Activity and Molecular Correlates of Response to Phosphatidylinositol Ether Lipid Analogues, Novel Lipid-based Inhibitors of Akt" Mar. 2006, *Mol. Cancer Ther.* 5(3):713-722.
Giranda et al. "Novel ATP-competitive AKT Inhibitors Slow the Progression of Tumors in vivo" Sep. 30, 2004, *Eur. J. Cancer Supp.* 2(246):76-77.
Humphreys et al. "Toxicity and antileukemic effectiveness of pyridine derivatives and 1,3,4-thiadiazole derivatives in mice. Relationship to nicotinamide antagonism" 1962, *Cancer Res.* 22:483-550.
International Search Report and Written Opinion dated Jun. 3, 2014 for PCT/US2013/75505.
International Search Report and Written Opinion dated May 26, 2011 for PCT/US2010/048813.
International Search Report and Written Opinion dated Oct. 19, 2009 for PCT/US2009/040575.
International Search Report dated Dec. 15, 2009 for PCT/US2009/040575.
Kim et al. "Targeting the Phosphatidylinositol-3 Kinase/Akt Pathway for the Treatment of Cancer" Dec. 2005, *Curr. Opin. Investig. Drugs* 6(12):1250-1258.
Komander et al. "Structural Insights into the Regulation of Pdk1 by Phosphoinositides and Inositol Phosphates" 2004, *EMBO J.* 23(20):3918-3928.
Kumar et al. "AKT Crystal Structure and AKT-specific Inhibitors" Nov. 2005, *Oncogene* 24(50):7493-7501.
Li "Recent Progress in the Discovery of Akt Inhibitors as Anticancer Agents" 2007, *Expert Opin. Ther. Patents* 17:1077-1130.
Mahadevan et al. "Discovery of a novel class of AKT pleckstrin homology domain inhibitors" Sep. 2008, *Mol. Cancer Ther.* 7(9):2621-2632.
Mahieu et al. "Synthesis of new thiosulfonates and disulfides from sulfonyl chlorides and thiols" Jan. 1, 1986, *Synthetic Communications* 16(13):1709-1722.
Meuillet et al. "In Vivo Molecular Pharmacology and Antitumor Activity of the Targeted Akt Inhibitor PX-316" 2004, *Oncol. Res.* 14(10):513-527 (abstract).
Meuillet et al. "Specific Inhibition of the Akt2 Pleckstrin Homology domain by D-3-deoxy-phosphatidyl-myo-inositol Analogues" Apr. 2003, *Mol. Cancer. Ther.* 2(4):390-399.
Miyahara et al. "Antitumor activity of 2-Acylamino-1,3,4-thiadiazoles and related compounds" 1982, *Chem. Pharm. Bul.* 30(12):4402-4406.
Moses, et al., "In vitro and in vivo activity of novel small-molecule inhibitors targeting the pleckstrin homology domain of protein kinase B/AKT" Jun. 15, 2009, *Cancer Research* 69(12):5073-5081.
Office Action issued in Australian Application No. 2009236256, mailed May 2, 2013.
Office Action issued in Australian Application No. 2009236256, mailed Jun. 11, 2014.
Office Action issued in U.S. Appl. No. 12/937,898, mailed Jun. 18, 2012.
Office Action issued in U.S. Appl. No. 12/937,898, mailed Aug. 30, 2012.
Office Action issued in U.S. Appl. No. 13/789,209 dated Jun. 25, 2014.
Office Action issued in European Application No. 11181871.2, mailed Jul. 10, 2013.
Office Action issued in European Application No. 11181871.2, mailed Sep. 25, 2014.
Peng et al. "Dwarfism, Impaired Skin Development, Skeletal Muscle Atrophy, Delayed Bone Development, and Impeded Adipogenesis in Mice Lacking Akt1 and Akt2" Jun. 1, 2003, *Genes Dev.* 17(11):1352-1365.
Powell et al. "Bile Acid Hydrophobicity is Correlated with Induction of Apoptosis and/or Growth Arrest in HCT116 Cells" 2001, *Biochem J.* 356:481-486.
Runge et al. "Uber einige unsymmetrishce heterocyclische Disulfide, II" Jul. 1, 1963, *J. Fuer Praktische Chemie* 21(1-2):39-49 (cited in German/ no translation available).
Sassiver et al. "2-Sulfanilamido-5-methoxy-,1,3,4-thiadiazole and related compounds" 1966, *J. Med. Chem.* 9(4):541-545.
Stein et al. "Discovery and structure of activity relationships of sulfonamide ETA-selective antagonists" 1995, *J. Med. Chem.* 38:1344-1354.
Supplementary European Search Report and Written Opinion dated Sep. 17, 2012 for EP 10816289.
Thomas et al. "High-resolution Structure of Pleckstrin Homology Domain of Protein Kinase B/akt Bound to Phosphatidylinositol (3,4,5)-trisphosphate" Jul. 2002, *Curr. Biol.* 12(14):1256-1262.

* cited by examiner

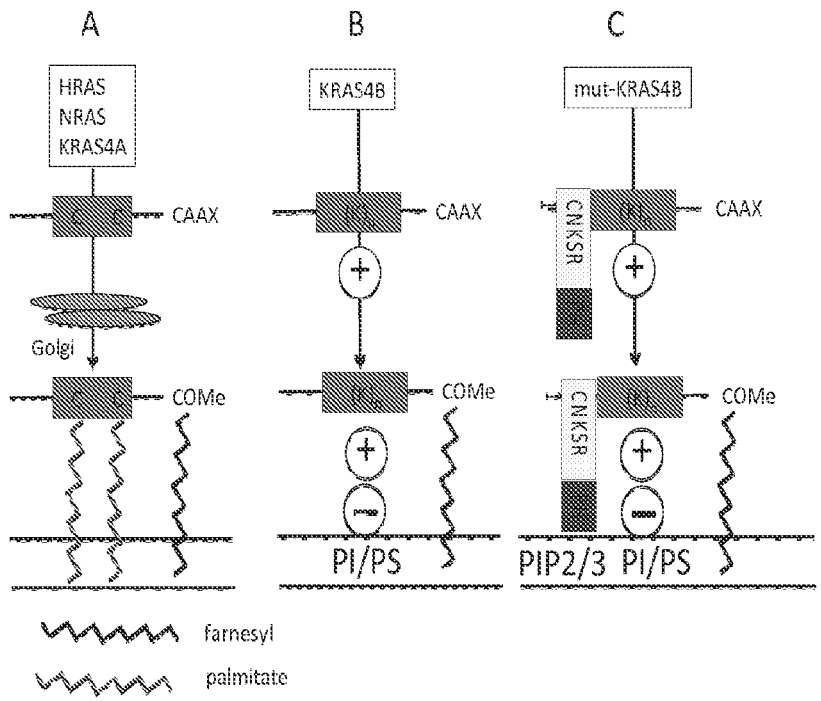

Figure 1
Role of CNKSR1 in mut-KRAS signaling. RAS undergo C-terminal CAAX farnesylation (or geranylgeranylation) followed by Rce1/ICMT processing. A, HRAS, NRAS and KRAS4A undergo hypervariable (hv) domain palmitoylation and Golgi processing leading to their lipid raft membrane localization. B, KRAS4B does not undergo Golgi processing and its polybasic hv domain binds to membrane PI and PS in specific lipid rafts. C, We propose that mut-KRAS but not wt-KRAS associates in a unique signaling nanocluster with the PH domain containing protein CNKSR1 to bind to PIP2/3 rich membrane lipid rafts necessary for mut-KRAS signaling

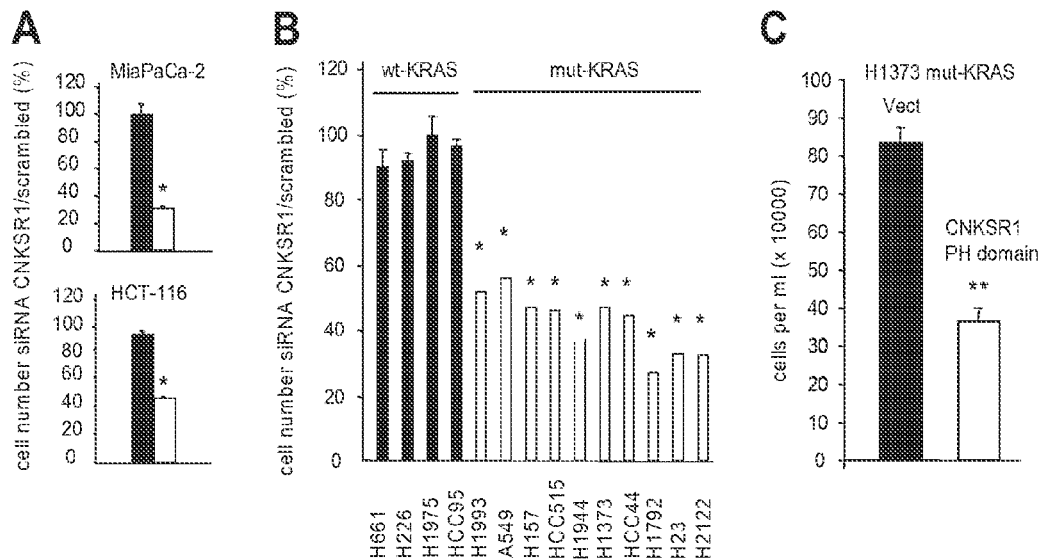

Figure 2
CNKSR1 as a target for inhibition of mut-KRAS cell growth. A, Validation using CNKSR1 siRNA in MiaPaCa-2 and HCT-116 isogenic wt- and mut-KRAS cell lines. Filled boxes are wt-KRAS and open boxes mut-KRAS. Values are means of 3 determinations and bars are SE. * p<0.05. B, CNKSR1 siRNA in a panel of NSCLC cell lines with filled boxes showing wt-KRAS, and open boxes mut-KRAS cells. Values are expressed as a % relative to scrambled siRNA control. Bars are SE. * p<0.05 compared to scrambled siRNA. C Growth of H1373 mut-KRAS NSCLC cell line stably transfected with (closed boxes) vector alone or with (open boxes) a CNSKR1 PH domain construct that acts as a dominant negative inhibitor of cell growth. Bars are SE. ** p<0.01.

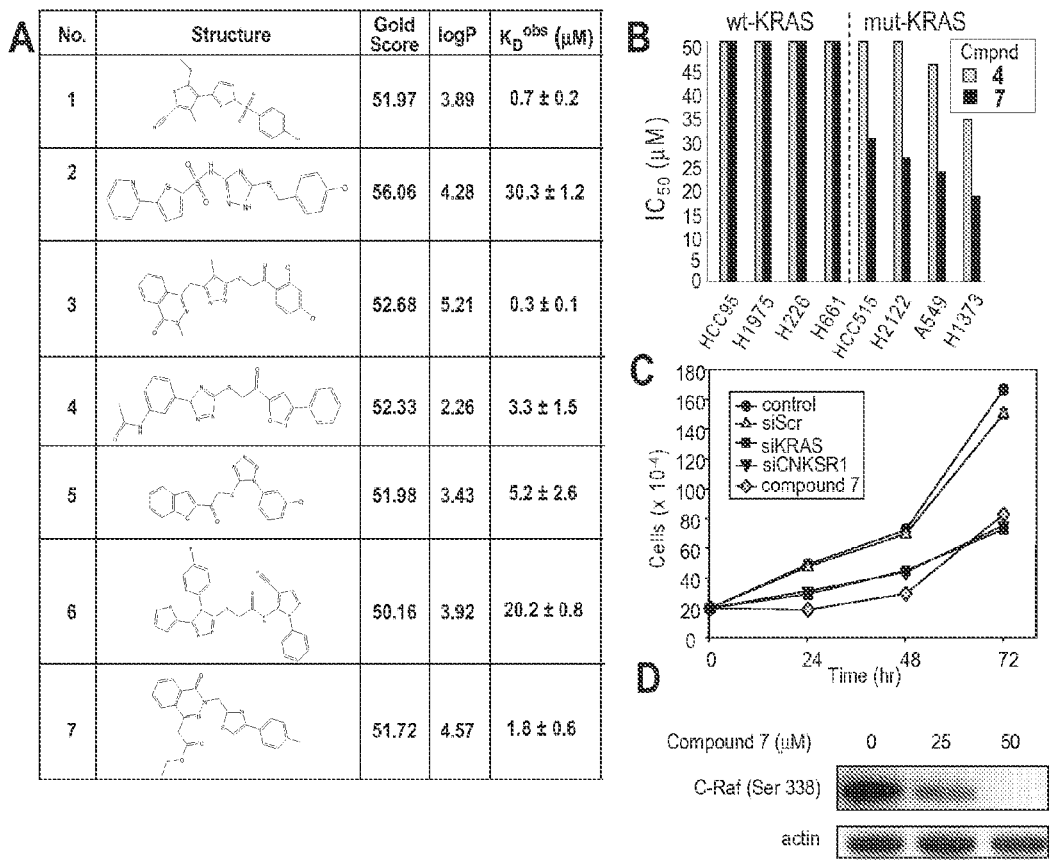

Figure 3
Inhibitors of the PH domain of CNKSR1 inhibit mut-KRAS but not wt-KRAS cell growth. A, Inhibitors of the CNKSR1 PH domain predicted by the PHuDock® program bind to the expressed PH domain of CNKSR1 with Kd measured by plasmon spin resonance binding to the expressed PH domain of CNKSR1. Also shown is the calculated Gold score and log P. B: Cell growth inhibition in wild type and mut-KRAS NSCLC cells by compounds 4 and 7 expressed as $IC_{50}$s; C, Inhibition of A-549 NSCLC cell growth by siRNA to KRAS, CNKSR1 and 25 µM compnd 7. D, Western blot showing the inhibition of down stream KRAS signaling measured by p-C-RAF($Ser^{338}$), by compound 7.

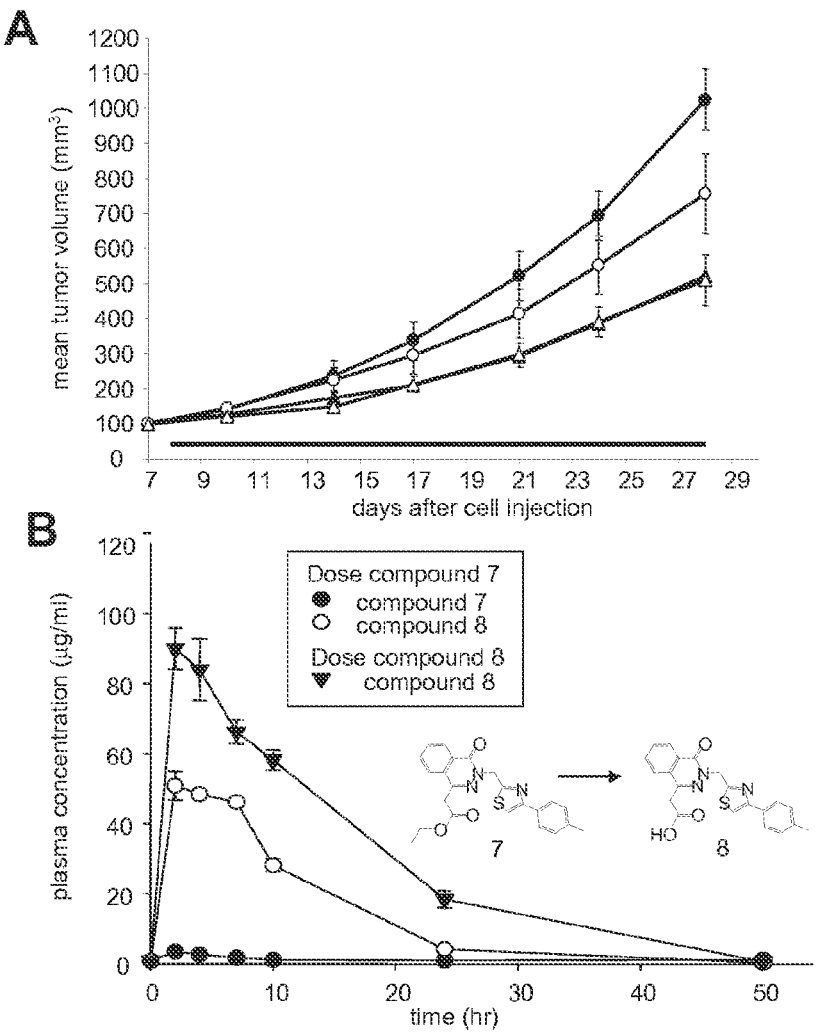

Figure 4
Antitumor activity and pharmacokinetics of compound 7. A, Antiumor activity of compound 7 administered by gavage at 200 mgkg in 0.1 ml Labrafil®: Labrasol® (8:2) (Gattefosse) daily for 20 days (shown by horizontal bar) and erlotinib by gavage at 10 mg/kg in 0.1 ml 0.2% Tween 20 daily for 20 days to female scid mice with a subcutaneous H12122 mut-KRAS tumors. Treatments were:(●) vehicle alone; (○) compound 7; (▲) erlotinib, and (△) erlotinib and compound 7. There were 10 mice per group and bars are SE. B, Pharmacokinetics of compound 7 and compound 8 (de-esterified acidic form of compound 7) in female C57Bl6 mice administered a single dose of compound 7 at 250 mg/kg 7 by gavage in 0.2 ml Labrafil®: Labrasol® (8:2). (●) parent compound and (○) acid metabolite. The acid metabolite compound 8 was also administered at 250 mg/kg by gavage in 0.2 ml Labrafil®: Labrasol® (8:2) with (▼) showing its plasma levels. There were 3 mice in each group and bars are SE. Insert shows structures of compound 7 and its acid metabolite compound 8.

| Cpd | Structure | Wt KRAS Cell Lines | | | Mutant KRAS Cell Lines | | |
|---|---|---|---|---|---|---|---|
| | | H1975 | H226 | HCC 95 | H1373 | H2122 | HCC 515 |
| 7 | 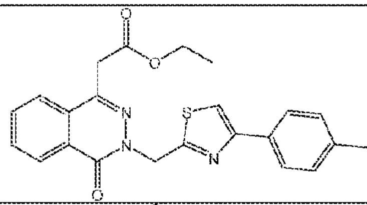 | > 100 μM | > 100 μM | > 100 μM | 51 μM | 27 μM | 70 μM |
| 9 | 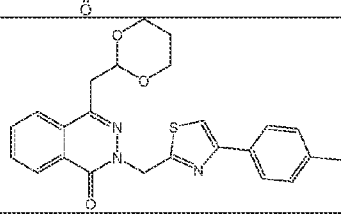 | 67 μM | 52 μM | 45 μM | 38 μM | > 100 μM | 37 μM |
| 10 | 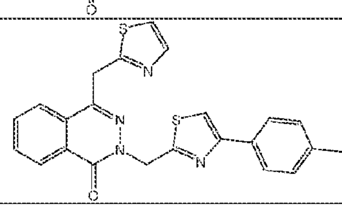 | 76 μM | >100 μM | 46 μM | 49 μM | 26 μM | 28 μM |
| 11 | 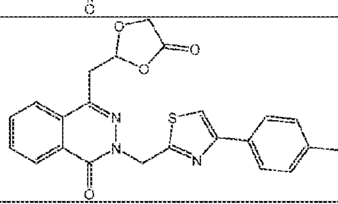 | 48 μM | 44 μM | 40 μM | 56 μM | > 100 μM | 34 μM |
| 8 | 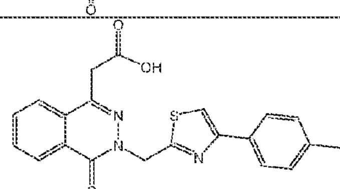 | > 100 μM | > 100 μM | > 100 μM | > 100 μM | > 100 μM | > 100 μM |
| 12 | 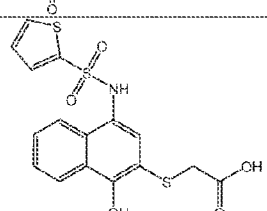 | 10 μM | 13 μM | 13 μM | 7 μM | 34 μM | 11 μM |

Figure 5
Activity of compound 7 analogs against wt-KRAS and mut-KRAS NSCLC cell lines.
Values are $IC_{50}$ for cell growth inhibition (3 day assay). Compound 12 is a different pharmacophore The X-Ray structure of inositol tetraphosphate (white sticks) overlaid with compound 12 (green sticks). A similarity of functional groups, their orientation and overall shape can be seen. The molecular surface used to retain similar compounds has been atom colored based on electrostatics and hydrophobicity.

Figure 7:
Selection of the best CNKR1 model to use for virtual screening. PH domain X-Ray structures with the highest similarity (blue ribbons) are superposed with the CNKR1 model (green ribbons) and its template X-Ray (1U5F, white ribbons) with best scores for compounds 7 (white ball and sticks), 8 (green ball and sticks) and 12 (yellow ball and sticks); co-crystal substrates of X-ray structures are rendered as white sticks and depicted in their corresponding binding sites.

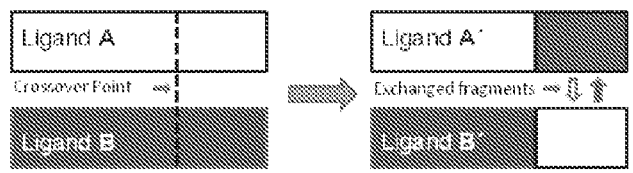

Figure 8.
Schematic view of the BREED process. Active ligands are disconnected in smaller portions to be later recombined, giving birth to novel ligands with active functional groups and scaffolds.

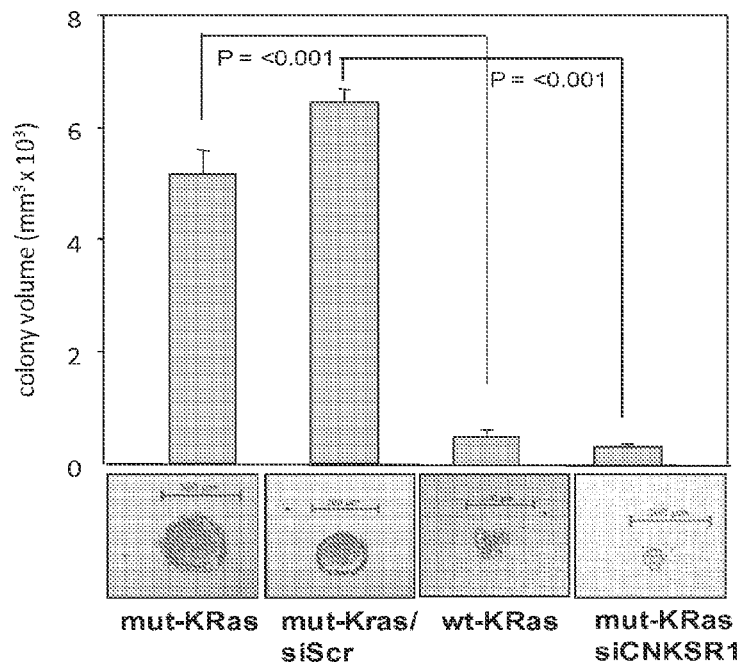

Figure 9
CNKSR1 is necessary for mut-KRAS anchorage independent cell growth
HCT-116 colon cancer cells (mutant-KRas G12D) (Mut-KRas) and the same cells with mutant-KRAS removed by homologous recombination leaving an allele of wild type-KRAS (wt-KRas) were used for the study. siCNKSR1 or siscrambled siRNA as a control was reverse transfected into the cells 24 hr before plating. The cell number was optimized for plating for the best cell density and found to be 20,000 cells per ml. The lid was removed from a 96-well Greiner plate and turned upside down. 20 µl of the 20,000 cells per mL suspension was then added directly into the middle of the circles found on the lid of the 96-well plate forming a small drop. 100 µL of media was added into the corresponding wells, used to maintain the temperature of the drops, and the lid was flipped back over carefully placing it back onto the plate without disturbing the drop. The plate was then placed into the incubator for 3 days to allow the cells to migrate to the bottom of the drop due to gravity. After 3 days, 400 µL of media was added to the corresponding wells a SCIVAX 96-well plate. The lid from the Greiner 96-well plate was removed and placed onto the SCIVAX 22 plate allowing the drop to come in contact with the media and placed back into the incubator. After one hour, 200 µL of media was removed from the corresponding wells carefully without disturbing the spheroid and imaged using an IN Cell Analyzer 6000 is a high performance laser confocal imager (GE Healthcare). Colony volume was calculated by the formula: volume = (diameter x width$^2$). Bars are mean of 3 determinations and bars are S.E.

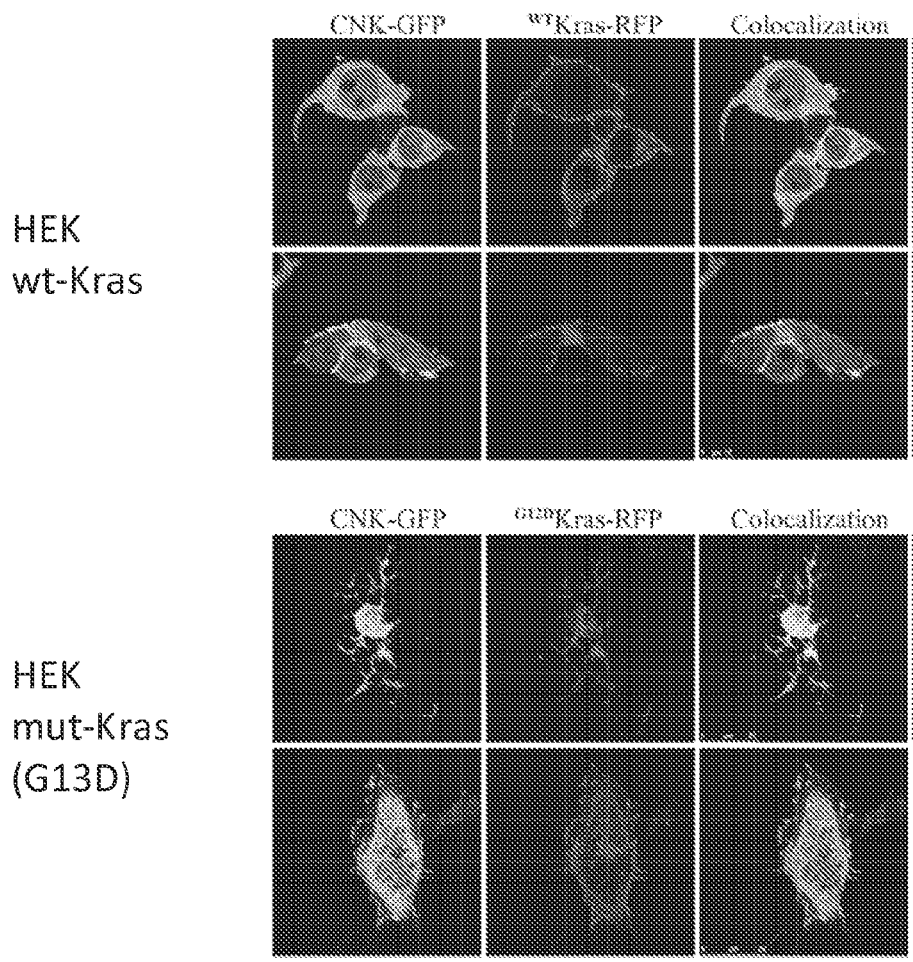

Figure 10
CNKSR1 (green) colocalizes with mutant-KRas (red) at the plasma membrane.
HEK-293 cells were transfected with CNKSR1-GFP and mut-KRas(G13D) for 16 hr. Two photon confocal microscopy shows that CNKSR1 is located at the plasma membrane and the cytoplasm in both wt-KRas and mut-KRas cells. KRas tends to be more membrane associated When cell the images are merged CNKSR1 and wt-KRas can be seen to be colocalized (within 500 nm) shown by the yellow/orange color. Mut-KRas colocalization is also seen but is more diffuse. Note the transformed phenotype of the mut-KRas cells.

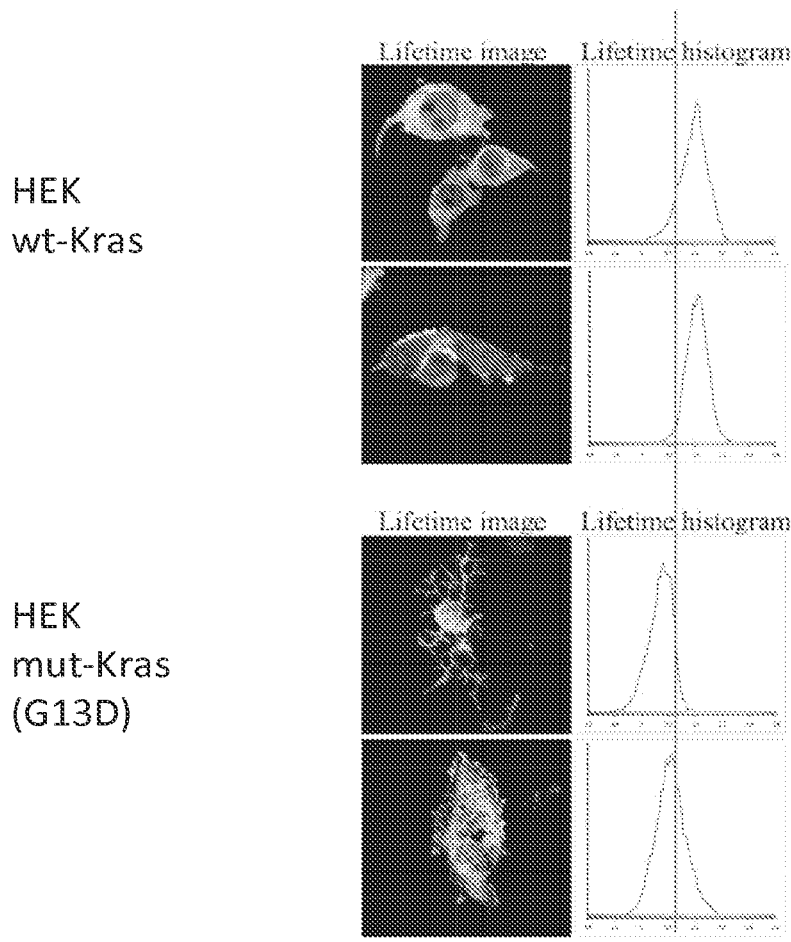

Figure 11
Fluorescence lifetime imaging microscopy (FLIM) showing that CNKSR1 binds directly to mut-KRas but not to wt-KRas in cells. HEK-293 cells were transfected with CNKSR1-GFP and mut-KRas(G13D and 16 hr later FLIM experiments were carried out using a Leica TCP SP5 inverted advanced confocal microscope system with internal photomultiplier tube (PMT) detector for TCSPC (time-correlated single-photon counting). The sample was excited with a tunable femtosecond (fs) titanium-sapphire laser with repetition rate of 80MHz and pulse width less then 80fs (Spectral Physics, Mai Tai BB). The wavelength used for two-photon excitation was 930 nm and the fluorescence was detected through a 525±25 nm interference filter. Images were obtained with oil-immersion objective (numerical aperture NA=1.4), a line scan speed of 400 Hz, with image size of 512x512 pixels. For FLIM analysis the pixels were reduced to 256x256. FLIM data was collected using Becker & Hickl SPC830 data and image acquisition card for TCSPC. The fluorescence decays were fitted with a single exponential decay model using Becker and 24 Hickl's SPCImage software and the GFP fluorescence lifetimes were calculated. The cell images in the left panel are two typical images false color for wt-KRas and mut-KRas cells and the fluorescence lifetimes shown on the right are for the entire cell measured by FLM. The results show a decrease in fluorescence lifetime in the right panel caused by when it CNKSR1 binds directly (i.e with a localization <100 nm) to mut-KRas but not to wt-KRas.

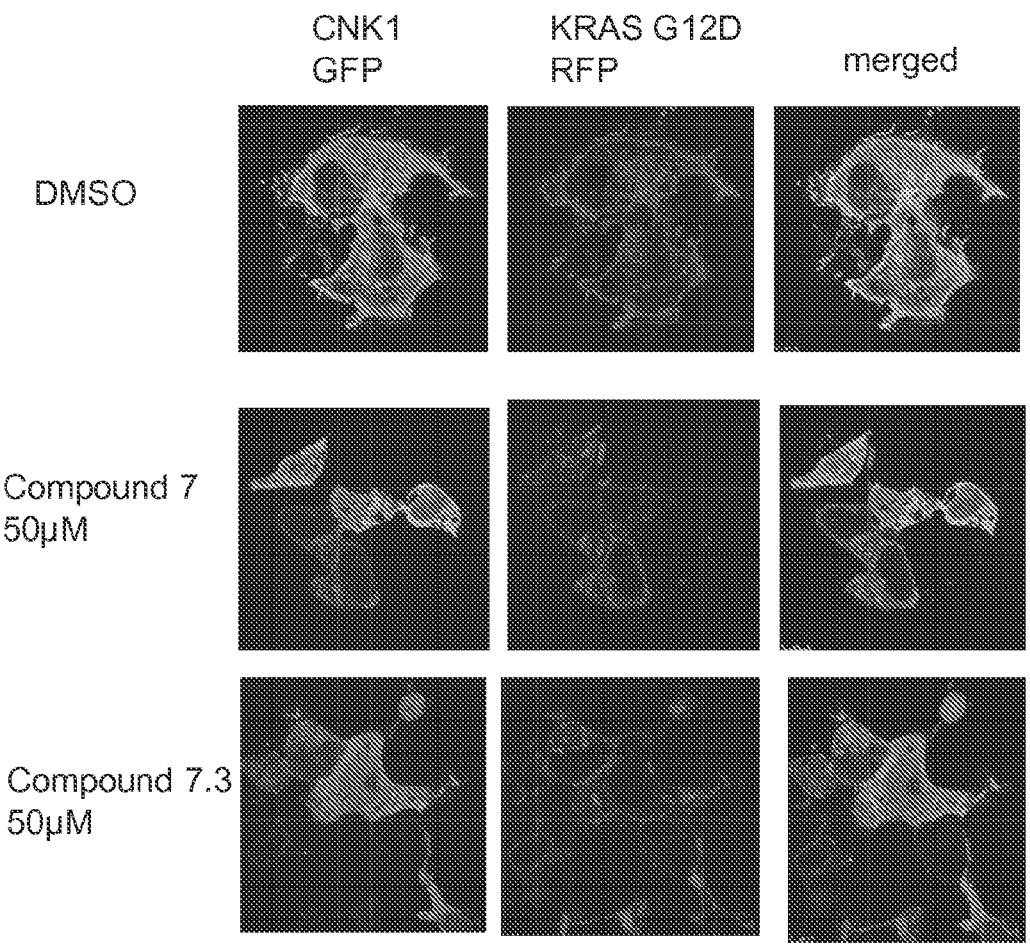

Figure 12

Compounds 7 and 9 (aka 7.3) block the membrane colocalisation of CNKSR1 (green) and mutant-KRas (red) at the plasma membrane, and lower total mutant KRas protein in the cell. HEK cells were transfected with CNKSR1-GFP and mut-KRas(G13D) and treated for 4 hr with vehicle (DMSO), 50 μM compound 7 or 50 μM compound 9. The results show colocalization (yellow/orange i.e. within 500 nm) of CNKSR1 and mut-KRas at the plasma membrane in untreated cells and a loss of this colocalisation in compound 7 and 9 treated cells. Also apparent caused by compound 7 and 9 is a decrease in total mut-KRas protein. Figures are typical of 3 determinations.

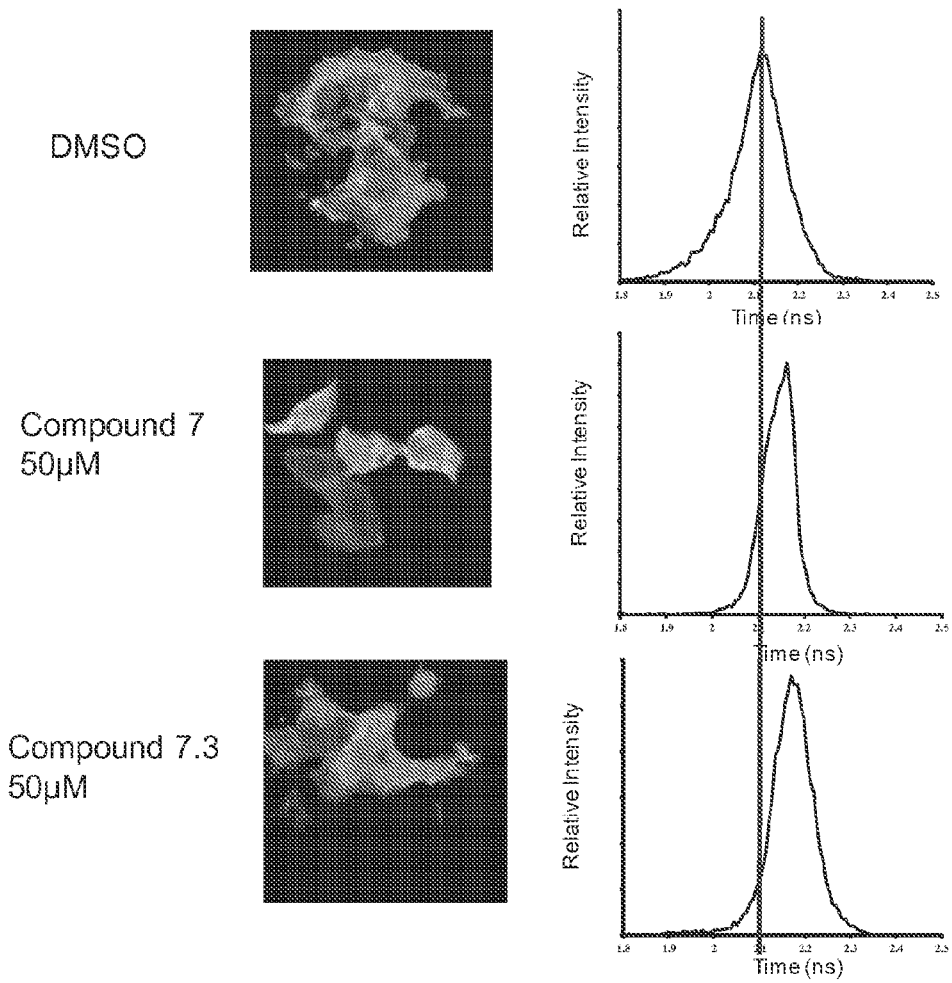

Figure 13
FLM studies showing compounds 7 and 9 (aka 7.3) inhibit the direct binding of CNKSR1 to mut-KRAS in cells. HEK-293 cells were transfected with CNKSR1-GFP and mut-KRas(G13D) for 16 hr and then treated for 4 hr with vehicle (DMSO), 50 μM compound 7 or 50 μM compound 9. The cell images are false color images with the fluorescence lifetimes shown on the right are for the entire cell measured by FLM. The results show that compounds 7 and 9 block the direct binding (i.e < 100 nm) of CNKSR1 and mut-KRas with a rightward shift in the fluorescence lifetime, similar to that seen in wt-KRas cells where CNKSR1 does not bind to wt-KRas.

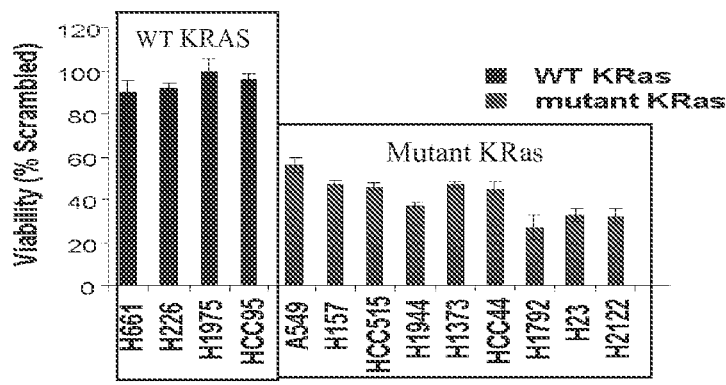

Figure 14A
CNKSR1 siRNA inhibits growth in lung cancer cells with mutated KRas. CNKSR1 siRNA in a panel of NSCLC cells. Cells were treated with either non targeting control siRNA or siCNKSR1. Results are displayed as cells treated with siCNKSR1 divided by cells treated with non-targeting control. (×100)

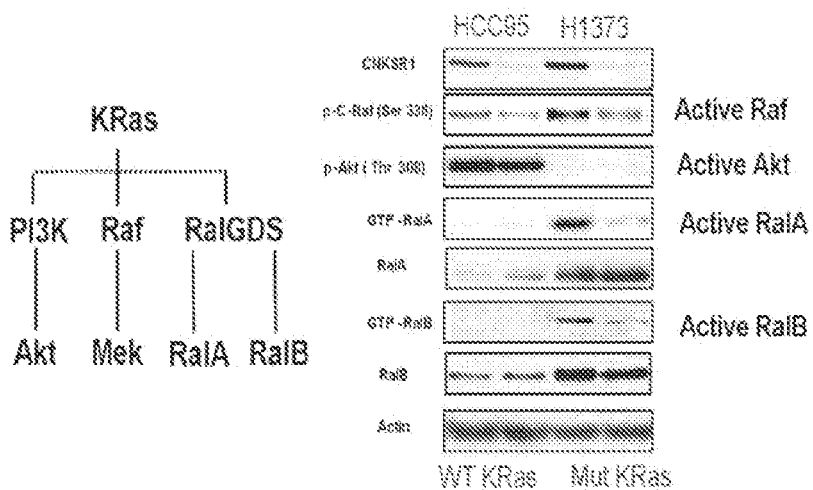

Figure 14B
CNKSR1 siRNA inhibits KRas signaling effecters Analysis of KRas effectors after siCNKSR1 treatment. Raf and Akt activation were measured using phosphorylation specific antibodies. Ral activation was measured by pull down for GTP bound protein.

PHT-782 Analogs with Increased activity. Activity of PHT-782 (Compound 7) and compounds 8 (Analog 1), 9 (Analog 2), 10 (Analog 3), 11 (Analog 4).

Initial CNK inhibitor leads demonstrate antitumor activity in A549 mut-KRAS human non-small cell lung cancer (NSCLC) xenograft in vivo antitumor activity of CPD 9: mice with A549 human NSCLC xenografts were dosed daily for 8 days with either vehicle, cpd 9 at 200 mg/kg ip, erlotinib at 75 mg/kg po or both 9 and erlotinib (shown by bar). Values mean ± S.E.

Modest antitumor activity has been observed with initial inhibitors that have shown CNK1 binding. Compound 9 (aka 7.3) and compound 78 (aka 7.10) were administered at 200 mg/kg i.p. to nu/nu mice baring A549 non small cell lung cancer xenografts with mut-KRAS(G12D) tumors.

METHODS AND COMPOSITIONS FOR INHIBITING CNKSR1

CLAIM OF PRIORITY

This application is a national phase application under 35 U.S.C. §371 of International Application No. PCT/CN2013/075505, filed Dec. 16, 2013 and entitled "METHODS AND COMPOSITIONS FOR INHIBITING CNKSR1," that claims priority to U.S. Provisional Patent Application No. 61/737,658, filed Dec. 14, 2012 the disclosures of which are incorporated by reference in their entirety and for all purposes.

CROSS-REFERENCE

This application claims priority to U.S. Provisional Patent Application No. 61/737,658 entitled Methods and Compositions for Inhibiting CNKSR1 filed on Dec. 14, 2013.

GOVERNMENT INTEREST

The United States government may have certain rights to this invention pursuant to State of Texas; CPRIT; High Impact Grant, "KRAS the elephant in the room of cancer chemotherapy;" Number: RP100686.

BACKGROUND

Single point mutations of at least one of the RAS genes (KRAS, HRAS, and NRAS) are found in many human cancers, particularly in colon, lung and pancreatic cancer. RAS mutations are most commonly found in KRAS (about 85%), less commonly in NRAS (about 12%) and rarely in HRAS (about 3%). KRAS encodes two splice variants, A and B, with divergent C-terminal sequences due to the alternate utilization of exon 4. Mutant KRAS (mut-KRAS) may be present in up to about 25% of all human tumors. Mut-KRAS may play a critical role in driving tumor growth and resistance to therapy. An agent with even a modest effect on mut-KRAS activity, or one that exhibits selective inhibition of a subset of mut-RAS could have a major impact on therapy, and decrease cancer patient suffering and morbidity. Thus, finding new agents that inhibit the growth of mut-KRAS tumors is desirable.

SUMMARY

Embodiments are directed to small molecule drugs that may inhibit CNKSR1 through PH-domain binding and may selectively block the growth of mut-KRAS cancer cells without affecting wt-KRAS cells. In embodiments, inhibiting the CNKSR1 gene may block the growth of mut-KRAS cancer cells without affecting wt-KRAS cancer cell growth. In embodiments, CNKSR1 has a PH-domain that may be critical for allowing mut-KRAS to signal tumor growth. In embodiments, iterative molecular modeling and the SPR binding approach may be used to identify PH-domain inhibitors.

Some embodiments provide a compound of formula IA:

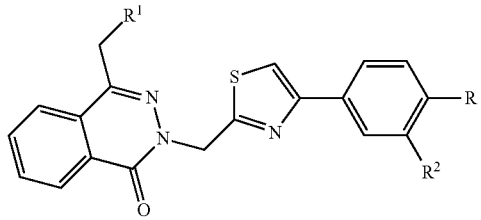

Formula IA wherein
R is —$C_1$-$C_4$ alkyl, —$NO_2$, —$NH_2$, $NHSO_2CH_3$, —$C_1$-$C_5$ cylcloalkyl, or —$CF_3$;
$R^2$ is H or
R and $R^2$ combine as

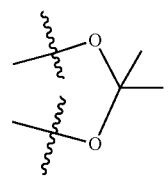 [SMILES: *OC(C)(C)O*]

to form a bicyclic moiety with the carbons to which they are attached;
$R^1$ is —C(O), —C(O)O($C_1$-$C_4$alkyl), —C(O)OH, —$C_1$-$C_4$alkyl-OH, —CH(OH)($CH_2$)$_n$$NH_2$, —CH(OH), —C(OH)$CNO_2$, —($CH_2$)$_n$ $NO_2$, —CHO, —C(O)NHR$^3$,

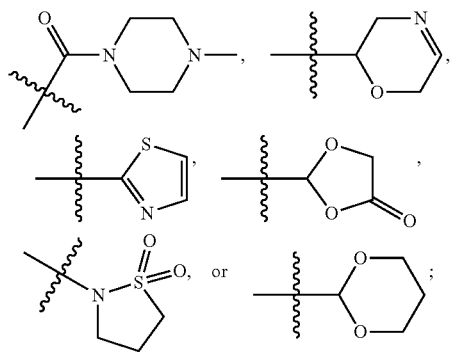

n is 1, 2, 3, or 4;
$R^3$ is —$C_1$-$C_4$alkyl, —$C_1$-$C_2$ alkyl-C(O)$NH_2$, —S(O)$_2$$CH_3$;
provided when R is Me, $R^1$ is NOT —C(O)O$CH_2$$CH_3$;
or a pharmaceutically acceptable salt thereof.
In some embodiments, $R^1$ is

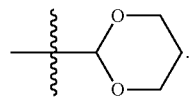 [SMILES: *C1OCCCO1]

In some embodiments, $R^1$ is —C(O)O($C_1$-$C_4$alkyl).
In some embodiments, $R^1$ is —$C_1$-$C_4$alkyl-OH.
In some embodiments, $R^1$ is —C(O)NHR$^3$.

In some embodiments, R1 is
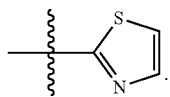 [SMILES: *c1nccs1]
In some embodiments, R is methyl.
In some embodiments, R is —C1-C5 cylcloalkyl.
In some embodiments, the compound is selected from:
8
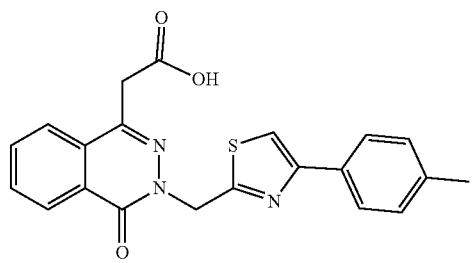
9
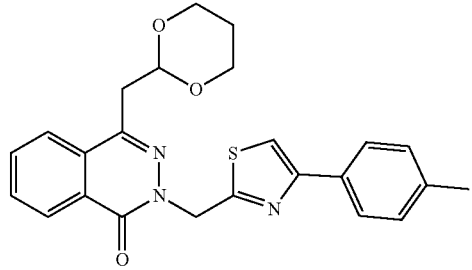
10
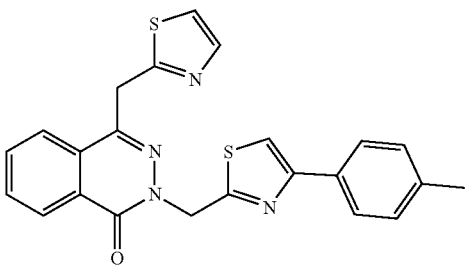
11
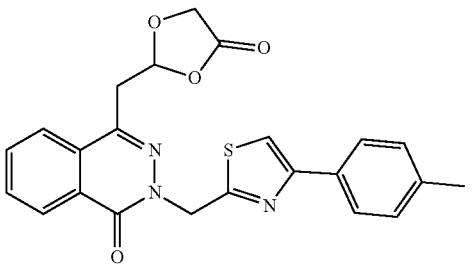
78
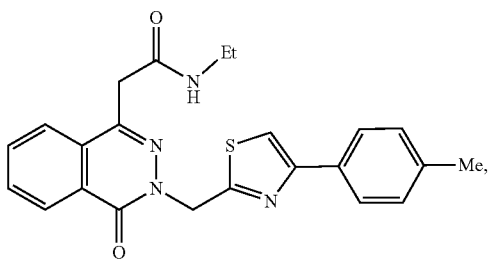
79
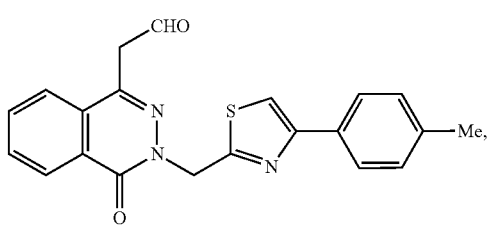
80
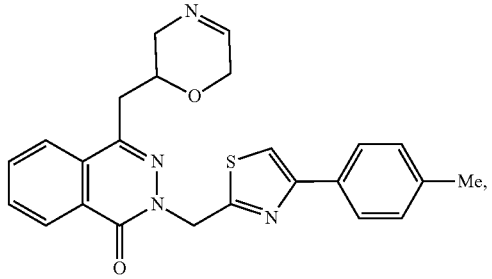
81
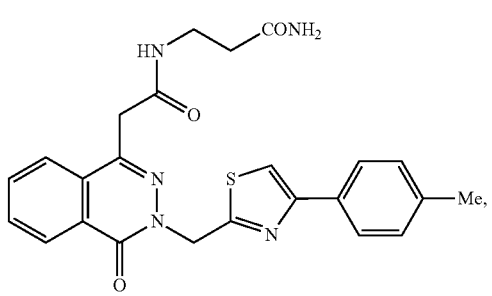
82
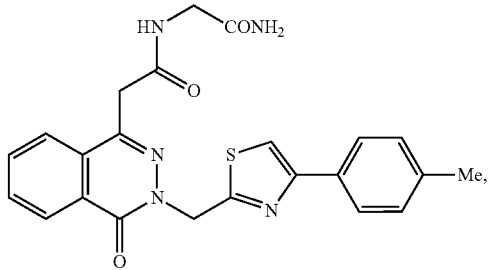
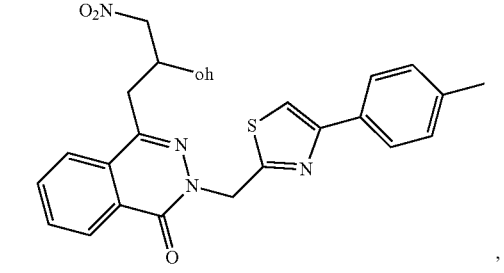

-continued
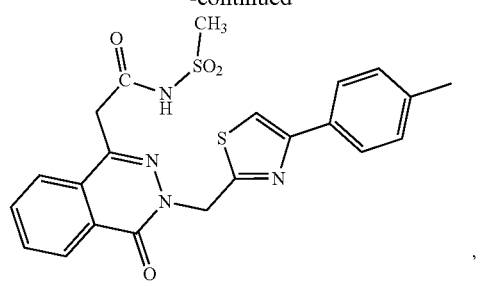
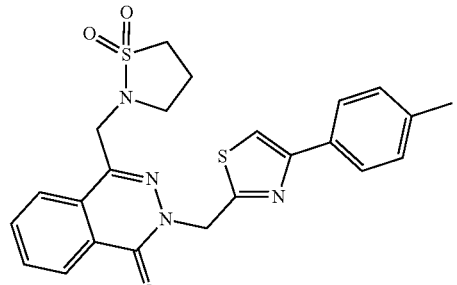
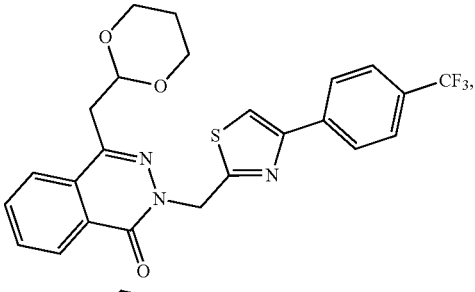
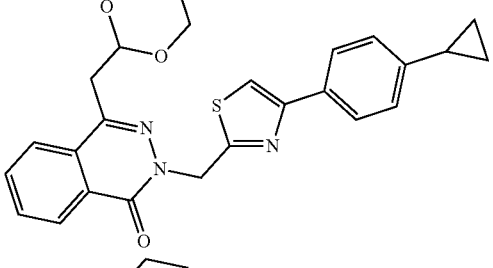
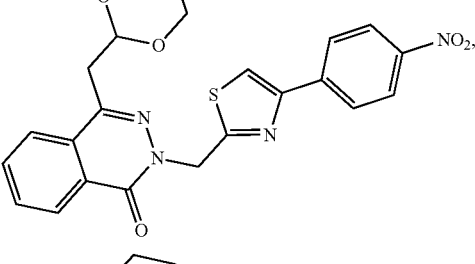
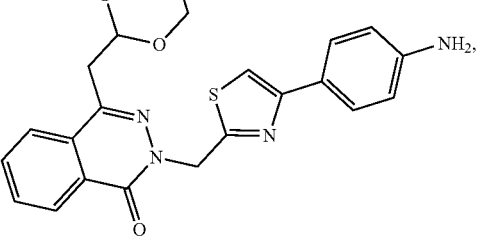
-continued
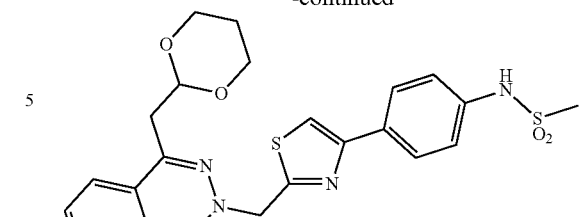
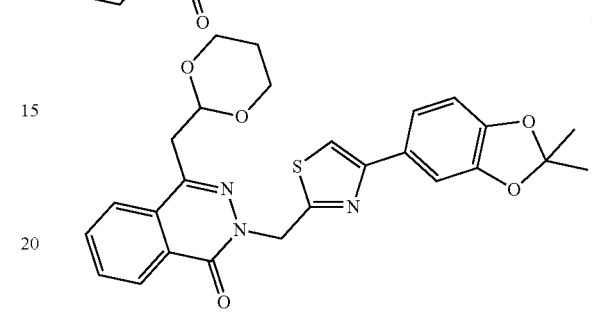
Some embodiments provide a compound of Formula IIA:
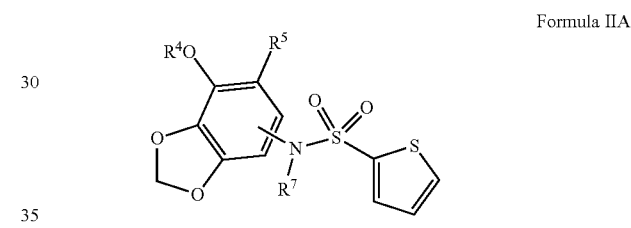
Formula IIA
wherein
R⁴ is —H, —C₁-C₄alkyl,
R⁵ is —C₁-C₄alkyl-OH, —C₂-C₆alkenyl-OH, —C₁-C₄alkykl-C(O)—C₁-C₄alkyl, —C₂-C₆alkenyl-C(O)—C₁-C₄alkyl, —C₁-C₄alkykl-C(O)—C₃-C₅cycloalkyl, —C₂-C₆alkenyl-C(O)—C₃-C₅cycloalkyl,
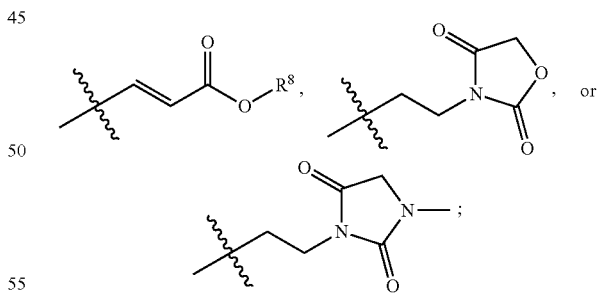
R⁸ is C₁-C₄alkyl, or —C₃-C₅ cycloalkyl;
R⁷ is H or
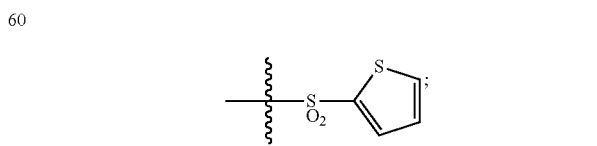
or a pharmaceutically acceptable salt thereof.

In some embodiments, R4 is methyl.

In some embodiments, R7 is

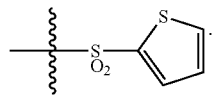

In some embodiments, R5 is —C2-C6alkenyl-OH, or —C2-C6alkenyl-C(O)—C1-C4alkyl.

In some embodiments, R5 is —C1-C4alkyl-OH, or —C1-C4alkyl-C(O)—C1-C4alkyl.

In some embodiments, R5 is

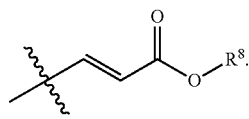

In some embodiments, R8 is cyclopropyl or cyclobutyl.

In some embodiments, R7 is H.

In some embodiments, R5 is

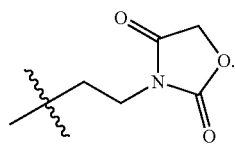 [SMILES: *CCN1C(=O)COC1=O]

In some embodiments, R5 is

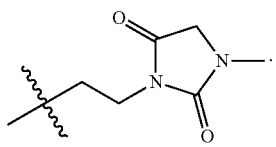 [SMILES: *CCN1C(=O)CN(C)C1=O]

In some embodiments the compound is selected from:

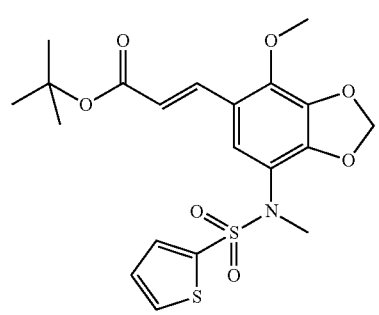

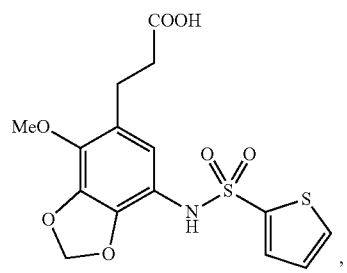

83

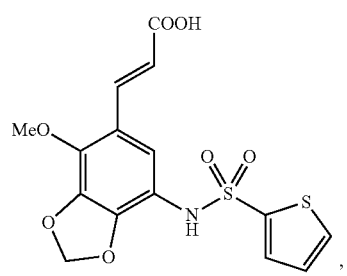

84

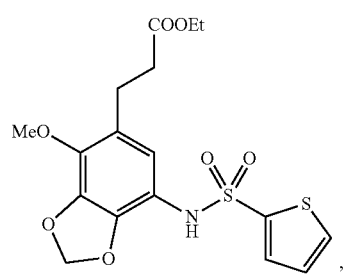

85

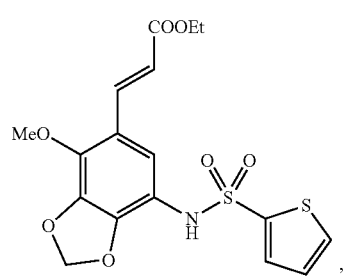

86

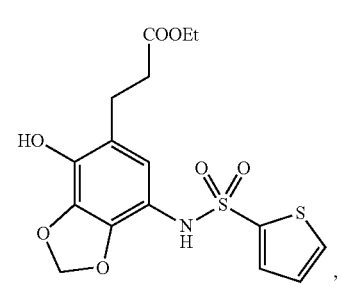

87

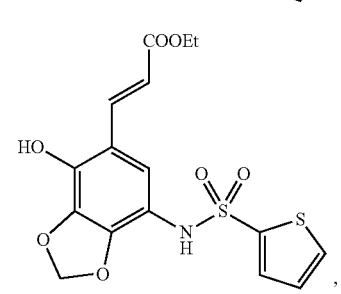

88

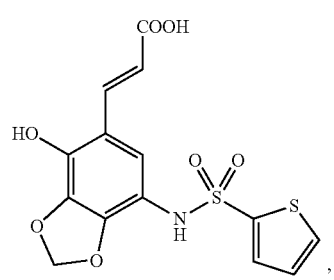
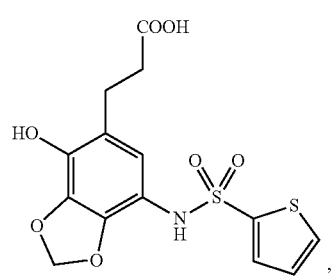
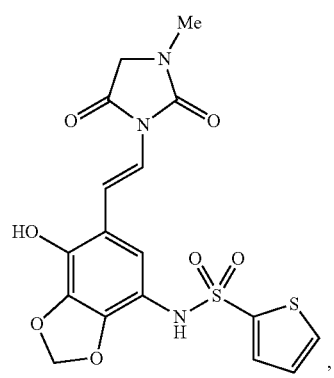
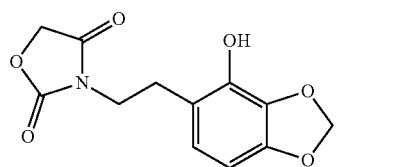
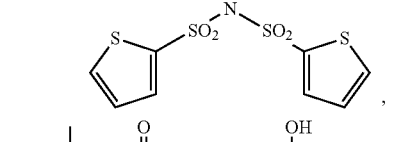
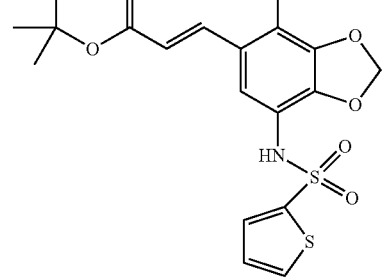
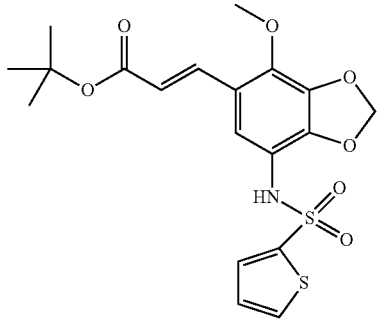
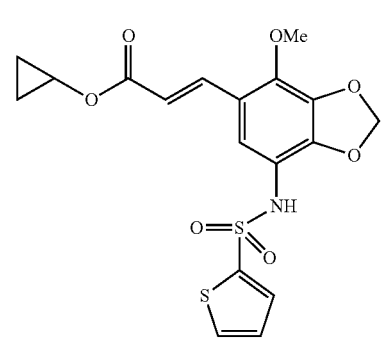
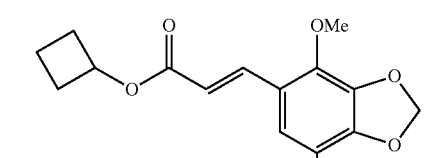
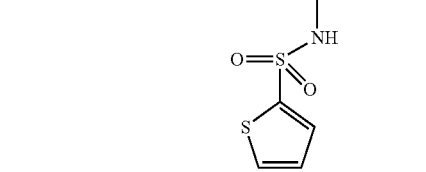
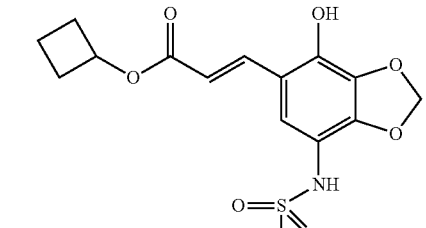
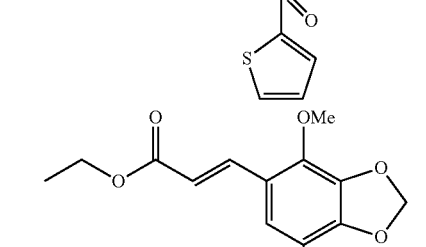
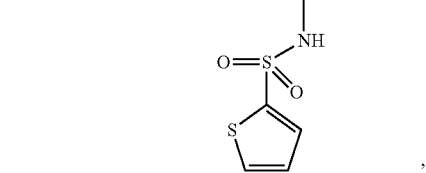

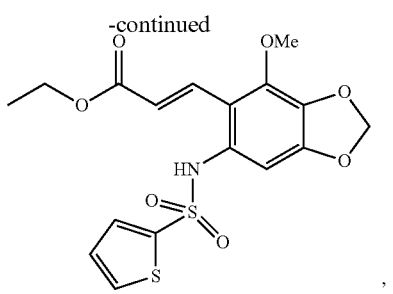

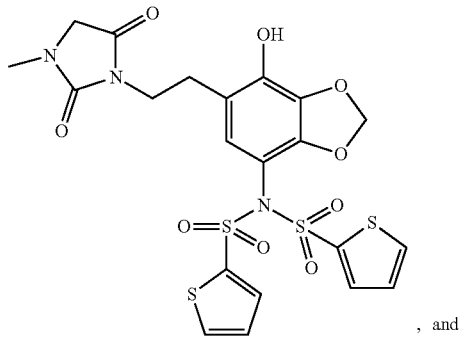

, and

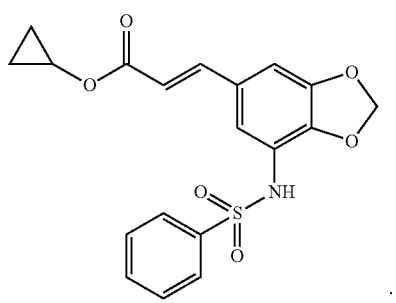

.

Some embodiments provide a compound of Formula IIIA:

Formula IIIA

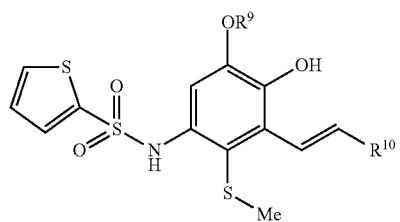

wherein
R$^9$ is —H or —C$_1$-C$_4$alkyl;
R$^{10}$ is —C(O)O C$_1$-C$_4$alkyl, —C(O)OH,

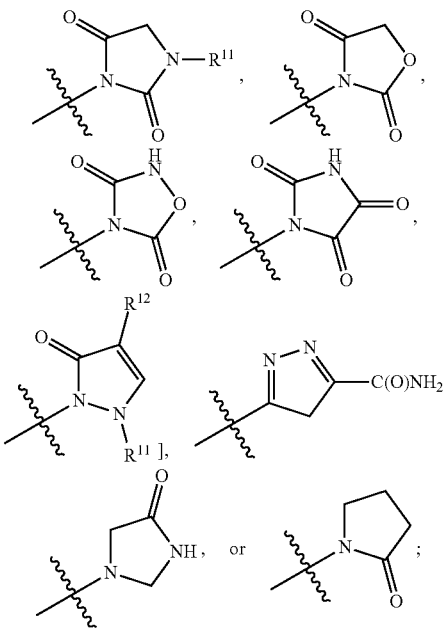

R$^{11}$ is H or C$_1$-C$_4$alkyl;
R$^{12}$ is C$_1$-C$_4$alkyl;
or a pharmaceutically acceptable salt thereof.
In some embodiments, R9 is methyl.
In some embodiments, R10 is —C(O)O C1-C4alkyl.
In some embodiments, the C1-C4 alkyl is ethyl.
In some embodiments, R10 is

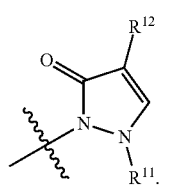

In some embodiments, R10 is

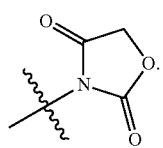 [SMILES: *N1C(=O)COC1=O]

In some embodiments, R10 is

In some embodiments the compound is selected from:

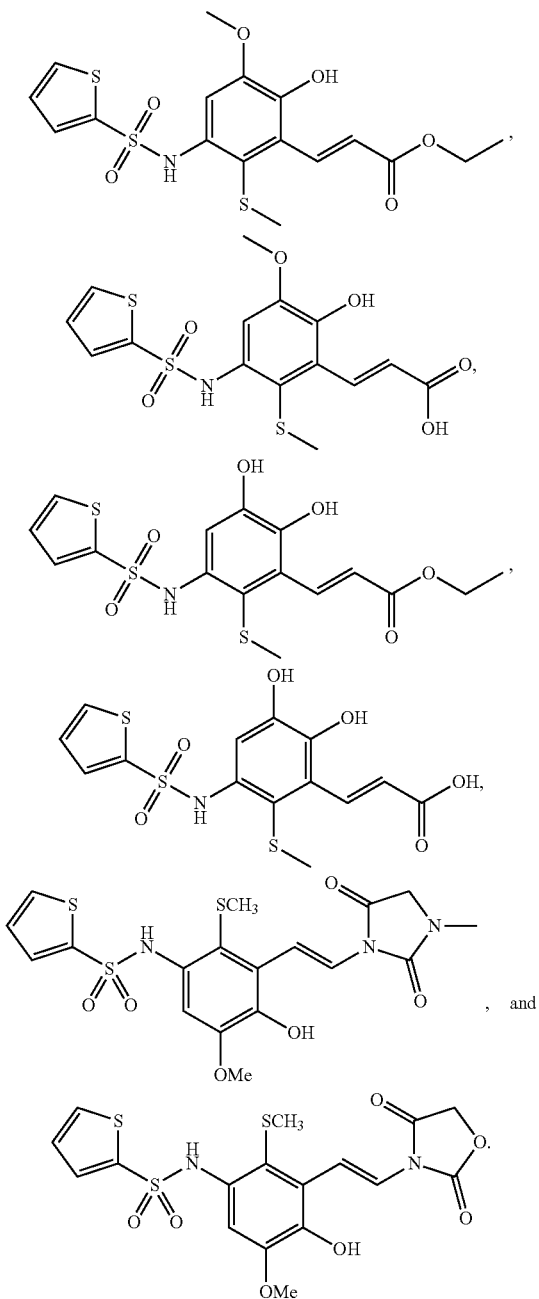

Some embodiments provide a compound of formula IVA:

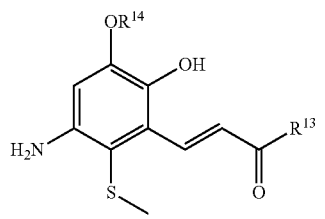

Formula IVA

Wherein $R^{13}$ is —OH or $C_1$-$C_4$ alkyl;
$R^{14}$ is H or $C_1$-$C_4$ alkyl;
Or a pharmaceutically acceptable salt thereof
In some embodiments, R13 is methyl.
In some embodiments, $R^{14}$ is methyl.
In some embodiments, the compound is selected from

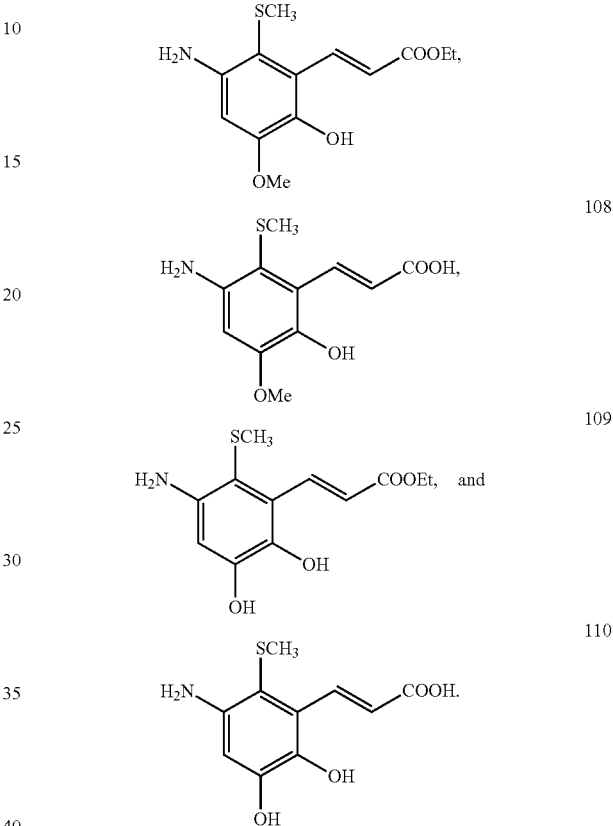

Methods of treating cancer and/or inhibiting CNKSR1 comprising administering an effective amount of the above described compounds or pharmaceutical compositions containing them are also disclosed.

BRIEF DESCRIPTION OF DRAWINGS

The file of this patent contains at least one photograph or drawing executed in color. Copies of this patent with color drawing(s) or photograph(s) will be provided by the Patent and Trademark Office upon request and payment of necessary fee.

For a fuller understanding of the nature and advantages of the present invention, reference should be had to the following detailed description taken in connection with the accompanying drawings, in which:

FIG. 1 is a scheme illustrating translational modifications of RAS proteins, in accordance with embodiments.

FIG. 2 is a collection of plots illustrating the use of CNKSR1 as a target for inhibition of mut-KRAS growth, in accordance with embodiments.

FIG. 3 contains a table of identified compounds and a collection of plots illustrating their use in the inhibition of mut-KRAS growth, in accordance with embodiments.

FIG. 4 is a collection of plots illustrating anti-tumor activity and pharmacokinetics of compound #7, in accordance with embodiments.

FIG. 5 is a table of identified compounds illustrating their use in the inhibition of mut-KRAS growth, in accordance with embodiments.

FIG. 7 is an illustration of the CNKR1 model, in accordance with embodiments.

FIG. 8 is a schematic of the BREED process, in accordance with embodiments.

FIG. 9 is an illustration of the inhibition of 3D growth by siKRas and siCNKSR1, in accordance with embodiments.

FIG. 10 is a collection of photographs depicting CNKSR1 colocalizes with mutant KRas at the plasma membranes, in accordance with embodiments.

FIG. 11 is a collection of photographs and lifetime histograms of Fluorescence lifetime imaging microscopy (FLIM) showing that CNKSR1 binds directly to mut-KRas but not to wt-KRas in cells in accordance with embodiments.

FIG. 12 is a collection of photographs showing compounds 7 and 9 blocking the membrane colocalisation of CNKSR1 and mutant-KRas at the plasma membrane, and lower total mutant KRas protein in the cell, in accordance with embodiments.

FIG. 13 is a collection of photographs and lifetime histograms of fluorescence lifetime imaging microscopy for compounds 7 and 9 showing the compounds inhibit the direct binding of CNKSR1 to mut-KRAS in cells, in accordance with embodiments.

FIG. 14 is a graph and schematic showing inhibition of growth in lung cancer cells with mutated KRas and inhibition of KRas signaling effectors.

DETAILED DESCRIPTION

Figure 6:
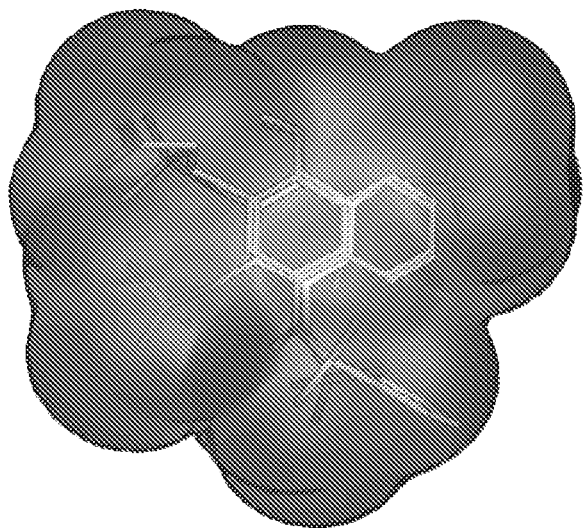
FIG. 6 is an overlay of the x-ray structures of compound #12 and inositol, in accordance with embodiments.

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a compound, can include, but is not limited to, providing a compound into or onto the target tissue; and/or providing a compound systemically to a patient by, e.g., intravenous injection or oral administration, whereby the therapeutic reaches the target tissue.

The term "animal" as used herein includes, but is not limited to, humans and non-human vertebrates such as wild, domestic and farm animals.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, the term "therapeutic" means an agent utilized to treat, combat, ameliorate, prevent or improve an unwanted condition or disease of a patient. In part, embodiments of the present invention are directed to the treatment of cancer or the decrease in proliferation of cells.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per day will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Single point mutations of at least one of the RAS genes (KRAS, HRAS, and NRAS) are found in many human cancers, particularly in colon, lung and pancreatic cancer. RAS mutations are most commonly found in KRAS (about 85%), less commonly in NRAS (about 12%) and rarely in HRAS (about 3%). KRAS encodes two splice variants, A and B, with divergent C-terminal sequences due to the alternate utilization of exon 4. Mutant KRAS (mut-KRAS) may be present in up to about 25% of all human tumors. Mut-KRAS may play a critical role in driving tumor growth and resistance to therapy. An agent with even a modest effect on mut-KRAS activity, or one that exhibits selective inhibition of a subset of mut-RAS could have a major impact on therapy, and decrease cancer patient suffering and morbidity. Thus, finding new agents that inhibit the growth of mut-KRAS tumors is arguably the most important unmet need in cancer therapy today.

Early attempts to develop GTP-competitive antagonists to RAS protein, analogous to ATP-competitive antagonists of protein-tyrosine kinases, were found to be impractical because of the picomolar binding of GTP to RAS. The next approach, and one that gained considerable traction, was to prevent the membrane binding of RAS by blocking RAS farnesylation using cell permeable CAAX peptidomimetics or small molecule farnesyl transferases (FT) inhibitors. Several potent agents were developed that showed dramatic activity in HRAS cell lines and mouse tumor models. However, it was found that the activity was limited to oncogenic HRAS which is found in only a small portion of human tumors, and that oncogenic NRAS and KRAS were resistant to FT inhibition because of alternative geranylgeranylation. Other efforts to develop antisense or siRNA inhibitors of KRAS, or inhibitors of Rce1 and Icmt responsible for CAAX signal processing have so far not provided effective KRAS antitumor agents. The currently favored approach is to block downstream signaling targets activated by KRAS such as PI-3-K, RAF and mitogen activated protein kinase kinase (MEK), and several clinical trials underway with combinations of these inhibitors. However, a limitation of the approach may be that different mut-KRAS amino acid substitutions engage different downstream signaling effectors, and it may be necessary to have a number inhibitors available for each of the pathways. It may be preferable to have an inhibitor that works with all forms of mut-KRAS and the approach we have adopted is to identify genes that are activators of mut-KRAS activity to provide molecular targets for the development of selective mut-KRAS inhibitors.

Following the strategy to identify genes that positively regulate mut-KRAS activity, CNKSR1 (connector enhancer of kinase suppressor of RAS 1) has been identified. The CNKSR1 protein is associated with KRAS in the membrane signaling nanocluster, and knockdown of CNKSR1 may cause inhibition of mut-KRAS tumor cell growth and signaling without inhibition of wt-KRAS cell growth. Furthermore, CNKSR1 has a potentially druggable pleckstrin homology (PH) domain.

Embodiments of the invention are directed toward compounds of the formula:

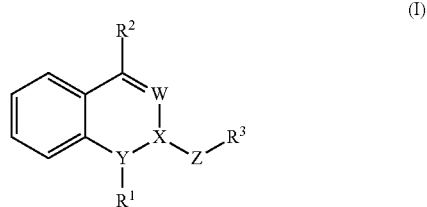

(I)

wherein

W and X are each independently selected from a carbon atom and a nitrogen atom;

Y is a carbon atom;

Z is selected from methylene, an oxygen atom, and a sulfur atom;

the bond order between X and Y is selected from a single bond or a double bond;

$R^1$ is selected from a hydroxyl, a thiol, optionally substituted amines, optionally substituted ethers, optionally substituted sulfanes, an oxygen atom forming a ketone with Y, an optionally substituted nitrogen atom forming an imine with Y, and a sulfur atom forming a thione with Y;

$R^2$ is selected from hydroxyl, thiol, optionally substituted amines, optionally substituted ethers, optionally substituted sulfanes, optionally substituted alkyl chains with 1 to 3 carbon atoms, optionally substituted sulfonimidic acids, optionally substituted sulfonimidates; and $R^3$ is selected from acetic acid, acetate, alkylacetate, and 4-p-tolylthiazol-2-yl;

and wherein the compound is not:

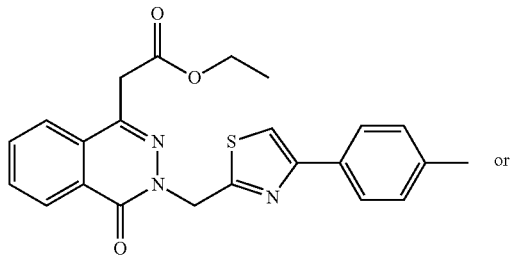

7 or

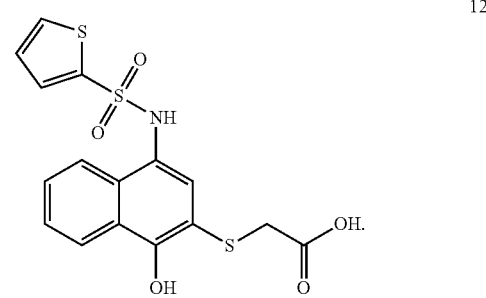

12

Embodiments of the invention are directed toward compounds of the formula:

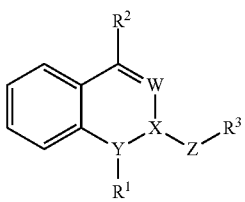

(I)

wherein
W and X are each independently selected from a carbon atom and a nitrogen atom;
Y is a carbon atom;
Z is selected from methylene and a sulfur atom;
the bond order between X and Y is selected from a single bond or a double bond;
$R^1$ is selected from a hydroxyl and an oxygen atom forming a ketone with Y;
$R^2$ is selected from an optionally substituted carbon atom and an optionally substituted sulfonimidate; and
$R^3$ is selected from acetate and 4-p-tolylthiazol-2-yl;
and wherein the compound is not:

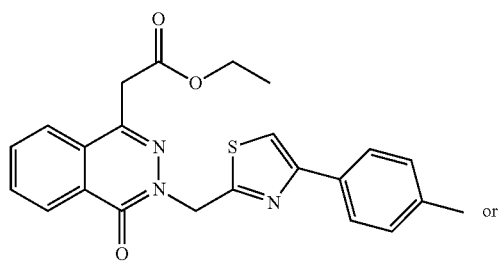

or

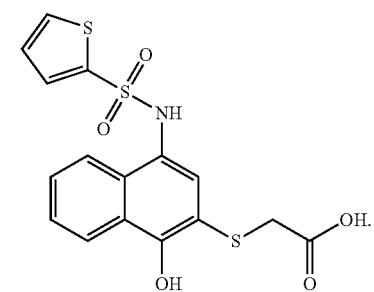

Some embodiments are drawn toward compounds of formula IA:

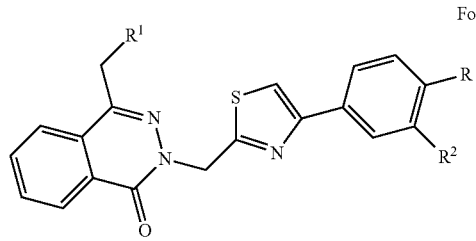

Formula I wherein
R is —$C_1$-$C_4$ alkyl, —$NO_2$, —$NH_2$, $NHSO_2CH_3$, —$C_1$-$C_5$ cylcloalkyl, or —$CF_3$;

$R^2$ is H or
R and $R^2$ combine as

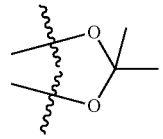 [SMILES: *OC(C)(C)O*]

to form a bicyclic moiety with the carbons to which they are attached;
$R^1$ is —C(O), —C(O)O($C_1$-$C_4$alkyl), —C(O)OH, —$CH_2OH$, —CH(OH)($CH_2$)$_n$$NH_2$, —CH(OH), —C(OH)CNO$_2$, —($CH_2$). $NO_2$, —CHO, —C(O)NHR$^3$,

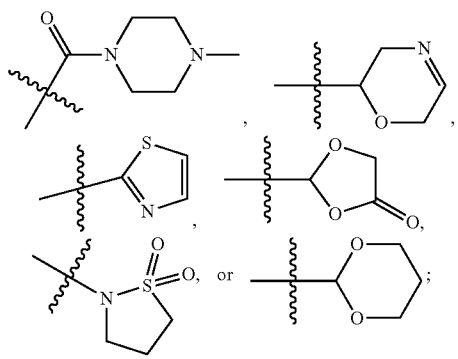

n is 1, 2, 3, or 4;
$R^3$ is —$C_1$-$C_4$alkyl, —$C_1$-$C_2$ alkyl-C(O)$NH_2$, —$S(O)_2CH_3$;
provided when R is Me, $R^1$ is NOT —C(O)OCH$_2$CH$_3$ [compound 7];
or a pharmaceutically acceptable salt thereof.
In some embodiments, $R^1$ is

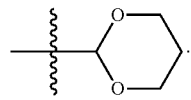

In some embodiments, $R^1$ is —C(O)O($C_1$-$C_4$alkyl). In some embodiments, the $C_1$-$C_4$alkyl is ethyl.
In some embodiments, $R^1$ is —$C_1$-$C_4$alkyl-OH.
In some embodiments, $R^1$ is —C(O)NHR$^3$.
In some embodiments, $R^1$ is

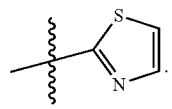 [SMILES: *c1nccs1]

In some embodiments, R is methyl.
In some embodiments, R is —$C_1$-$C_5$ cylcloalkyl. In some embodiments $C_1$-$C_5$ cycloalkyl is cyclopropyl. In some embodiments, $C_1$-$C_5$cycloalkyl is cyclobutyl.
In some embodiments, a compound of formula IA is selected from:

8
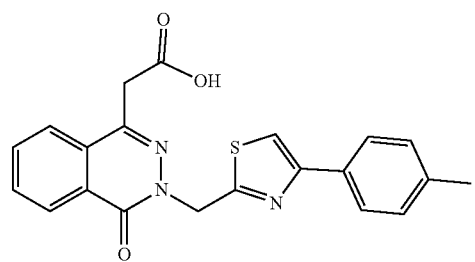,
9
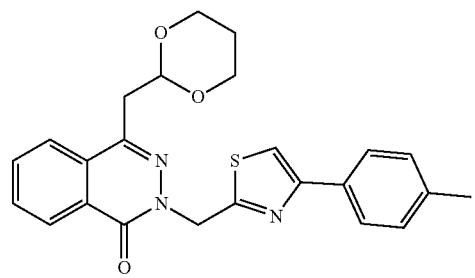,
10
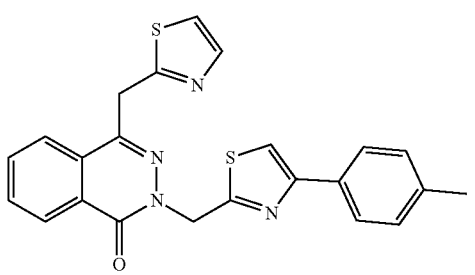,
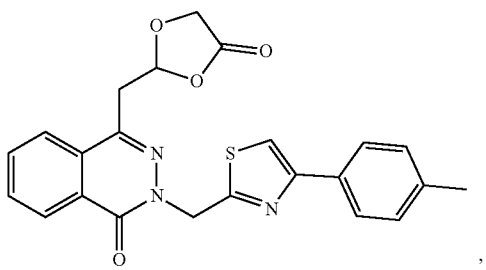,
78
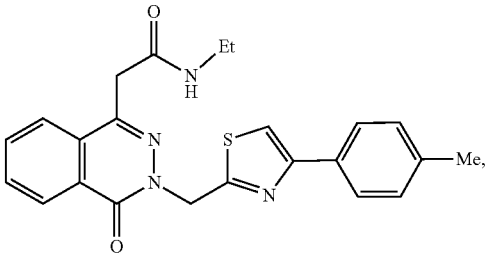,
79
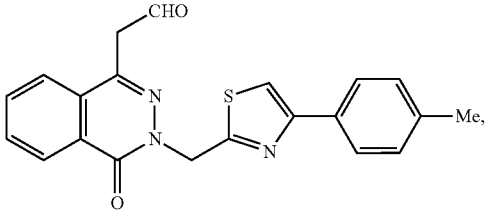,
80
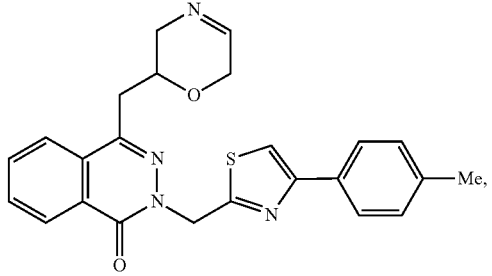,
81
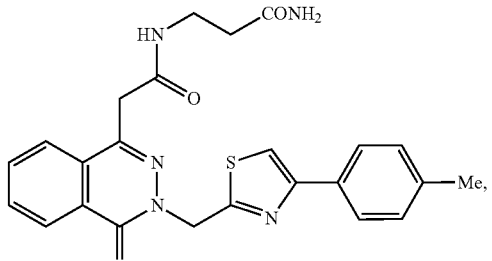,
82
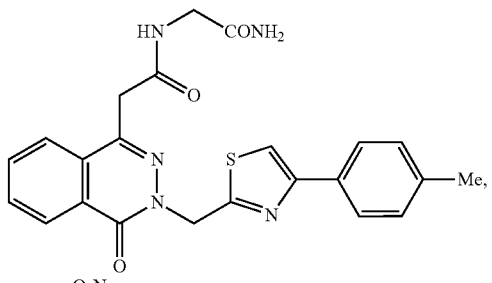,
11
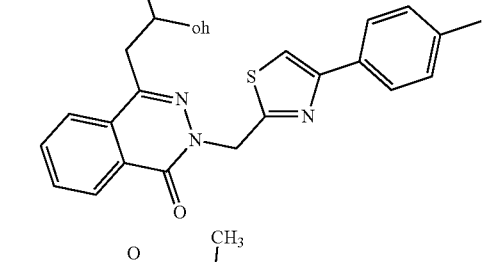,
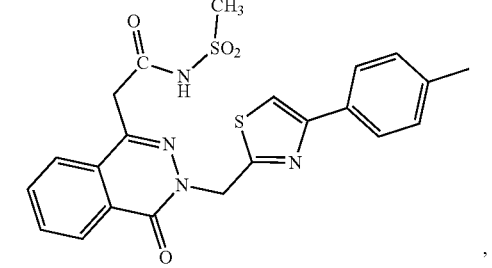,
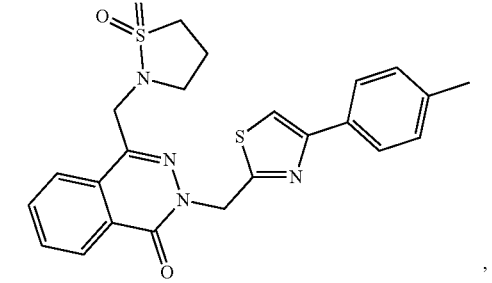,

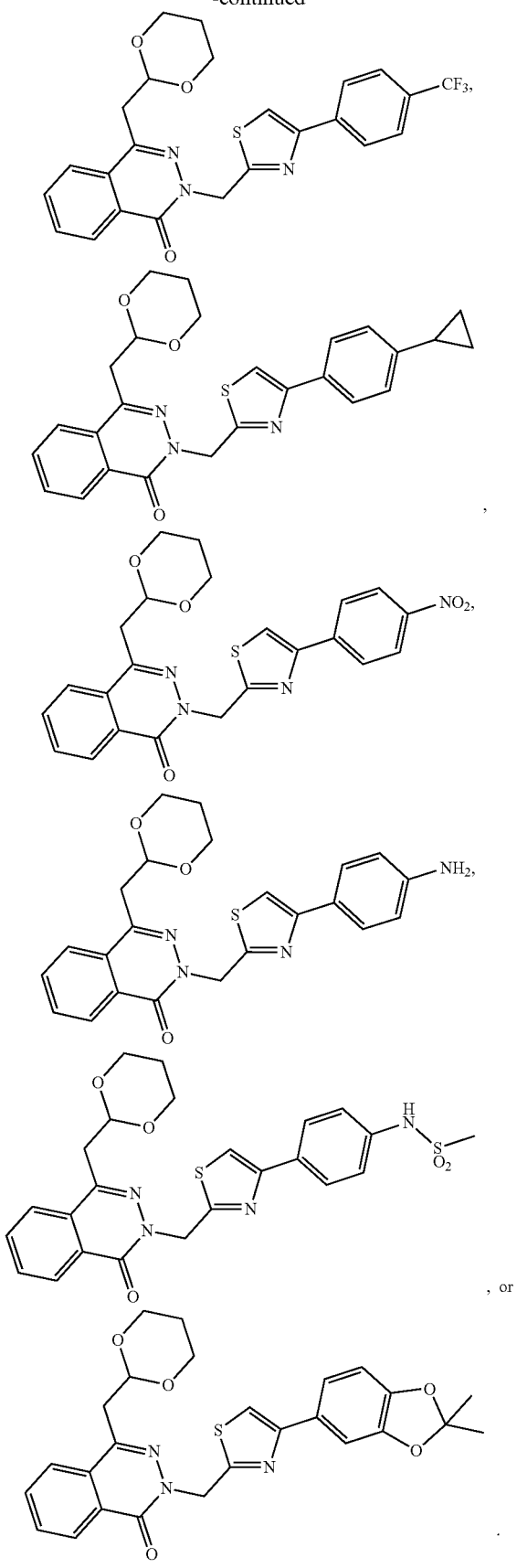, or

Embodiments of the invention are directed toward compounds of the formula:

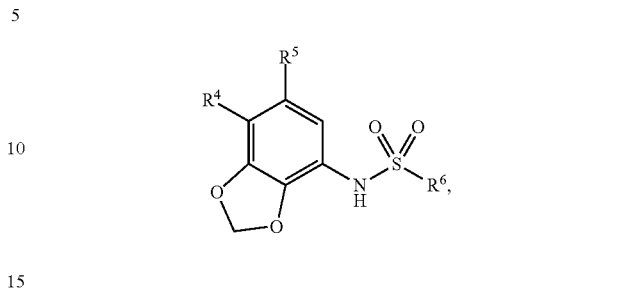

and pharmaceutically acceptable salts thereof,
wherein
R⁴ is selected from a hydroxyl, a thiol, optionally substituted amines, and an optionally substituted ether;
R⁵ is selected from hydroxyl, thiol, optionally substituted amines, optionally substituted ethers, optionally substituted sulfanes, optionally substituted alkyl chains with 1 to 3 carbon atoms, optionally substituted sulfonimidic acids, optionally substituted sulfonimidates; and
R⁶ is selected from acetic acid, acetate, alkylacetate, and 4-p-tolylthiazol-2-yl.

One preferred embodiment has R⁴ selected from a hydroxyl, and an optionally substituted ether; R⁵ as a substituted alkyl chains with 1 to 3 carbon atoms; and R⁶ as 4-p-tolylthiazol-2-yl.

Some embodiments are directed toward compounds of formula IIA:

Formula II

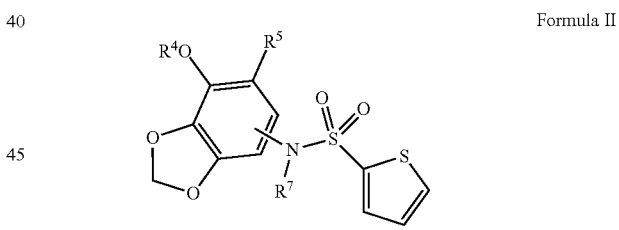

wherein
R⁴ is —H, —C₁-C₄alkyl,
R⁵ is —C₁-C₄alkyl-OH, —C₂-C₆alkenyl-OH, —C₁-C₄alkykl-C(O)—C₁-C₄alkyl, —C₂-C₆alkenyl-C(O)—C₁-C₄alkyl, —C₁-C₄alkykl-C(O)—C₃-C₅cycloalkyl, —C₂-C₆alkenyl-C(O)—C₃-C₅cycloalkyl,

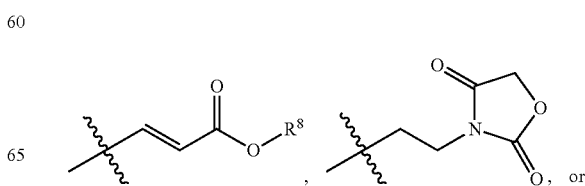, or

-continued

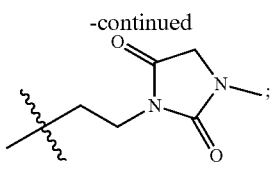

$R^8$ is $C_1$-$C_4$alkyl, or —$C_3$-$C_5$ cycloalkyl;
$R^7$ is H or

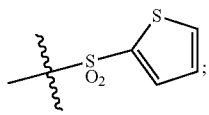

or a pharmaceutically acceptable salt thereof

Embodiments of the invention are directed toward compounds of the formula:

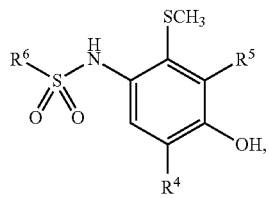

and pharmaceutically acceptable salts thereof,
wherein
$R^4$ is selected from a hydroxyl, a thiol, optionally substituted amines, and an optionally substituted ether;
$R^5$ is selected from hydroxyl, thiol, optionally substituted amines, optionally substituted ethers, optionally substituted sulfanes, optionally substituted alkyl chains with 1 to 3 carbon atoms, optionally substituted sulfonimidic acids, optionally substituted sulfonimidates; and
$R^6$ is selected from acetic acid, acetate, alkylacetate, thiazol-2-yl, and 4-p-tolylthiazol-2-yl. In one preferred embodiment, $R^4$ is selected from a hydroxyl, and an optionally substituted ether; $R^5$ is a substituted alkyl chains with 1 to 3 carbon atoms; and $R^6$ is thiazol-2-yl.

Some embodiments are drawn to compounds of formula IIIA:

Formula III

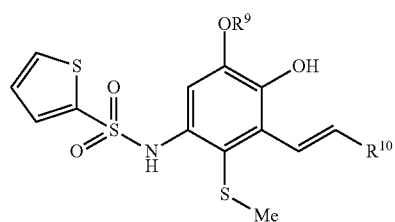

wherein
$R^9$ is —H or —$C_1$-$C_4$alkyl-$CH_3$;
$R^{10}$ is —C(O)O $C_1$-$C_4$alkyl [Et], —C(O)OH,

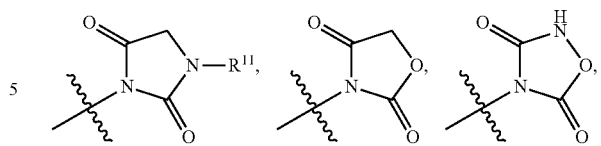

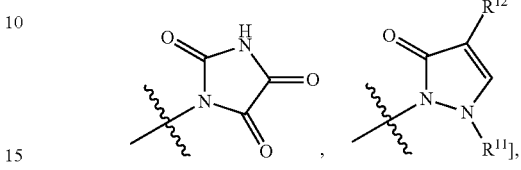

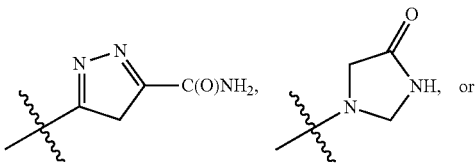

$R^{11}$ is H or $C_1$-$C_4$alkyl;
$R^{12}$ is $C_1$-$C_4$alkyl;
or a pharmaceutically acceptable salt thereof The compounds of some embodiments are selected from:

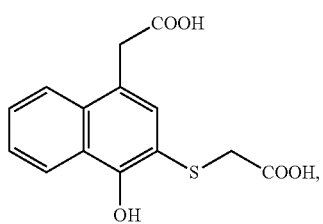

1

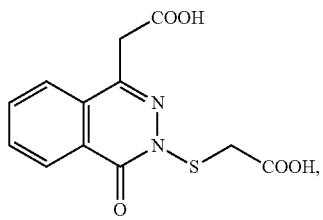

2

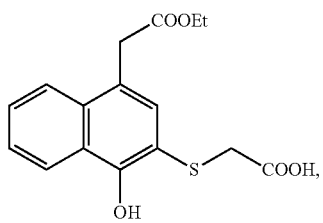

3

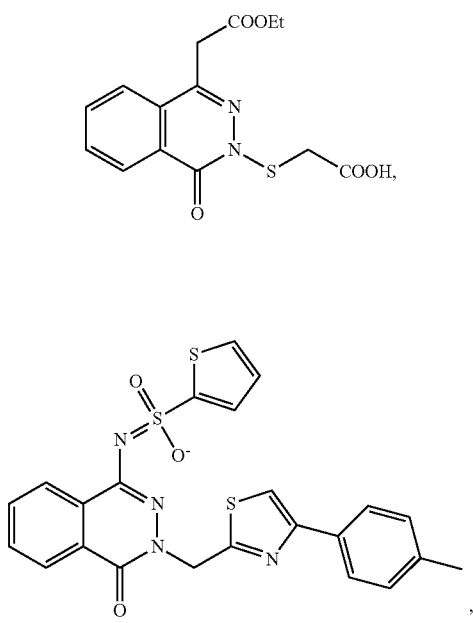
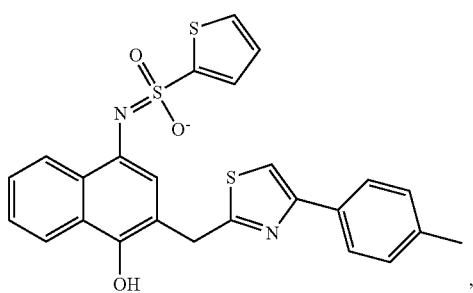
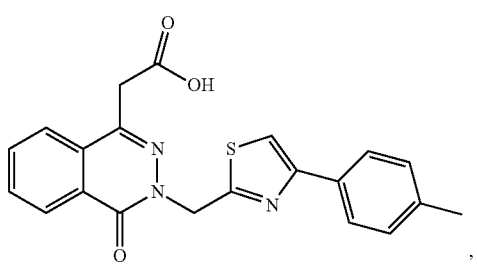
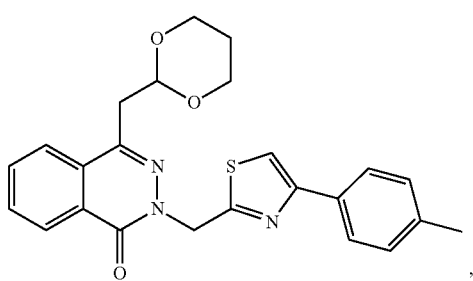
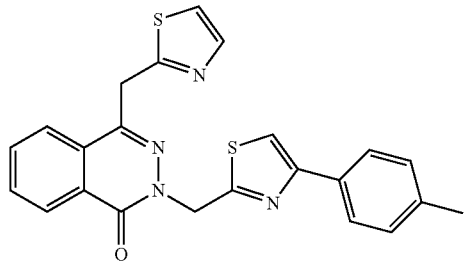
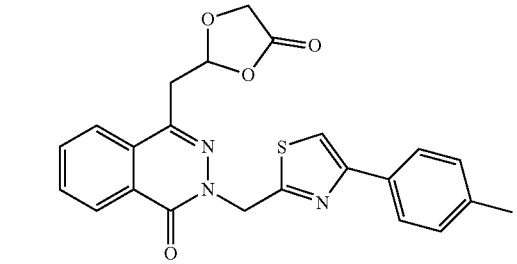
Some embodiments are directed to compounds of formula IVA:
Formula IVA
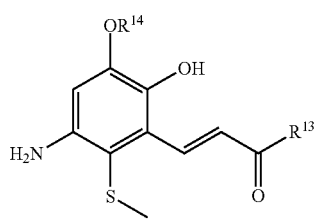
wherein $R^{13}$ is —OH or $C_1$-$C_4$ alkyl;
$R^{14}$ is H or $C_1$-$C_4$ alkyl.
In some embodiment, $R^{13}$ is methyl.
In some embodiments, $R^{14}$ is methyl.
In some embodiments, a compound of formula IVA is selected from
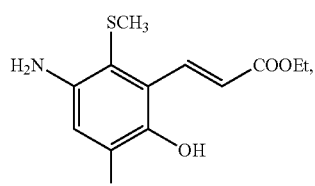
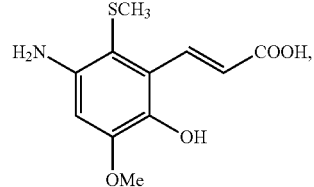

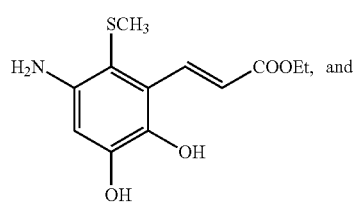

109

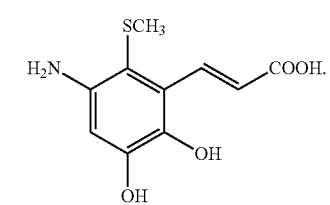

110

Embodiments are directed toward pharmaceutical compositions comprising a compound of formula I and a pharmaceutically acceptable excipient. In such embodiments, the compounds of formula I are present in a therapeutically effective amount.

Embodiments are directed toward methods of treating cancer comprising administering an effective amount of compounds of formula I.

Embodiments are directed toward methods of inhibiting CNKSR1 comprising administering an effective amount of compounds of formula I.

Embodiments are directed toward methods of treating cancer comprising administering an effective amount of compounds selected from 1-12,

13

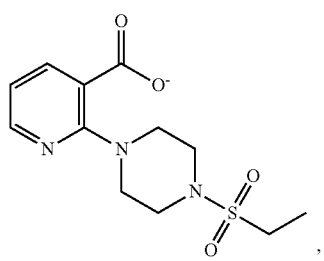

14

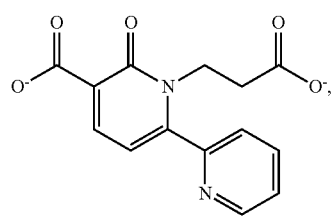

15

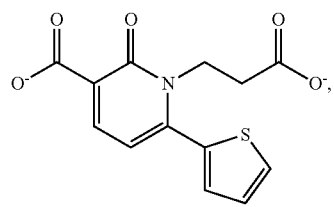

16

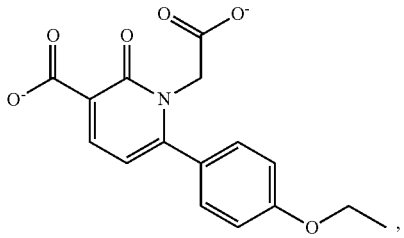

17

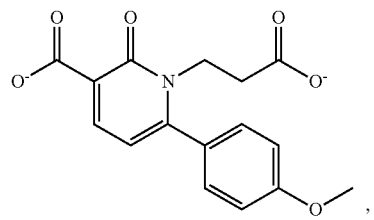

18

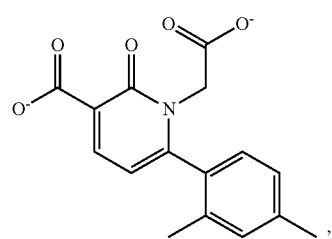

19

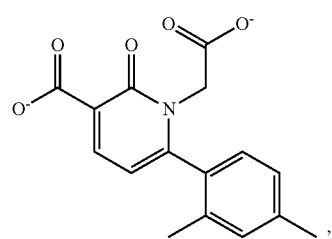

20

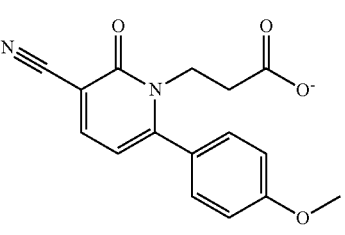

21

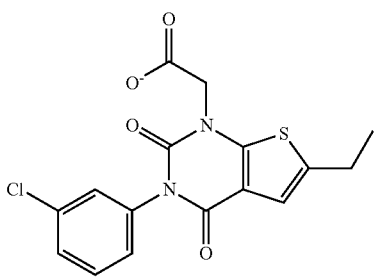

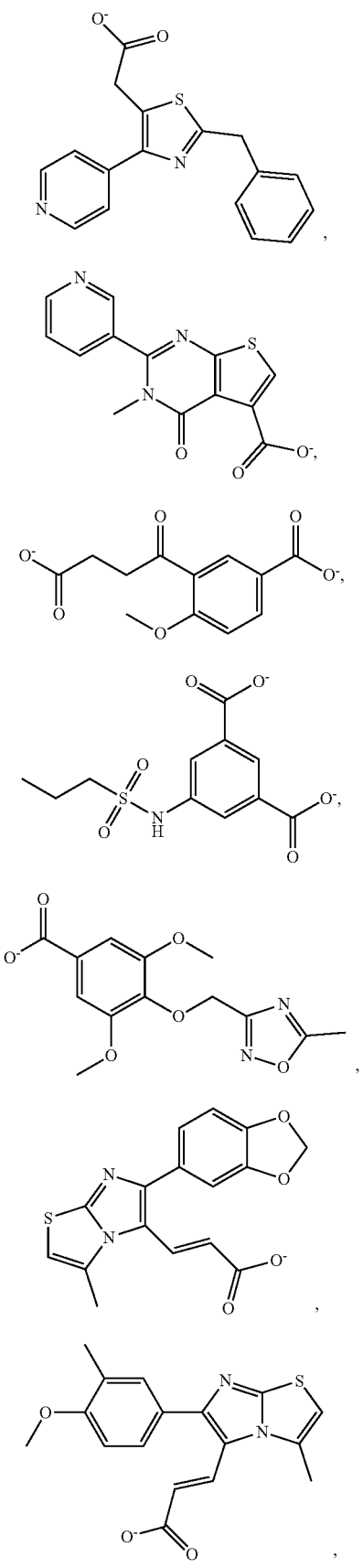
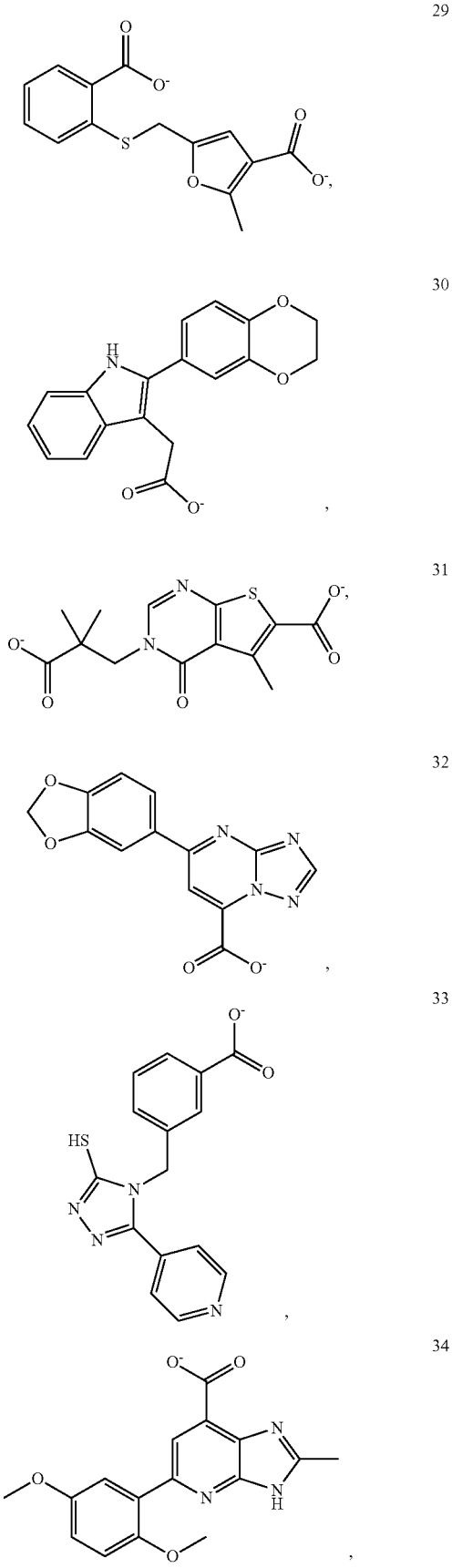

33
-continued
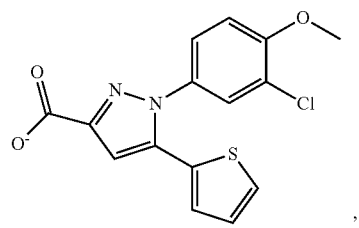
35
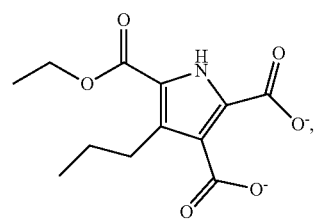
36
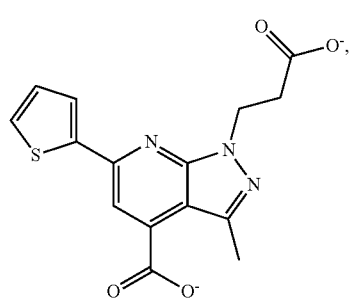
37
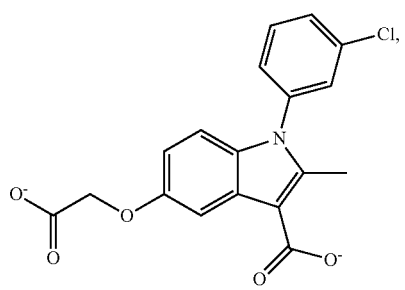
38
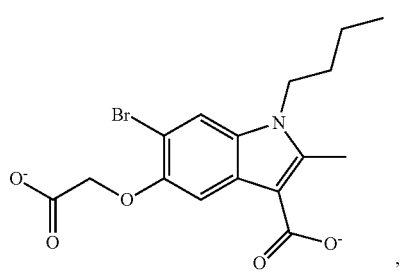
39
34
-continued
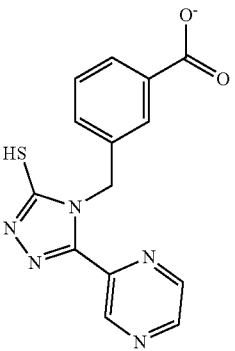
40
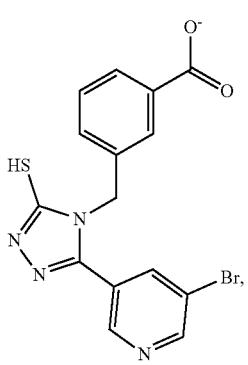
41
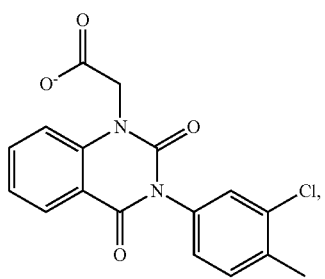
42
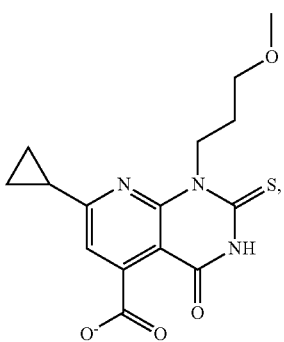
43
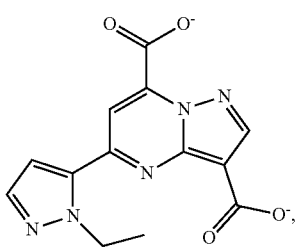
44

45 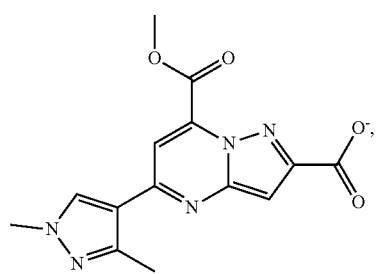
46 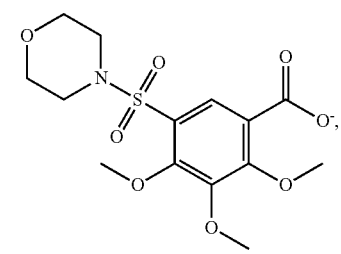
47 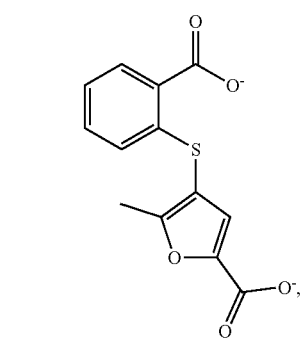
48 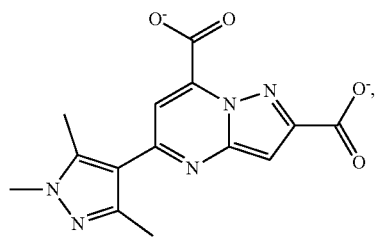
49 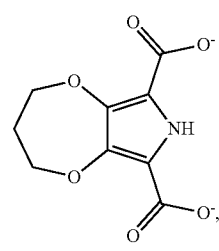
50 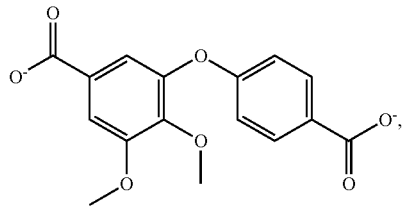
51 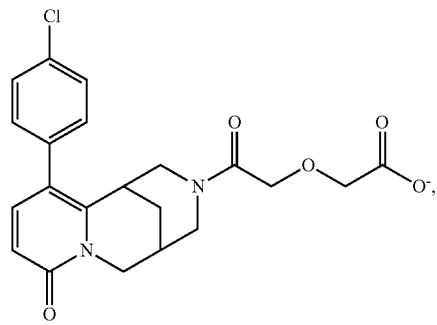
52 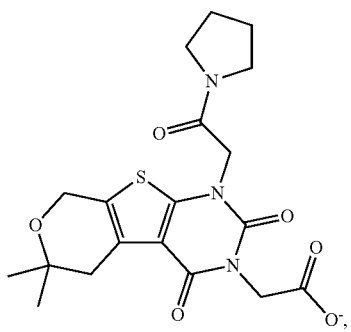
53 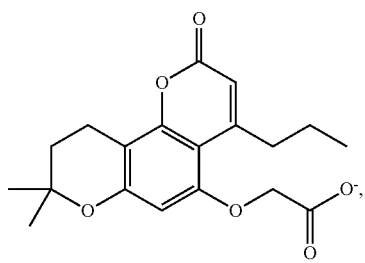
54 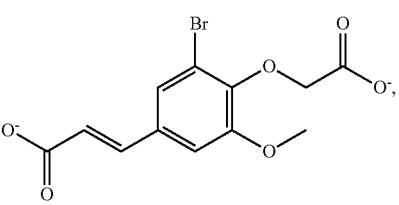
55 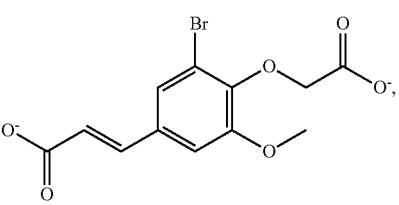
56 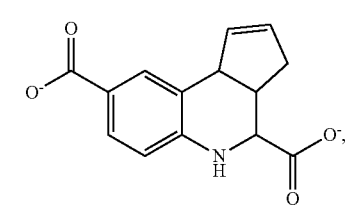

-continued

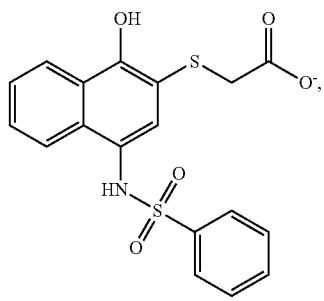

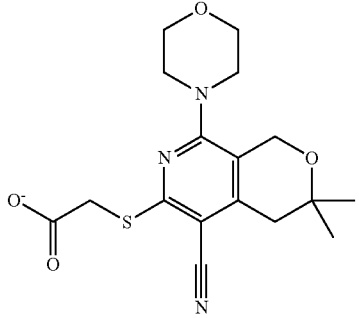

1,2,4-trihydroxyanthracene-9,10-dione, benzimidazole-5,6-dicarboxylic acid, 4-(aminocarbonylamino)benzoic acid, 2-(5-methyl-3-nitropyrazolyl)-N-(4-sulfamoylphenyl)acetamide, N-(1-acetyl-4-oxo-5-hydroimidazo[5,4-d]pyridin-6-yl)acetamide, N-[4-(hydrazinosulfonyl)phenyl]acetamide, 3,5-di(acetylamino)-2-methylbenzoic acid, 2-[(2-hydroxy-tert-butyl)amino]-N-(4-sulfamoylphenyl)acetamide, 2-{[(N-(3-pyridyl)carbamoyl]methyl]cyclopentyl}acetic acid, N-(3-hydroxy(2-pyridyl))[4-(morpholin-4-ylsulfonyl)(2-thienyl)]carboxamide, 4-(benzo[d]furan-2-ylcarbonylamino)benzoic acid, 2-chloro-5-{[N-(3-chlorophenyl)carbamoyl]amino}benzoic acid, 4-[(1-methylpyrazol-3-yl)carbonylamino]benzoic acid, 4-{[5-(methoxymethyl)-2-furyl]carbonylamino}benzoic acid, benzo[d]furan-2-yl-N-(4-sulfamoylphenyl)carboxamide, 3-[N-(4-{[(2,4-dimethylphenyl)amino]sulfonyl}phenyl)carbamoyl]propanoic acid, 3-[N-(4-{[4-(3-carboxypropanoylamino)-3-hydroxyphenyl]methyl}-2-hydroxyphenyl)carbamoyl]propanoic acid, N-benzothiazol-2-yl-3-(phenylsulfonyl)propanamide, 2-benzimidazol-2-ylthioacetohydrazide, N-(4-chlorophenyl) [(4-sulfamoylphenyl)amino]carboxamide, 4-{[N-(3-chlorophenyl)carbamoyl]amino}benzamide, 3-((2E)-3-carboxyprop-2-enoylamino)benzoic acid, N-(3,4-dichlorophenyl) {[4-(N-methylcarbamoyl)phenyl]amino}carboxamide, 2-furyl-N-(4-sulfamoylphenyl)carboxamide, 2-naphthyl-N-(4-sulfamoylphenyl)carboxamide, [1-(methylsulfonyl)indolin-5-yl]-N-(2-pyridyl)carboxamide, N-(3-chlorophenyl)[(6-methoxy(3-pyridyl))amino]carboxamide, 2-(7H-1,2,4-triazolo[4,5-d]1,2,4-triazolin-3-ylthio)-N-(2-pyridyl)acetamide, 2-(2-methoxyphenoxy)-N-

(4-sulfamoylphenyl)acetamide, N-[5-(acetylamino)-2-hydroxy-3-methylphenyl]acetamide, 2-(3-iodo(1,2,4-triazolyl))-N-(3,4,5-trimethoxyphenyl)acetamide, 2-morpholin-4-yl-N-(4-sulfamoylphenyl)acetamide, N-(benzimidazol-2-ylmethyl)-2-(4-hydroxyquinazolin-2-ylthio)acetamide, N-(3-methylphenyl)-2-[9-(4-methylphenyl)-6-oxohydropurin-8-ylthio]acetamide, N-{4-[(naphthylamino)sulfonyl]phenyl}(phenylamino)carboxamide, 2-hydroxy-6-methoxyquinoline-4-carboxylic acid, 4-[N-(4-{N-[(1E)-2-(4-methoxyphenyl)-1-azavinyl]carbamoyl}phenyl)carbamoyl]butanoic acid, 6H,7H-1,4-dioxino[5,6-f]benzimidazol-2-ylmethan-1-ol, N-[(2-fluorophenyl)methyl]{[3-({N-[(2-fluorophenyl)methyl]carbamoyl}amino)phenyl]amino}carboxamide, benzo[d]furan-2-yl-N-(3-ethyl-4-oxo(3-hydroquinazolin-7-yl))carboxamide, 2-(2-oxo(3-hydrobenzoxazol-3-yl))-N-(1,3-thiazol-2-yl)acetamide, N-(2H-benzo[3,4-d]1,3-dioxolan-5-yl)-N'-(2H-benzo[3,4-d]1,3-dioxolen-5-yl)ethane-1,2-diamide, 2H,3H-furano[3,4-e]1,4-dioxane-5,7-dicarboxylic acid, ethyl 11-amino-12-cyano-8-(methoxymethyl)spiro[2H-3,4,5,6-tetrahydropyran-4,7'-4,7-dihydroimidazo[5,4-b]pyridine]-10-carboxylate, 2-(1,3-dimethyl-2,6-dioxo(1,3,7-trihydropurin-7-yl))-N-[5-(trifluoromethyl)(1,3,4-thiadiazol-2-yl)]acetamide, N-benzothiazol-2-yl(3-methyl-4-oxo(3-hydrophthalazinyl))carboxamide, (4-fluorophenyl)-N-(1-oxo(3-hydroisobenzofuran-5-yl))carboxamide, N-(3-fluoro-4-methylphenyl)-2-(6-oxo-9-phenylhydropurin-8-ylthio)acetamide, 2H-benzo[3,4-d]1,3-dioxolen-5-yl-N-(5-ethylthio(1,3,4-thiadiazol-2-yl))carboxamide, 6-(hydrazinecarbonyl)-4-oxo-3,4-dihydrophthalazin-1-olate, 2-(7-amino(1,2,4-triazolo[4,5-d]1,2,4-triazolin-3-ylthio))-N-(5-ethyl(1,3,4-thiadiazol-2-yl))acetamide, 2-amino-5-methyl-4-oxo-5-hydro-1,3-thiazolo[5,4-d]pyridazine-7-carbonitrile, hydro-5H-1,2,3-triazolo[4,5-f]benzotriazole-4,8-dione, N-(2-hydroxyphenyl){3-[N-(2-hydroxyphenyl)carbamoyl]-5-(phenylcarbonylamino)phenyl}carboxamide, N-(2H,3H-benzo[3,4-e]1,4-dioxan-6-yl)-8-hydro-1,2,4-triazolo[1,5-a]pyrimidin-2-ylcarboxamide, 4-hydrazinecarbonyl-3-methylbenzo[4,5-d]pyrido[1,2-a]imidazole-1-olate, N-methyl-2-oxo-1,2-dihydrobenzo[cd]indole-6-sulfonamide, N-(2H,3H-benzo[3,4-e]1,4-dioxin-6-yl)-2-[1-(2-methoxyphenyl)-5,7-dimethyl-2,4-dioxo(1,3-dihydropyridino[2,3-d]pyrimidin-3-yl)]acetamide, 2-amino-5-(2,6-diamino-4-oxo(3-hydropyrimidin-5-yl))-6-(5-chloro(2-thienyl))-3-hydropyrrolo[2,3-d]pyrimidin-4-one, 5-hydroxy-1,3-dimethyl-1,3,8-trihydropyridino[2,3-d]pyrimidine-2,4,7-trione, 6-hydroxy-5-[(6-hydroxy-4-oxo-2-thioxo(1,3-dihydropyrimidin-5-yl))methyl]-2-thioxo-1,3-dihydropyrimidin-4-one, methyl 5-(2-furylcarbonylamino)-3-(methoxycarbonyl)benzoate, 2-{[N-(9,10-dioxoanthryl)carbamoyl]methylthio}acetic acid, 2-(2,4-dibromophenoxy)-N-(4-{[(4-sulfamoylphenyl)amino]sulfonyl}phenyl)acetamide, 1,3-bis(hydroxymethyl)-5-methoxy-3-hydrobenzimidazol-2-one, 10-[(3-chlorophenyl)amino]-2,3-dimethoxy-5,6,7-trihydropyrimidino[6,1-a]isoquinolin-8-one, 2,4-bis(4-hydroxyphenyl)cyclobutane-1,3- and dicarboxylic acid and combinations thereof.

The compounds of some embodiments are selected from:

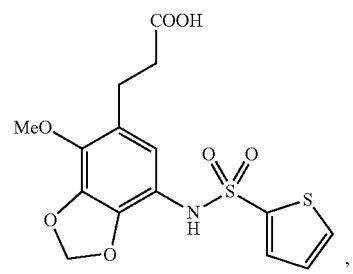
83

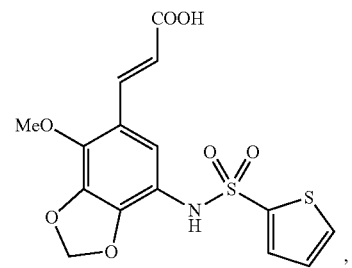
84

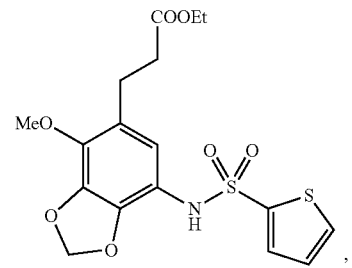
85

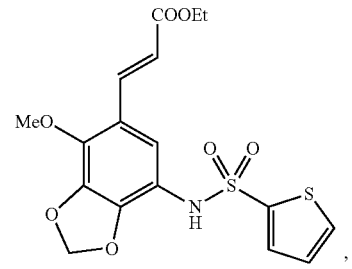
86

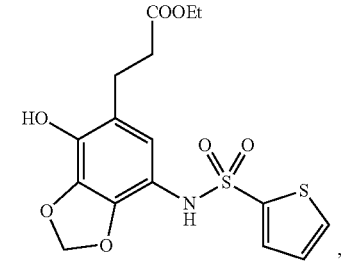
87

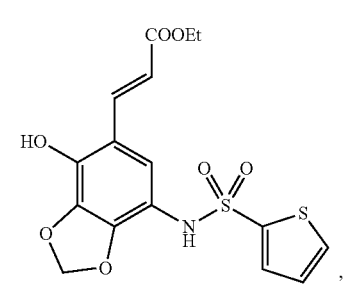
88

89
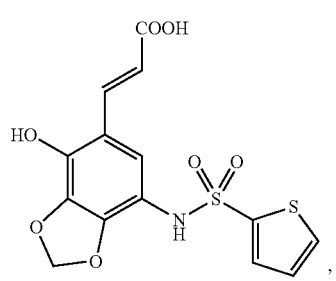
90
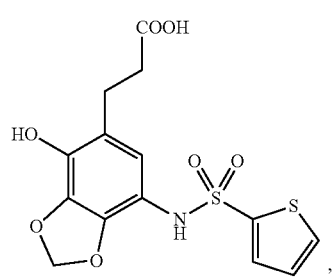
91
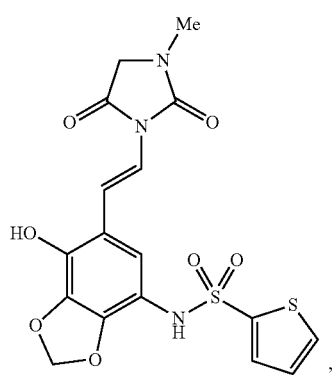
92
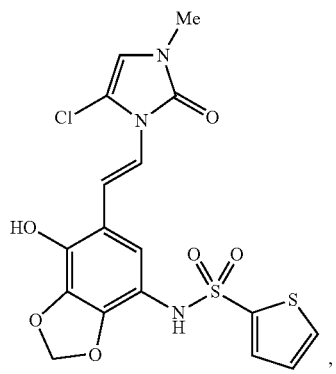
93
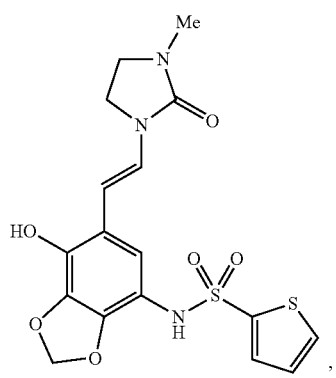
94
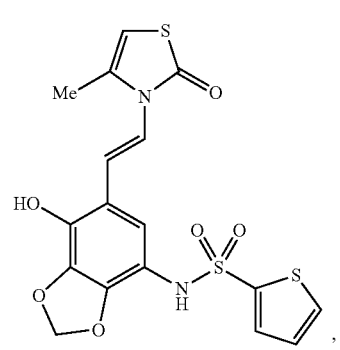
95
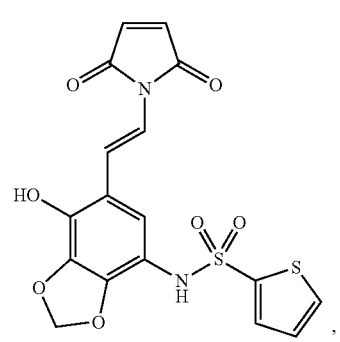
96
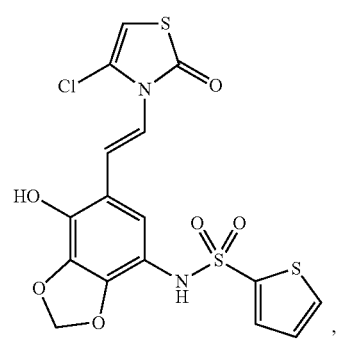
97
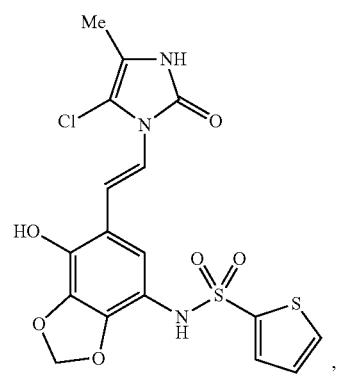

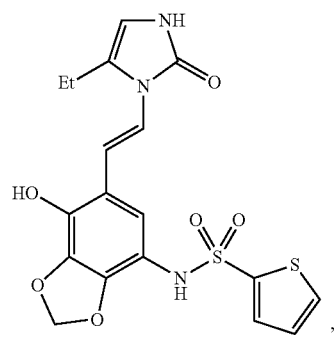
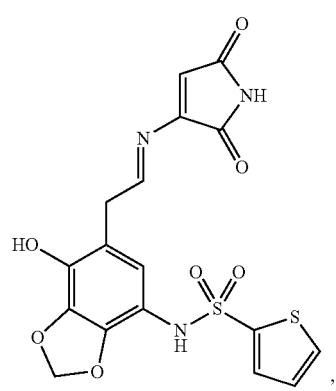
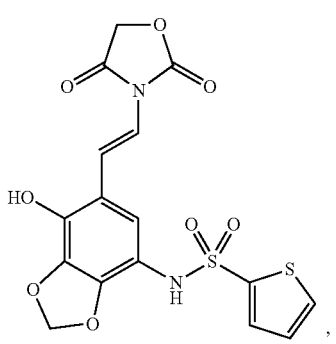
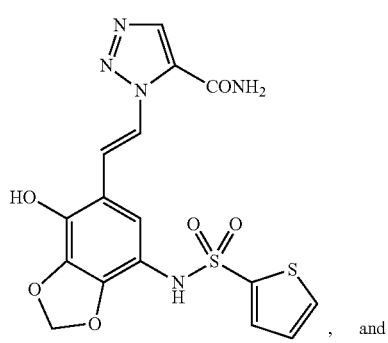
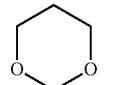
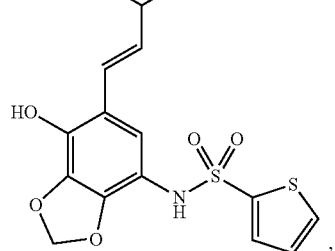
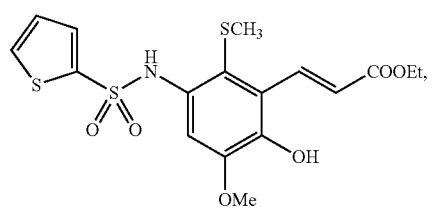
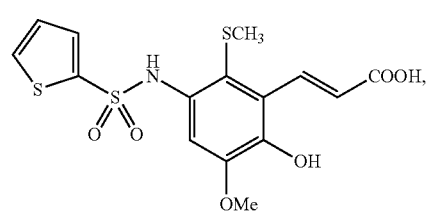
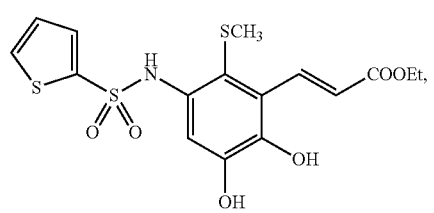
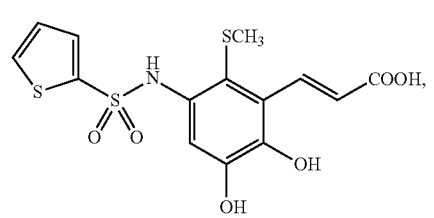
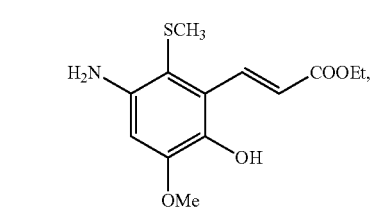
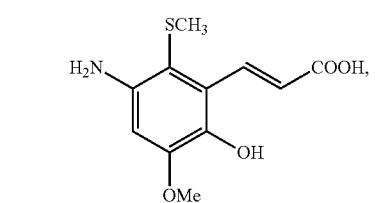

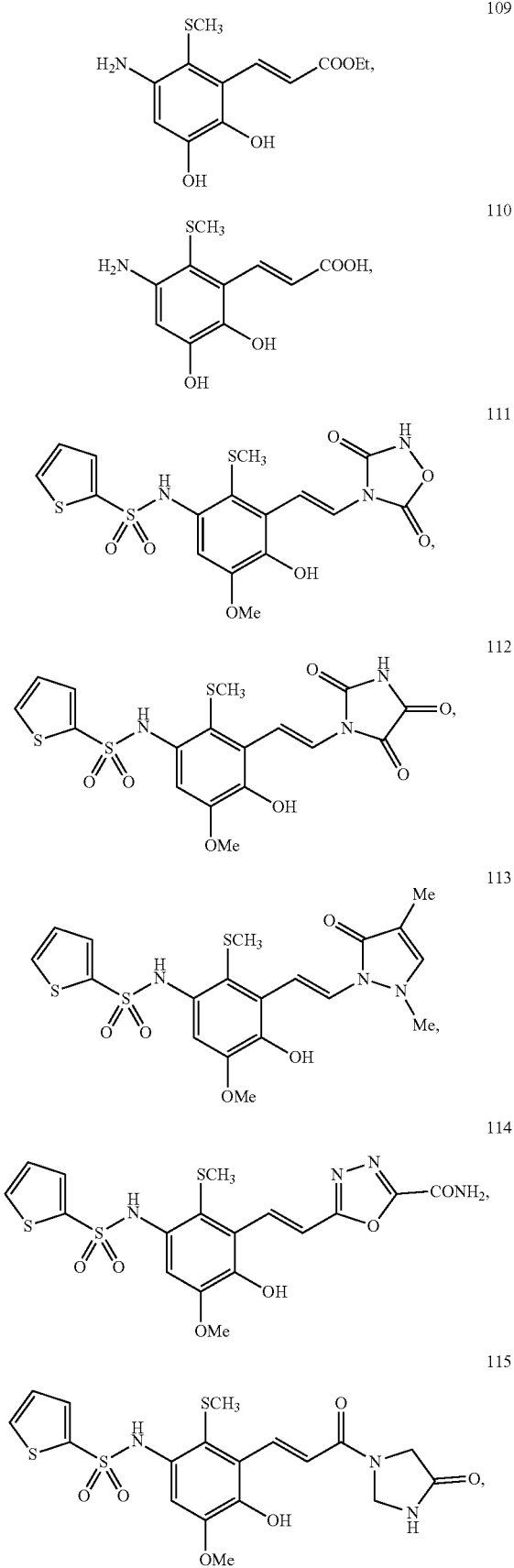
and pharmaceutically acceptable salts thereof

Embodiments are directed toward methods of inhibiting CNKSR1 comprising administering an effective amount of compounds selected from 1-12,
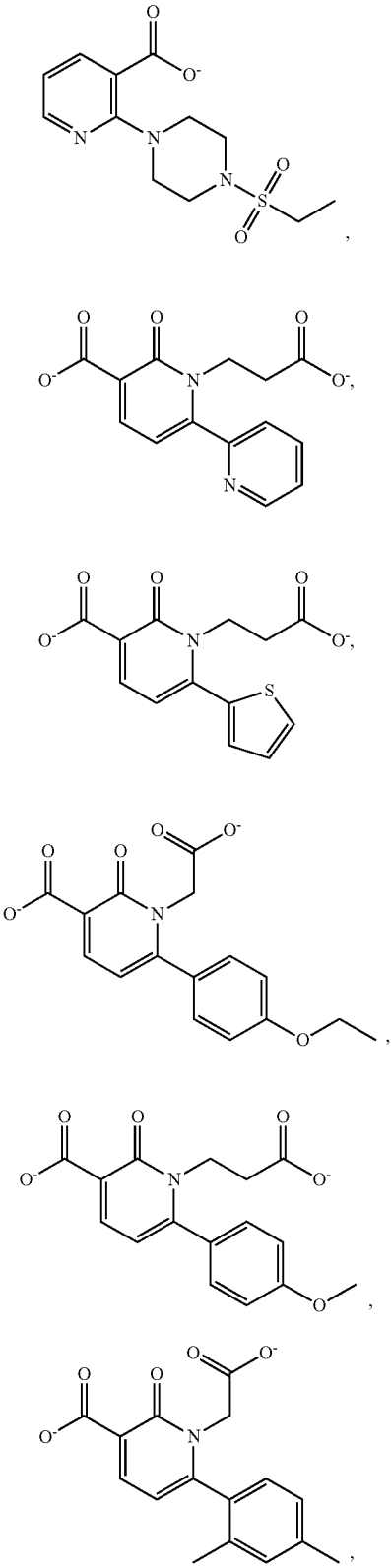
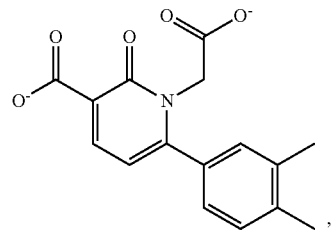
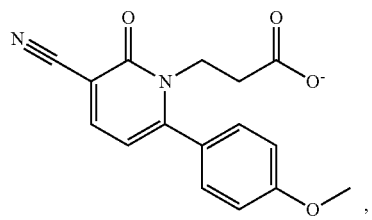
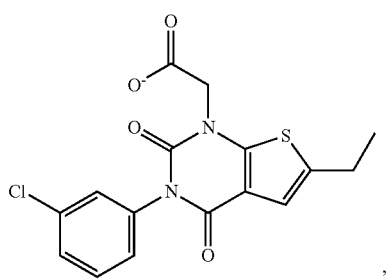
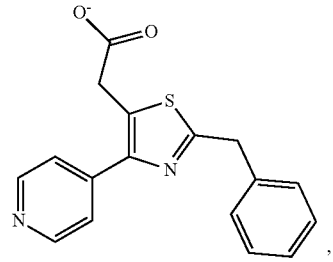
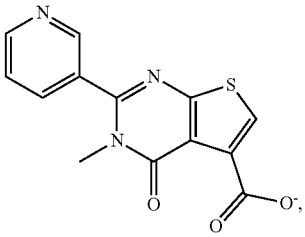
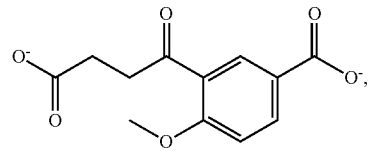
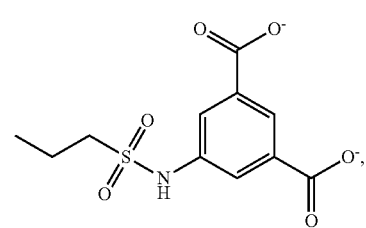

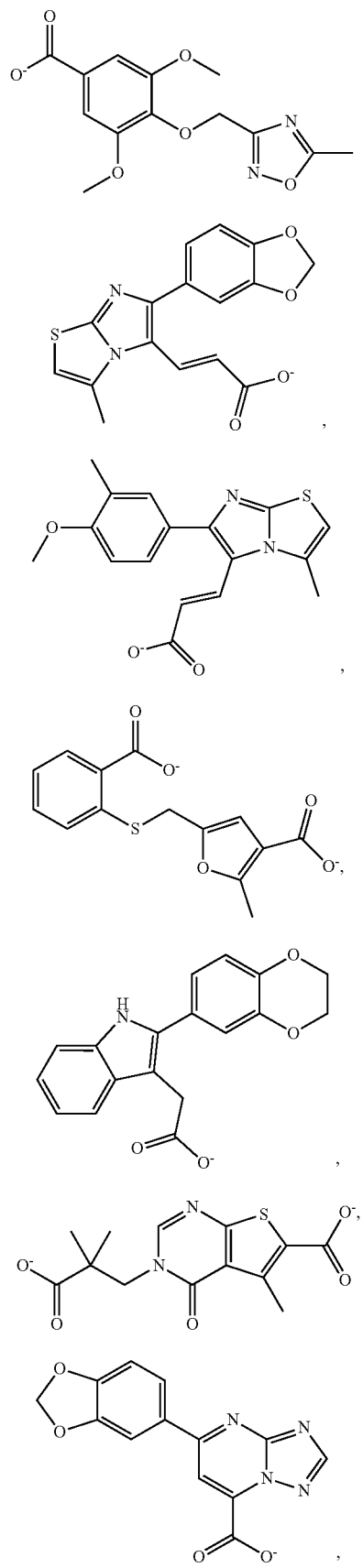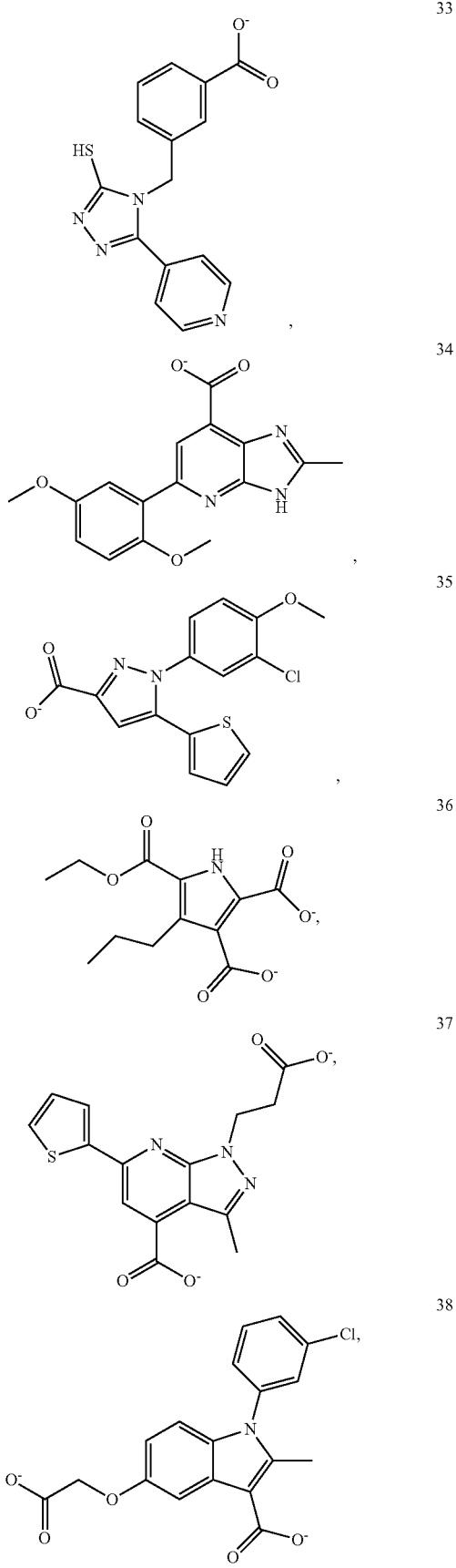

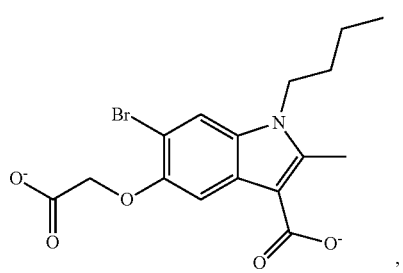
39
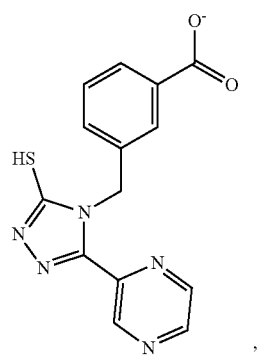
40
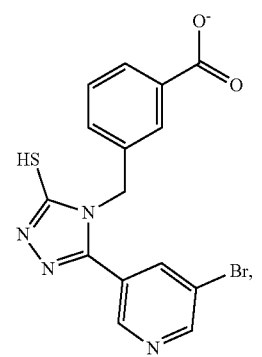
41
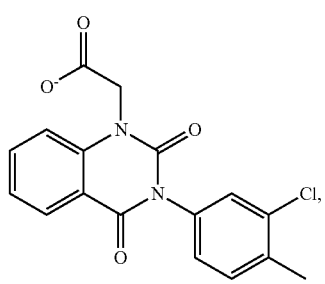
42
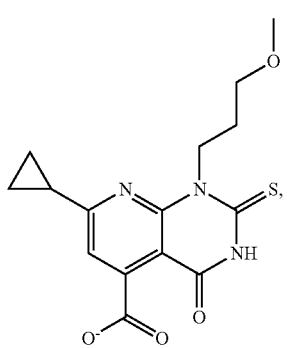
43
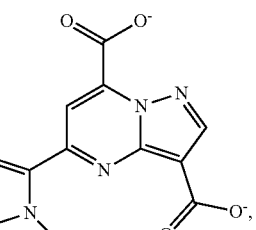
44
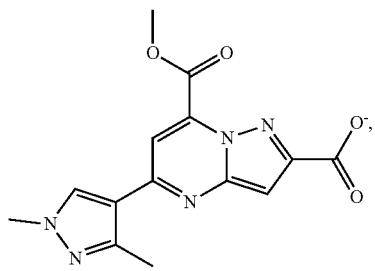
45
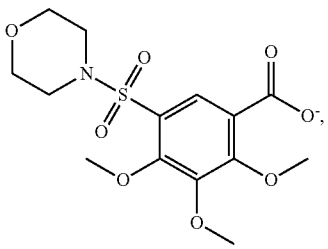
46
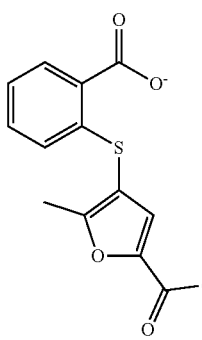
47
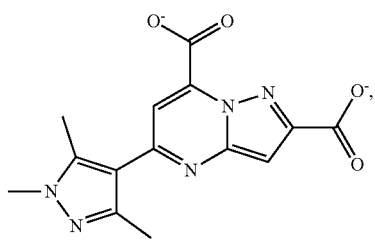
48
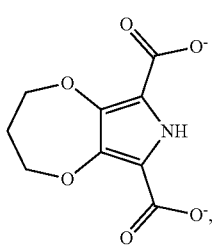
49

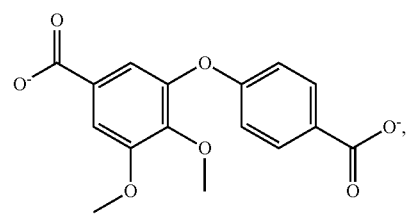
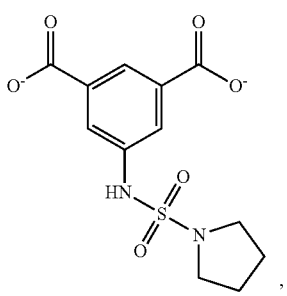
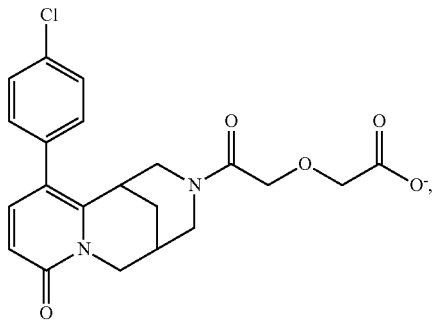
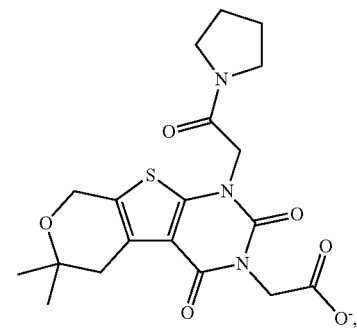
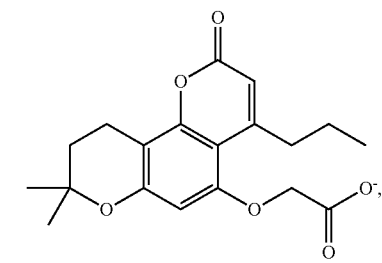
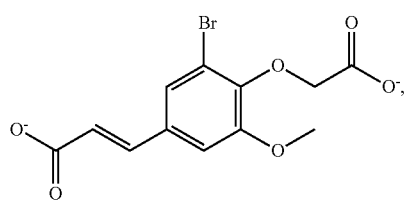
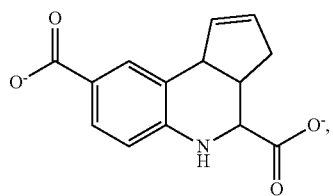
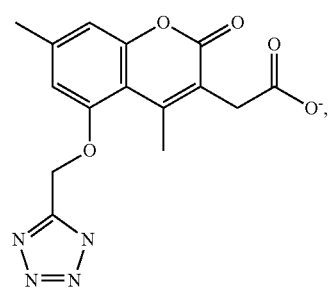
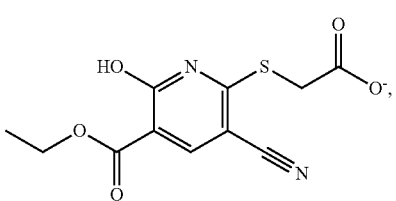
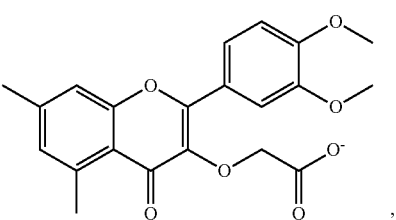
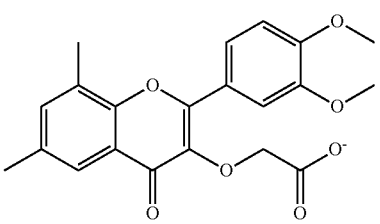
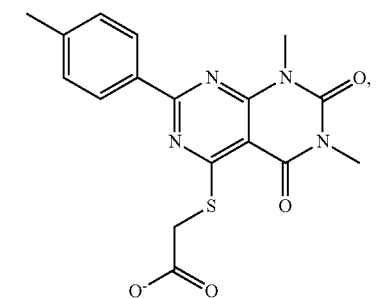

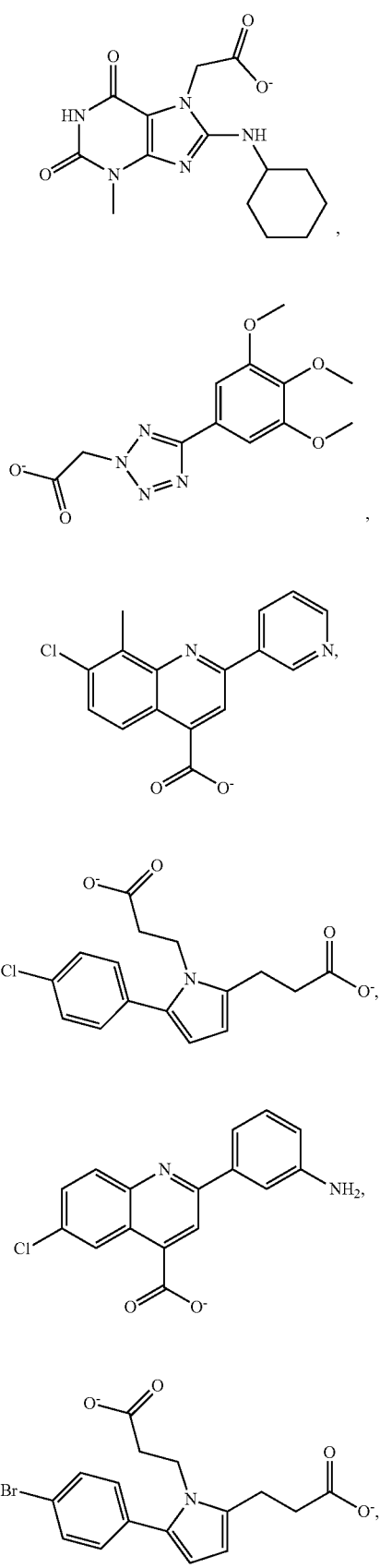
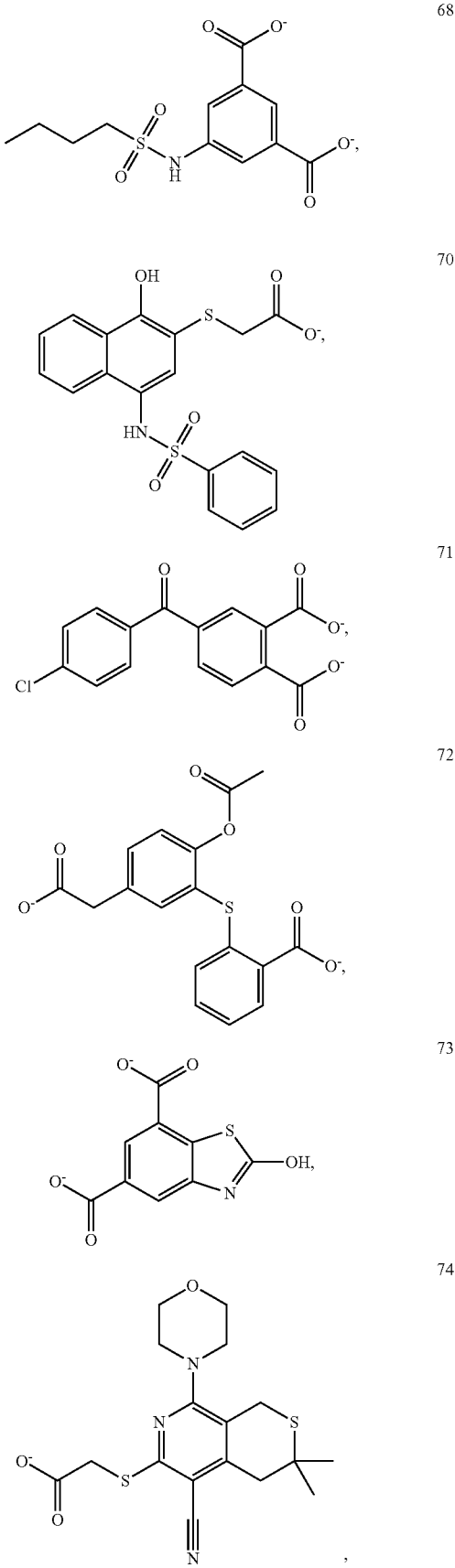

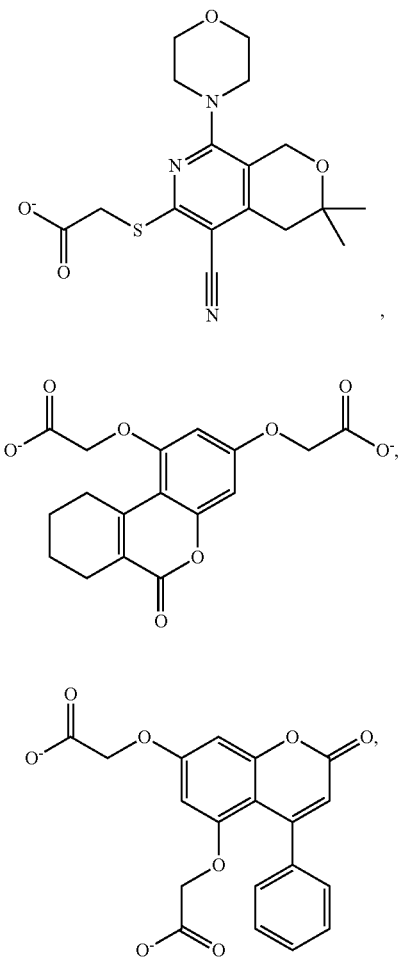

1,2,4-trihydroxyanthracene-9,10-dione, benzimidazole-5,6-dicarboxylic acid, 4-(aminocarbonylamino)benzoic acid, 2-(5-methyl-3-nitropyrazolyl)-N-(4-sulfamoylphenyl)acetamide, N-(1-acetyl-4-oxo-5-hydroimidazo[5,4-d]pyridin-6-yl)acetamide, N-[4-(hydrazinosulfonyl)phenyl]acetamide, 3,5-di(acetylamino)-2-methylbenzoic acid, 2-[(2-hydroxy-tert-butyl)amino]-N-(4-sulfamoylphenyl)acetamide, 2-{[(N-(3-pyridyl)carbamoyl)methyl]cyclopentyl}acetic acid, N-(3-hydroxy(2-pyridyl))[4-(morpholin-4-ylsulfonyl)(2-thienyl)]carboxamide, 4-(benzo[d]furan-2-ylcarbonylamino)benzoic acid, 2-chloro-5-{[N-(3-chlorophenyl)carbamoyl]amino}benzoic acid, 4-[(1-methylpyrazol-3-yl)carbonylamino]benzoic acid, 4-{[5-(methoxymethyl)-2-furyl]carbonylamino}benzoic acid, benzo[d]furan-2-yl-N-(4-sulfamoylphenyl)carboxamide, 3-[N-(4-{[(2,4-dimethylphenyl)amino]sulfonyl}phenyl)carbamoyl]propanoic acid, 3-[N-(4-{[4-(3-carboxypropanoylamino)-3-hydroxyphenyl]methyl}-2-hydroxyphenyl) carbamoyl]propanoic acid, N-benzothiazol-2-yl-3-(phenylsulfonyl)propanamide, 2-benzimidazol-2-ylthioacetohydrazide, N-(4-chlorophenyl) [(4-sulfamoylphenyl)amino]carboxamide, 4-{[N-(3-chlorophenyl)carbamoyl]amino}benzamide, 3-((2E)-3-carboxyprop-2-enoylamino)benzoic acid, N-(3,4-dichlorophenyl) {[4-(N-methylcarbamoyl)phenyl]amino}carboxamide, 2-furyl-N-(4-sulfamoylphenyl)carboxamide, 2-naphthyl-N-(4-sulfamoylphenyl)carboxamide, [1-(methylsulfonyl)indolin-5-yl]-N-(2-pyridyl)carboxamide, N-(3-chlorophenyl)[(6-methoxy(3-pyridyl))amino]carboxamide, 2-(7H-1,2,4-triazolo[4,5-d]1,2,4-triazolin-3-ylthio)-N-(2-pyridyl)acetamide, 2-(2-methoxyphenoxy)-N-(4-sulfamoylphenyl)acetamide, N-[5-(acetylamino)-2-hydroxy-3-methylphenyl]acetamide, 2-(3-iodo(1,2,4-triazolyl))-N-(3,4,5-trimethoxyphenyl)acetamide, 2-morpholin-4-yl-N-(4-sulfamoylphenyl)acetamide, N-(benzimidazol-2-ylmethyl)-2-(4-hydroxyquinazolin-2-ylthio)acetamide, N-(3-methylphenyl)-2-[9-(4-methylphenyl)-6-oxohydropurin-8-ylthio]acetamide, N-{4-[(naphthylamino)sulfonyl]phenyl}(phenylamino)carboxamide, 2-hydroxy-6-methoxyquinoline-4-carboxylic acid, 4-[N-(4-{N-[(1E)-2-(4-methoxyphenyl)-1-azavinyl]carbamoyl}phenyl)carbamoyl]butanoic acid, 6H,7H-1,4-dioxino[5,6-f]benzimidazol-2-ylmethan-1-ol, N-[(2-fluorophenyl)methyl]{[3-({N-[(2-fluorophenyl)methyl]carbamoyl}amino)phenyl]amino}carboxamide, benzo[d]furan-2-yl-N-(3-ethyl-4-oxo(3-hydroquinazolin-7-yl)) carboxamide, 2-(2-oxo(3-hydrobenzoxazol-3-yl))-N-(1,3-thiazol-2-yl)acetamide, N-(2H-benzo[3,4-d]1,3-dioxolan-5-yl)-N'-(2H-benzo[3,4-d]1,3-dioxolen-5-yl)ethane-1,2-diamide, 2H,3H-furano[3,4-e]1,4-dioxane-5,7-dicarboxylic acid, ethyl 11-amino-12-cyano-8-(methoxymethyl)spiro[2H-3,4,5,6-tetrahydropyran-4,7'-4,7-dihydroimidazo[5,4-b]pyridine]-10-carboxylate, 2-(1,3-dimethyl-2,6-dioxo(1,3,7-trihydropurin-7-yl))-N-[5-(trifluoromethyl)(1,3,4-thiadiazol-2-yl)]acetamide, N-benzothiazol-2-yl(3-methyl-4-oxo(3-hydrophthalazinyl))carboxamide, (4-fluorophenyl)-N-(1-oxo(3-hydroisobenzofuran-5-yl))carboxamide, N-(3-fluoro-4-methylphenyl)-2-(6-oxo-9-phenylhydropurin-8-ylthio)acetamide, 2H-benzo[3,4-d]1,3-dioxolen-5-yl-N-(5-ethylthio(1,3,4-thiadiazol-2-yl))carboxamide, 6-(hydrazinecarbonyl)-4-oxo-3,4-dihydrophthalazin-1-olate, 2-(7-amino(1,2,4-triazolo[4,5-d]1,2,4-triazolin-3-ylthio))-N-(5-ethyl(1,3,4-thiadiazol-2-yl))acetamide, 2-amino-5-methyl-4-oxo-5-hydro-1,3-thiazolo[5,4-d]pyridazine-7-carbonitrile, hydro-5H-1,2,3-triazolo[4,5-f]benzotriazole-4,8-dione, N-(2-hydroxyphenyl) {3-[N-(2-hydroxyphenyl)carbamoyl]-5-(phenylcarbonylamino)phenyl}carboxamide, N-(2H,3H-benzo[3,4-e]1,4-dioxan-6-yl)-8-hydro-1,2,4-triazolo[1,5-a]pyrimidin-2-ylcarboxamide, 4-hydrazinecarbonyl-3-methylbenzo[4,5-d]pyrido[1,2-a]imidazole-1-olate, N-methyl-2-oxo-1,2-dihydrobenzo[cd]indole-6-sulfonamide, N-(2H,3H-benzo[3,4-e]1,4-dioxin-6-yl)-2-[1-(2-methoxyphenyl)-5,7-dimethyl-2,4-dioxo(1,3-dihydropyridino[2,3-d]pyrimidin-3-yl)]acetamide, 2-amino-5-(2,6-diamino-4-oxo(3-hydropyrimidin-5-yl))-6-(5-chloro(2-thienyl))-3-hydropyrrolo[2,3-d]pyrimidin-4-one, 5-hydroxy-1,3-dimethyl-1,3,8-trihydropyridino[2,3-d]pyrimidine-2,4,7-trione, 6-hydroxy-5-[(6-hydroxy-4-oxo-2-thioxo(1,3-dihydropyrimidin-5-yl))methyl]-2-thioxo-1,3-dihydropyrimidin-4-one, methyl 5-(2-furylcarbonylamino)-3-(methoxycarbonyl)benzoate, 2-{[N-(9,10-dioxoanthryl)carbamoyl]methylthio}acetic acid, 2-(2,4-dibromophenoxy)-N-(4-{[(4-sulfamoylphenyl)amino]sulfonyl}phenyl)acetamide, 1,3-bis(hydroxymethyl)-5-methoxy-3-hydrobenzimidazol-2-one, 10-[(3-chlorophenyl)amino]-2,3-dimethoxy-5,6,7-trihydropyrimidino[6,1-a]isoquinolin-8-one, 2,4-bis(4-hydroxyphenyl)cyclobutane-1,3- and dicarboxylic acid and combinations thereof.

Embodiments are directed toward methods of inhibiting CNKSR1 comprising administering an effective amount of compounds selected from

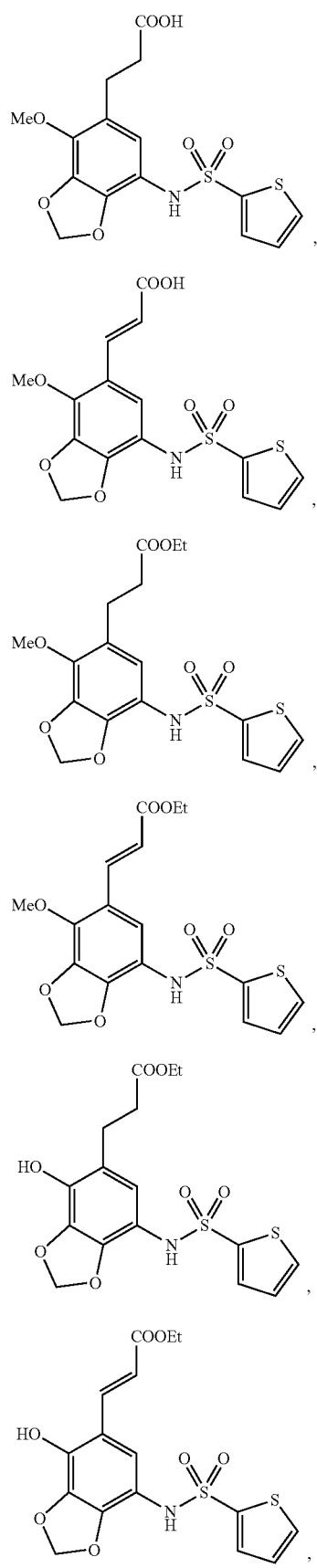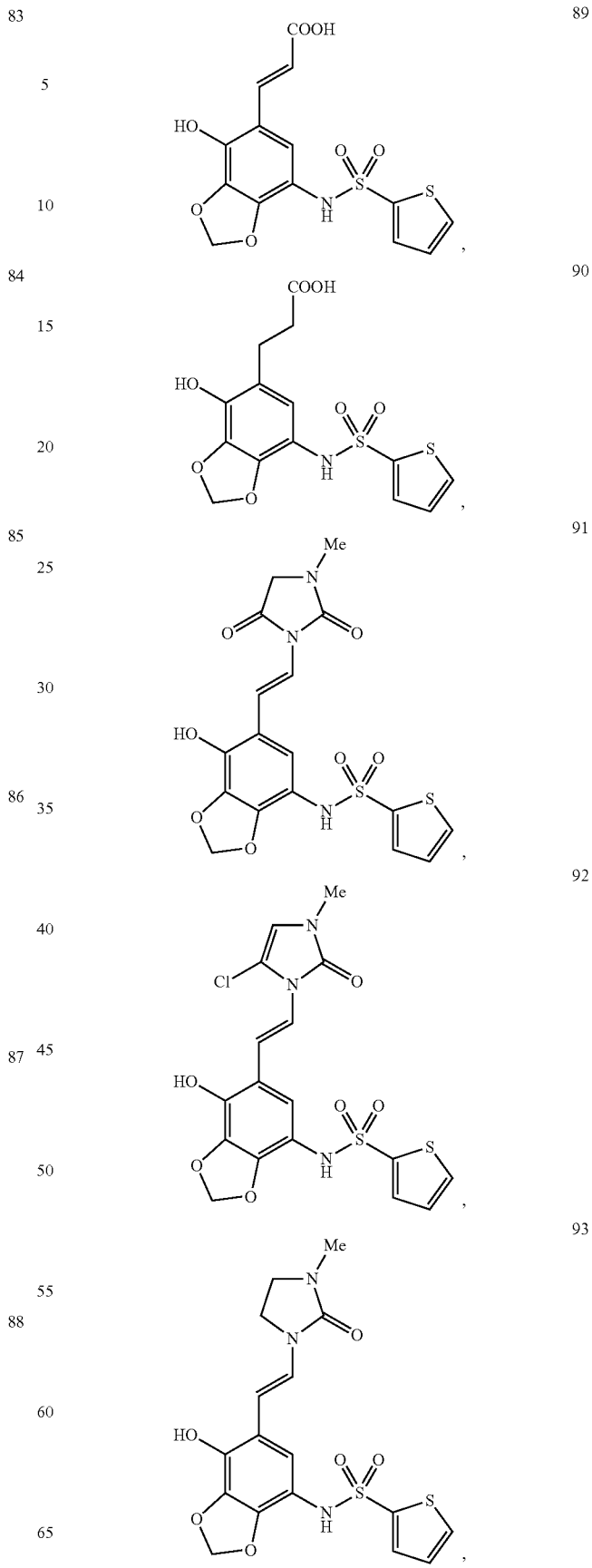

94 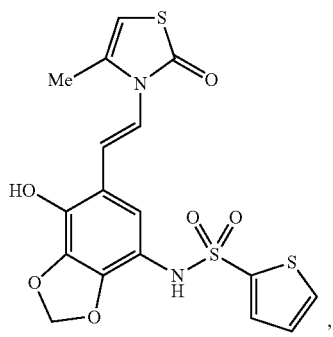,
95 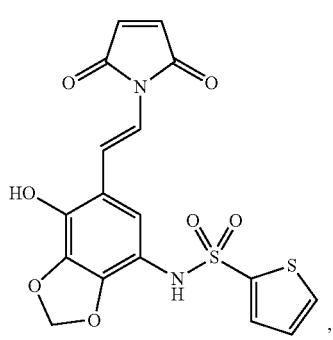,
96 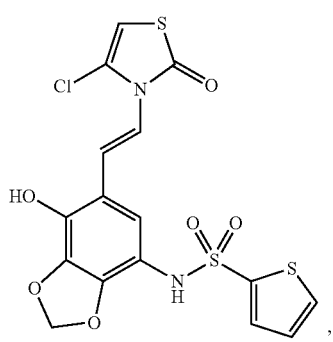,
97 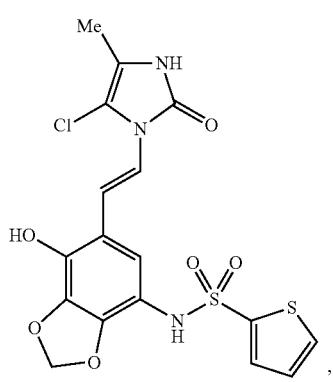,
98 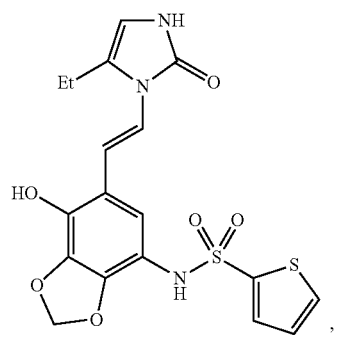,
99 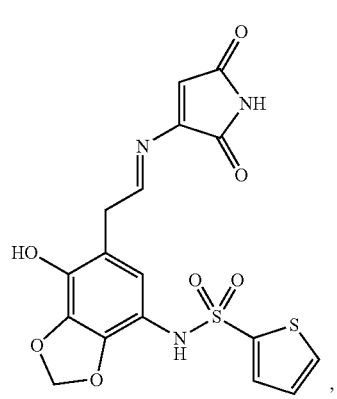,
100 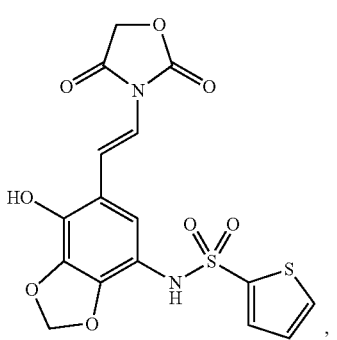,
101 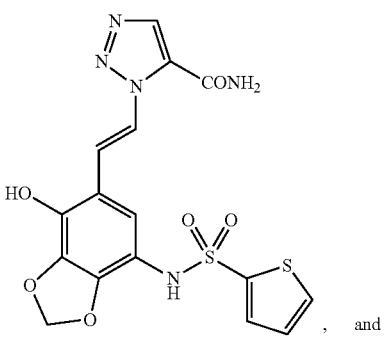, and

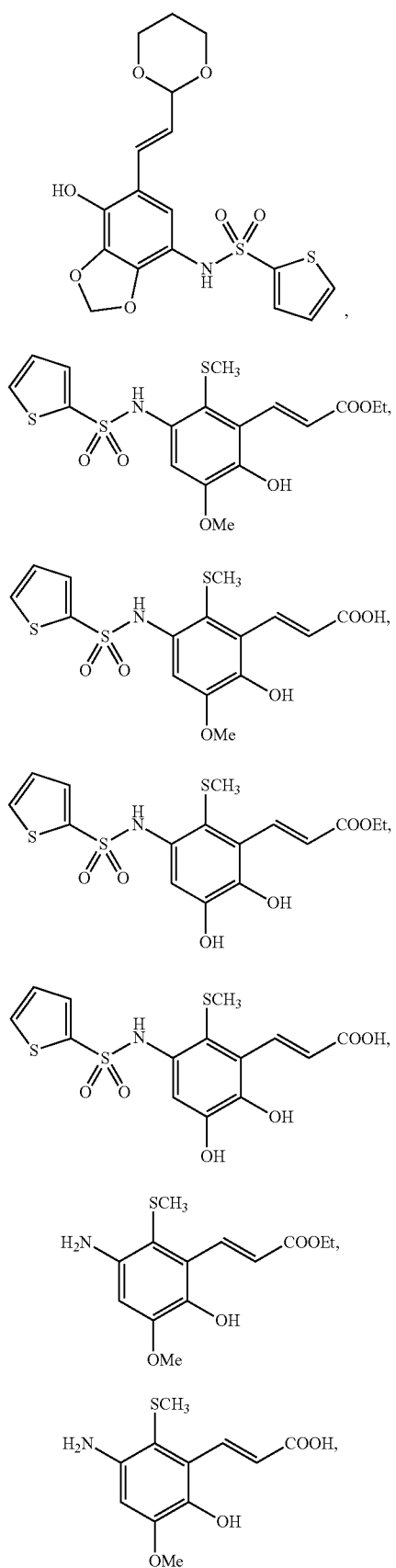
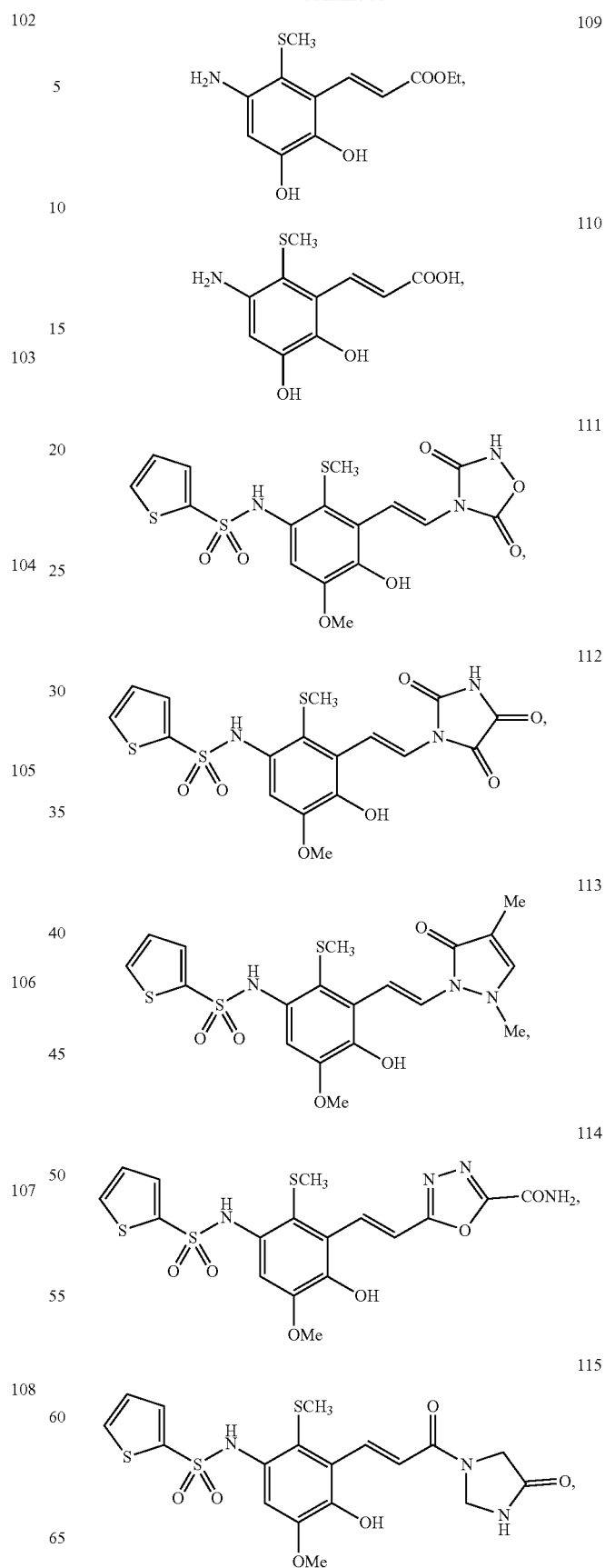

-continued

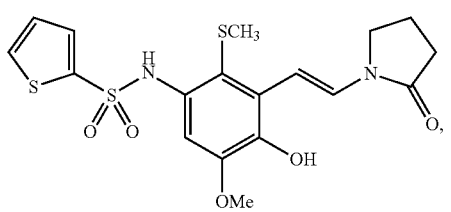
116

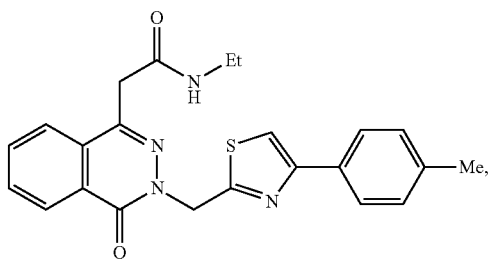
78

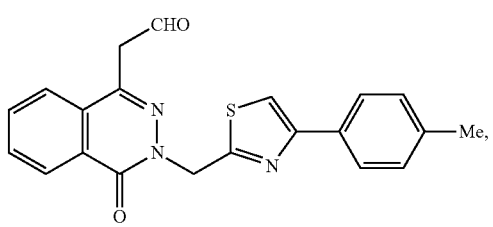
79

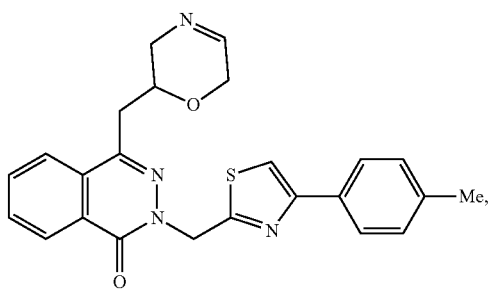
80

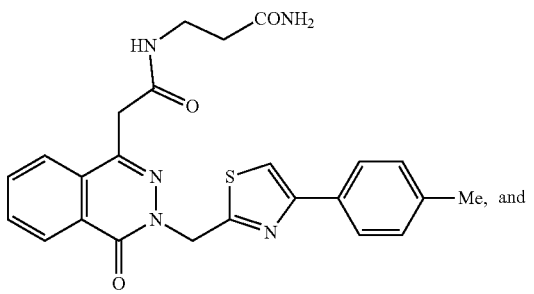
81

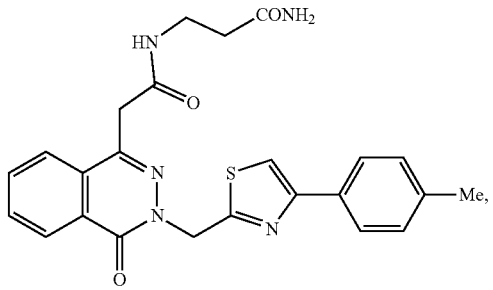
82 and pharmaceutically acceptable salts thereof

In embodiments, the treatment of cancer or the inhibition of CNKSR1 does not inhibit wild-type KRAS cancer cell growth In embodiments, the treatment of cancer or the inhibition of CNKSR1 may further comprising administering an anti-cancer agent, radiation, phototherapy, or a combination thereof. Anti-cancer agents may be selected from alkylating agents, antimetabolites, anthracyclines, plant alkaloids, topoisomerase inhibitors, monoclonal antibodies, tyrosine kinase inhibitors, and hormone treatment.

Embodiments are directed toward methods of identifying compounds that inhibit the activity of CNKSR1 comprising: contacting CNKSR1 with a test compound; determining the activity of CNKSR1 in the presence of the test compound; and identifying the test compound as a compound that inhibits the activity of CNKSR1 if the activity of CNKSR1 is decreased in the presence of the test compound. Such embodiments may further comprise determining the activity of CNKSR1 in the absence of the test compound. Identifying the test compound as a compound that inhibits the activity of CNKSR1 may further comprise comparing the activity of CNKSR1 in the presence and the absence of the test compound, wherein the compound is identified as a compound that inhibits the activity of CNKSR1 if the activity of CNKSR1 is decreased in the presence of the test compound as compared to the activity of CNKSR1 in the absence of the test compound.

In embodiments of the invention, cancer may include, but is not limited to, adrenocortical carcinoma, anal cancer, bladder cancer, brain tumor, breast cancer, carcinoid tumor, gastrointestinal, carcinoma of unknown primary, cervical cancer, colon cancer, endometrial cancer, esophageal cancer, extrahepatic bile duct cancer, Ewings family of tumors (PNET), extracranial germ cell tumor, eye cancer, intraocular melanoma, gallbladder cancer, gastric cancer (stomach), germ cell tumor, extragonadal, gestational trophoblastic tumor, head and neck cancer, hypopharyngeal cancer, islet cell carcinoma, kidney cancer, laryngeal cancer, leukemia, acute lymphoblastic, adult, leukemia, acute lymphoblastic, childhood, leukemia, lip and oral cavity cancer, liver cancer, lung cancer, lymphoma, aids-related, lymphoma, central nervous system (primary), lymphoma, cutaneous T-cell, lymphoma, hodgkin's disease, adult, lymphoma, hodgkin's disease, childhood, lymphoma, non-hodgkin's disease, adult, lymphoma, non-hodgkin's disease, childhood, malignant mesothelioma, melanoma, merkel cell carcinoma, metasatic squamous neck cancer with occult primary, multiple myeloma and other plasma cell neoplasms, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, exocrine, pancreatic cancer, islet cell carcinoma, paranasal sinus and nasal cavity cancer, parathyroid cancer, penile cancer, pituitary cancer, plasma cell neoplasm, prostate cancer, rhabdomyosarcoma, childhood, rectal cancer, renal cell cancer, renal pelvis and ureter, transitional cell, salivary gland cancer, sezary syndrome, skin cancer, skin cancer, cutaneous T-cell lymphoma, skin cancer, kaposi's sarcoma, skin cancer, melanoma, small intestine cancer, soft tissue sarcoma, adult, soft tissue sarcoma, child, stomach cancer, testicular cancer, thymoma, malignant, thyroid cancer, urethral cancer, uterine cancer, sarcoma, unusual cancer of childhood, vaginal cancer, vulvar cancer, Wilms' Tumor and combinations thereof. In certain embodiments, the cancer is selected from colon, lung, pancreas or combinations thereof.

For example, in some aspects, the invention is directed to a pharmaceutical composition comprising a compound, as defined above, and a pharmaceutically acceptable carrier or diluent, or an effective amount of a pharmaceutical composition comprising a compound as defined above.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the compounds of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

As used herein, the term "alginic acid" refers to a naturally occurring hydrophilic colloidal polysaccharide obtained from the various species of seaweed, or synthetically modified polysaccharides thereof.

As used herein, the term "sodium alginate" refers to a sodium salt of alginic acid and can be formed by reaction of alginic acid with a sodium containing base such as sodium hydroxide or sodium carbonate. As used herein, the term "potassium alginate" refers to a potassium salt of alginic acid and can be formed by reaction of alginic acid with a potassium containing base such as potassium hydroxide or potassium carbonate. As used herein, the term "calcium alginate" refers to a calcium salt of alginic acid and can be formed by reaction of alginic acid with a calcium containing base such as calcium hydroxide or calcium carbonate. Suitable sodium alginates, calcium alginates, and potassium alginates include, but are not limited to, those described in R. C. Rowe and P. J. Shesky, Handbook of pharmaceutical excipients, (2006), 5th ed., which is incorporated herein by reference in its entirety. Suitable sodium alginates, include, but are not limited to, Kelcosol (available from ISP), Kelfone LVCR and HVCR (available from ISP), Manucol (available from ISP), and Protanol (available from FMC Biopolymer).

As used herein, the term "calcium silicate" refers to a silicate salt of calcium.

As used herein, the term "calcium phosphate" refers to monobasic calcium phosophate, dibasic calcium phosphate or tribasic calcium phosphate.

Cellulose, cellulose floc, powdered cellulose, microcrystalline cellulose, silicified microcrystalline cellulose, carboxyethylcellulose, carboxymethylcellulose, hydroxyethylcellulose, methylhydroxyethylcellulose, hydroxymethylcellulose, hydroxypropylcellulose, hydroxypropylmethylcellulose, hydroxypropylmethylcellulose phthalate, ethylcellulose, methylcellulose, carboxymethylcellulose sodium, and carboxymethyl cellulose calcium include, but are not limited to, those described in R. C. Rowe and P. J. Shesky, Handbook of pharmaceutical excipients, (2006), 5th ed., which is incorporated herein by reference in its entirety. As used herein, cellulose refers to natural cellulose. The term "cellulose" also refers to celluloses that have been modified with regard to molecular weight and/or branching, particularly to lower molecular weight. The term "cellulose" further refers to celluloses that have been chemically modified to attach chemical functionality such as carboxy, hydroxyl, hydroxyalkylene, or carboxyalkylene groups. As used herein, the term "carboxyalkylene" refers to a group of formula -alkylene-C(O)OH, or salt thereof. As used herein, the term "hydroxyalkylene" refers to a group of formula -alkylene-OH.

Suitable powdered celluloses for use in the invention include, but are not limited to Arbocel (available from JRS Pharma), Sanacel (available from CFF GmbH), and Solka-Floc (available from International Fiber Corp.).

Suitable microcrystalline celluloses include, but are not limited to, the Avicel pH series (available from FMC Biopolymer), Celex (available from ISP), Celphere (available from Asahi Kasei), Ceolus KG (available from Asahi Kasei), and Vivapur (available from JRS Pharma).

As used herein, the term "silicified microcrystalline cellulose" refers to a synergistic intimate physical mixture of silicon dioxide and microcrystalline cellulose. Suitable silicified microcrystalline celluloses include, but are not limited to, ProSolv (available from JRS Pharma).

As used herein, the term "carboxymethylcellulose sodium" refers to a cellulose ether with pendant groups of formula $Na^+$—O—C(O)—$CH_2$—, attached to the cellulose via an ether linkage. Suitable carboxymethylcellulose sodium polymers include, but are not limited to, Akucell (available from Akzo Nobel), Aquasorb (available from Hercules), Blanose (available from Hercules), Finnfix (available from Noviant), Nymel (available from Noviant), and Tylose CB (available from Clariant).

As used herein, the term "carboxymethylcellulose calcium" refers to a cellulose ether with a pendant groups of formula —$CH_2$—O—C(O)—$O^-\frac{1}{2}Ca^{2+}$, attached to the cellulose via an ether linkage.

As used herein, the term "carboxymethylcellulose" refers to a cellulose ether with pendant carboxymethyl groups of formula HO—C(O)—$CH_2$—, attached to the cellulose via an ether linkage. Suitable carboxymethylcellulose calcium polymers include, but are not limited to, Nymel ZSC (available from Noviant).

As used herein, the term "carboxyethylcellulose" refers to a cellulose ether with pendant carboxymethyl groups of formula HO—C(O)—$CH_2$—$CH_2$—, attached to the cellulose via an ether linkage.

As used herein, the term "hydroxyethylcellulose" refers to a cellulose ether with pendant hydroxyethyl groups of formula HO—CH$_2$—CH$_2$—, attached to the cellulose via an ether linkage. Suitable hydroxyethylcelluloses include, but are not limited to, Cellosize HEC (available from DOW), Natrosol (available from Hercules), and Tylose PHA (available from Clariant).

As used herein, the term "methylhydroxyethylcellulose" refers to a cellulose ether with pendant methyloxyethyl groups of formula CH$_3$—O—CH$_2$—CH$_2$—, attached to the cellulose via an ether linkage. Suitable methylhydroxyethylcelluloses include, but are not limited to, the Culminal MHEC series (available from Hercules), and the Tylose series (available from Shin Etsu).

As used herein, the term "hydroxypropylcellulose", or "hypomellose", refers a cellulose that has pendant hydroxypropoxy groups, and includes both high- and low-substituted hydroxypropylcellulose. In some embodiments, the hydroxypropylcellulose has about 5% to about 25% hydroxypropyl groups. Suitable hydroxypropylcelluloses include, but are not limited to, the Klucel series (available from Hercules), the Methocel series (available from Dow), the Nisso HPC series (available from Nisso), the Metolose series (available from Shin Etsu), and the LH series, including LHR-11, LH-21, LH-31, LH-20, LH-30, LH-22, and LH-32 (available from Shin Etsu).

As used herein, the term "methyl cellulose" refers to a cellulose that has pendant methoxy groups. Suitable methyl celluloses include, but are not limited to Culminal MC (available from Hercules).

As used herein, the term "ethyl cellulose" refers to a cellulose that has pendant ethoxy groups. Suitable ethyl celluloses include, but are not limited to Aqualon (available from Hercules).

As used herein, the term "carmellose calcium" refers to a crosslinked polymer of carboxymethylcellulose calcium.

As used herein, the term "croscarmellose sodium" refers to a crosslinked polymer of carboxymethylcellulose sodium.

As used herein, the term "crospovidone" refers to a crosslinked polymer of polyvinylpyrrolidone. Suitable crospovidone polymers include, but are not limited to Polyplasdone XL-10 (available from ISP) and Kollidon CL and CL-M (available from BASF).

As used herein, the term "crosslinked poly(acrylic acid)" refers to a polymer of acrylic acid which has been crosslinked. The crosslinked polymer may contain other monomers in addition to acrylic acid. Additionally, the pendant carboxy groups on the crosslinked polymer may be partially or completely neutralized to form a pharmaceutically acceptable salt of the polymer. In some embodiments, the crosslinked poly(acrylic acid) is neutralized by ammonia or sodium hydroxide. Suitable crosslinked poly(acrylic acid) polymers include, but are not limited to, the Carbopol series (available from Noveon).

As used herein, the term "an effervescent system based on food acids and an alkaline carbonate component" refers to a excipient combination of food acids and alkaline carbonates that releases carbon dioxide gas when administered. Suitable effervescent systems are those that those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.).

As used herein, the term "fatty acid", employed alone or in combination with other terms, refers to an aliphatic acid that is saturated or unsaturated. In some embodiments, the fatty acid in a mixture of different fatty acids. In some embodiments, the fatty acid has between about eight to about thirty carbons on average. In some embodiments, the fatty acid has about eight to about twenty-four carbons on average. In some embodiments, the fatty acid has about twelve to about eighteen carbons on average. Suitable fatty acids include, but are not limited to, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, and arachidonic acid, or mixtures thereof.

As used herein, the term "fatty acid ester" refers to a compound formed between a fatty acid and a hydroxyl containing compound. In some embodiments, the fatty acid ester is a sugar ester of fatty acid. In some embodiments, the fatty acid ester is a glyceride of fatty acid. In some embodiments, the fatty acid ester is an ethoxylated fatty acid ester.

As used herein, the term "fatty alcohol", employed alone or in combination with other terms, refers to an aliphatic alcohol that is saturated or unsaturated. In some embodiments, the fatty alcohol in a mixture of different fatty alcohols. In some embodiments, the fatty alcohol has between about eight to about thirty carbons on average. In some embodiments, the fatty alcohol has about eight to about twenty-four carbons on average. In some embodiments, the fatty alcohol has about twelve to about eighteen carbons on average. Suitable fatty alcohols include, but are not limited to, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol, or mixtures thereof.

As used herein, the term "ion-exchange resin" refers to an ion-exchange resin that is pharmaceutically acceptable and that can be weakly acidic, weakly basic, strongly acidic or strongly basic. Suitable ion-exchange resins include, but are not limited to Amberlite™ IRP64, IRP88 and IRP69 (available from Rohm and Haas) and Duolite™ AP143 (available from Rohm and Haas). In some embodiments, the ion-exchange resin is a crosslinked polymer resin comprising acrylic acid, methacrylic acid, or polystyrene sulfonate, or salts thereof. In some embodiments, the ion-exchange resin is polacrilex resin, polacrilin potassium resin, or cholestyramine resin.

Suitable mannitols include, but are not limited to, Pharm-Mannidex (available from Cargill), Pearlitol (available from Roquette), and Mannogem (available from SPI Polyols).

As used herein, the term "metal aluminosilicate" refers to any metal salt of an aluminosilicate, including, but not limited to, magnesium aluminometasilicate. Suitable magnesium aluminosilicates include, but are not limited to Neusilin (available from Fuji Chemical), Pharmsorb (available from Engelhard), and Veegum (available from R.T. Vanderbilt Co., Inc.). In some embodiments, the metal aluminosilicate is bentonite.

As used herein, the term "metal carbonate" refers to any metallic carbonate, including, but not limited to sodium carbonate, calcium carbonate, and magnesium carbonate, and zinc carbonate.

As used herein, the term "metal oxide" refers to any metallic oxide, including, but not limited to, calcium oxide or magnesium oxide.

As used herein, the term "metallic stearate" refers to a metal salt of stearic acid. In some embodiments, the metallic stearate is calcium stearate, zinc stearate, or magnesium stearate. In some embodiments, the metallic stearate is magnesium stearate.

As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

As used herein, the term "polyethoxylated castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, Handbook of pharmaceutical excipients, (2006), 5th ed., which is incorporated herein by reference in its entirety.

As used herein, the term "polyethoxylated sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

As used herein, the term "polyethoxylated vegetable oil" refers to a compound, or mixture of compounds, formed from ethoxylation of vegetable oil, wherein at least one chain of polyethylene glycol is covalently bound to the the vegetable oil. In some embodiments, the fatty acids has between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

As used herein, the term "polyethylene glycol" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

As used herein, the term "polyoxyethylene-alkyl ether" refers to a monoalkyl or dialkylether of polyoxyethylene, or mixtures thereof. In some embodiments, the polyoxyethylene-alkyl ether is a polyoxyethylene fatty alcohol ether.

As used herein, the term "polyoxyethylene fatty alcohol ether" refers to an monoether or diether, or mixtures thereof, formed between polyethylene glycol and a fatty alcohol. Fatty alcohols that are useful for deriving polyoxyethylene fatty alcohol ethers include, but are not limited to, those defined herein. In some embodiments, the polyoxyethylene portion of the molecule has about 2 to about 200 oxyethylene units. In some embodiments, the polyoxyethylene portion of the molecule has about 2 to about 100 oxyethylene units. In some embodiments, the polyoxyethylene portion of the molecule has about 4 to about 50 oxyethylene units. In some embodiments, the polyoxyethylene portion of the molecule has about 4 to about 30 oxyethylene units. In some embodiments, the polyoxyethylene fatty alcohol ether comprises ethoxylated stearyl alcohols, cetyl alcohols, and cetylstearyl alcohols (cetearyl alcohols). Suitable polyoxyethylene fatty alcohol ethers include, but are not limited to, the Brij™ series of surfactants (available from Uniqema), which includes Brij 30, 35, 52, 56, 58, 72, 76, 78, 93Veg, 97, 98, and 721, the Cremophor™ A series (available from BASF), which includes Cremophor A6, A20, and A25, the Emulgen™ series (available from Kao Corp.), which includes Emulgen 104P, 123P, 210P, 220, 320P, and 409P, the Ethosperse™ (available from Lonza), which includes Ethosperse 1A4, 1A12, TDAa6, 5120, and G26, the Ethylan™ series (available from Brenntag), which includes Ethylan D252, 253, 254, 256, 257, 2512, and 2560, the Plurafac™ series (available from BASF), which includes Plurafac RA20, RA30, RA40, RA43, and RA340, the Ritoleth™ and Ritox™ series (available from Rita Corp.), the Volpo™ series (available from Croda), which includes Volpo N 10, N 20, S2, S10, C2, C20, CS10, CS20, L4, and L23, and the Texafor™ series, which includes Texafor A1P, AP, A6, A10, A14, A30, A45, and A60. Other suitable polyoxyethylene fatty alcohol ethers include, but are not limited to, polyethylene glycol (13)stearyl ether (steareth-13), polyethylene glycol (14)stearyl ether (steareth-14), polyethylene glycol (15)stearyl ether (steareth-15), polyethylene glycol (16)stearyl ether (steareth-16), polyethylene glycol (17)stearyl ether (steareth-17), polyethylene glycol (18) stearyl ether (steareth-18), polyethylene glycol (19)stearyl ether (steareth-19), polyethylene glycol (20)stearyl ether (steareth-20), polyethylene glycol (12)isostearyl ether (isosteareth-12), polyethylene glycol (13)isostearyl ether (isosteareth-13), polyethylene glycol (14)isostearyl ether (isosteareth-14), polyethylene glycol (15)isostearyl ether (isosteareth-15), polyethylene glycol (16)isostearyl ether (isosteareth-16), polyethylene glycol (17)isostearyl ether (isosteareth-17), polyethylene glycol (18)isostearyl ether (isosteareth-18), polyethylene glycol (19)isostearyl ether (isosteareth-19), polyethylene glycol (20)isostearyl ether (isosteareth-20), polyethylene glycol (13)cetyl ether (ceteth-13), polyethylene glycol (14)cetyl ether (ceteth-14), polyethylene glycol (15)cetyl ether (ceteth-15), polyethylene glycol (16)cetyl ether (ceteth-16), polyethylene glycol (17)cetyl ether (ceteth-17), polyethylene glycol (18)cetyl ether (ceteth-18), polyethylene glycol (19)cetyl ether (ceteth-19), polyethylene glycol (20)cetyl ether (ceteth-20), polyethylene glycol (13)isocetyl ether (isoceteth-13), polyethylene glycol (14) isocetyl ether (isoceteth-14), polyethylene glycol (15)isocetyl ether (isoceteth-15), polyethylene glycol (16)isocetyl ether (isoceteth-16), polyethylene glycol (17)isocetyl ether (isoceteth-17), polyethylene glycol (18)isocetyl ether (isoceteth-18), polyethylene glycol (19)isocetyl ether (isoceteth-19), polyethylene glycol (20)isocetyl ether (isoceteth-20), polyethylene glycol (12)oleyl ether (oleth-12), polyethylene glycol (13)oleyl ether (oleth-13), polyethylene glycol (14) oleyl ether (oleth-14), polyethylene glycol (15)oleyl ether (oleth-15), polyethylene glycol (12)lauryl ether (laureth-12), polyethylene glycol (12)isolauryl ether (isolaureth-12), polyethylene glycol (13)cetylstearyl ether (ceteareth-13), polyethylene glycol (14)cetylstearyl ether (ceteareth-14), polyethylene glycol (15)cetylstearyl ether (ceteareth-15), polyethylene glycol (16)cetylstearyl ether (ceteareth-16), polyethylene glycol (17)cetylstearyl ether (ceteareth-17), polyethylene glycol (18)cetylstearyl ether (ceteareth-18), polyethylene glycol (19)cetylstearyl ether (ceteareth-19), and polyethylene glycol (20)cetylstearyl ether (ceteareth-20). The numbers following the "polyethylene glycol" term refer to the number of oxyethylene repeat units in the compound. Blends of polyoxyethylene fatty alcohol ethers with other materials are also useful in the invention. A non-limiting example of a suitable blend is Arlacel™ 165 or 165 VEG (available from Uniqema), a blend of glycerol monostearate with polyethylene glycol-100 stearate. Other suitable polyoxyethylene fatty alcohol ethers include those listed in R. C. Rowe and P. J. Shesky, Handbook of pharmaceutical excipients, (2006), 5th ed., which is incorporated herein by reference in its entirety.

As used herein, the term "polyoxyethylene-glycerol fatty ester" refers to ethoxylated fatty acid ester of glycerine, or mixture thereof. In some embodiments, the polyoxyethylene portion of the molecule has about 2 to about 200 oxyethylene units. In some embodiments, the polyoxyethylene portion of the molecule has about 2 to about 100 oxyethylene units. In some embodiments, the polyoxyethylene portion of the molecule has about 4 to about 50 oxyethylene units. In some embodiments, the polyoxyethylene portion of the molecule has about 4 to about 30 oxyethylene units. Suitable polyoxyethylene-glycerol fatty esters include, but are not limited to, PEG-20 glyceryl laurate, Tagat™ L (Goldschmidt); PEG-30 glyceryl laurate, Tagat™ L2 (Goldschmidt); PEG-15 glyceryl laurate, Glycerox™ L series (Croda); PEG-40 glyceryl laurate, Glycerox™ L series (Croda); PEG-20 glyceryl stearate, Capmul™ EMG (ABITEC), Aldo MS-20 KFG (Lonza); PEG-20 glyceryl oleate, Tagat™ O (Goldschmidt); PEG-30 glyceryl oleate, Tagat™ O2 (Goldschmidt).

As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, Handbook of pharmaceutical excipients, (2006), 5th ed., which is incorporated herein by reference in its entirety.

As used herein, the term "starch" refers to any type of natural or modified starch including, but not limited to, maize starch (also known as corn starch or *maydis* amylum), potato starch (also known as *solani* amylum), rice starch (also known as *oryzae* amylum), wheat starch (also known as *tritici* amylum), and tapioca starch. The term "starch" also refers to starches that have been modified with regard to molecular weight and branching. The term "starch" further refers to starches that have been chemically modified to attach chemical functionality such as carboxy, hydroxyl, hydroxyalkylene, or carboxyalkylene groups. As used herein, the term "carboxyalkylene" refers to a group of formula -alkylene-C(O)OH, or salt thereof. As used herein, the term "hydroxyalkylene" refers to a group of formula -alkylene-OH. Suitable sodium starch glycolates include, but are not limited to, Explotab (available from JRS Pharma), Glycolys (available from Roquette), Primojel (available from DMV International), and Vivastar (available from JRS Pharma).

Suitable pregelatinized starches include, but are not limited to, Lycatab C and PGS (available from Roquette), Merigel (available from Brenntag), National 78-1551 (available from National Starch), Spress B820 (available from GPC), and Starch 1500 (available from Colorcon).

As used herein, the term "stearoyl macrogol glyceride" refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefossé).

As used herein, the term "vegetable oil" refers to naturally occurring or synthetic oils, which may be refined, fractionated or hydrogenated, including triglycerides. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, Handbook of pharmaceutical excipients, (2006), 5th ed., which is incorporated herein by reference in its entirety.

Optical Isomers-Diastereomers-Geometric Isomers-Tautomers-Salts. Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The formulas are shown without a definitive stereochemistry at certain positions. The present invention includes all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration. Compounds may be neutral or pharmaceutically salts thereof. Formulas for carboxylic acids and sulfonamides may be drawn in protonated or unprotonated forms as the acid or amide, ion, or salt, and that all are encompassed by a given formula.

The term "alkyl," as used herein, unless otherwise specified, refers to a saturated or unsaturated straight or branched hydrocarbon chain of typically C1 to C10, and specifically includes methyl, ethyl, propyl, isopropyl, butyl, isobutyl, t-butyl, pentyl, isopentyl, neopentyl, hexyl, isohexyl, cyclohexyl, cyclohexylmethyl, 3-methylpentyl, 2,2-dimethylbutyl, 2,3-dimethylbutyl, ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like. Unsaturated alkyls have at least one double bond, of either E or Z stereochemistry where applicable. The term includes both substituted and unsubstituted alkyl groups.

The term "substituted" as used herein in reference to a moiety or group means that one or more hydrogen atoms in the respective moiety, especially up to 5, more especially 1, 2 or 3 of the hydrogen atoms are replaced independently of each other by the corresponding number of the described substituents. Alkyl groups can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, phosphonates, optionally substituted heterocycles, or optionally substituted aryls. One or more of the hydrogen atoms attached to carbon atom on alkyl may be replaces by one or more halogen atoms, e.g. fluorine or chlorine or both, such as trifluoromethyl, difluoromethyl, fluorochloromethyl, and the like. The hydrocarbon chain may also be interrupted by a heteroatom, such as N, O or S.

As used herein, the term "aryl" means a monovalent monocyclic or bicyclic aromatic hydrocarbon radical of 6 to 10 ring atoms, and optionally substituted independently with one, two or three substituents selected from alkyl, haloalkyl, cycloalkyl, halo, nitro, cyano, optionally substituted phenyl, —OR (where R is hydrogen, alkyl, haloalkyl, cycloalkyl, optionally substituted phenyl), acyl, —COOR (where R is hydrogen or alkyl). More specifically the term aryl includes, but is not limited to, phenyl, 1-naphthyl, 2-naphthyl, and derivatives thereof.

"Heterocycles" means a saturated, unsaturated, or aromatic monovalent ring of 3 to 8 ring atoms in which 1, 2, 3, or 4 ring atoms are heteroatoms selected from N, O, or S, the remaining ring atoms being C. The heterocyclo ring may be optionally fused to a benzene ring. The heterocyclic ring may be optionally substituted independently with one or more substituents, preferably one, two or three substituents, selected from alkyl, haloalkyl, cycloalkyl, cycloalkylalkyl, aryl, aralkyl, halo, cyano, acyl, monosubstituted amino, disubstituted amino, carboxy, hydroxyl, or alkoxycarbonyl. The heterocycle ring may have 1, 2, or 3 oxo substitution. Hydroxyls may exist in the keto or enol tautomer. More specifically the term heterocyclo includes, but is not limited to dioxanyl, imidazolidinyl, imidazolyl, morpholinyl, oxazolidinyl, oxazinyl, oxadiazolidinyl, oxadiazolyl, piperidinyl, piperazinyl, pyrrolidinyl, pyrrolyl, dihydropyrazolyl, pyrazolyl, tetrahydropyranyl, thiazolyl, thiomorpholinyl, triazolyl and derivatives.

This invention and embodiments illustrating the method and materials used may be further understood by reference to the following non-limiting examples.

Although the present invention has been described in considerable detail with reference to certain preferred embodiments thereof, other versions are possible. Therefore the spirit and scope of the appended claims should not be limited to the description and the preferred versions contained within this specification.

RAS proteins may self assemble together with other membrane-associated proteins, effectors and scaffolding proteins into plasma membrane tethered microdomains known as nanoclusters. The nanoclusters may be small (about 6-20 nm diameter) short lived (t1/2 less than about 0.4 s) signaling platforms, and may contain 6 or more proteins. Nanoclusters can differ depending upon the charge and covalent lipid modification of the C-terminal hypervariable (hv) region of the individual RAS isoforms. Downstream signaling effectors may be activated by the about 40% of the RAS which is associated in nanoclusters, while the remaining RAS is randomly arrayed over the cell surface.

RAS proteins undergo several steps of translational modification which can determine their membrane localization (FIG. 1). RAS may share a C-terminal CAAX motif that can undergo cysteine residue preneylation (C15 farnesylation or C20 geranylgeranylation) followed by removal of the AAX residues by endoplasmic reticulum (ER) Rce1 (RAS and a-factor converting enzyme-1) and carboxylation by Icmt (isoprenylcysteine carboxyl methyltransferase). These CAAX modifications by themselves may not be sufficient for RAS plasma membrane association and a second signal may be required. HRAS, NRAS and KRAS4A can undergo C16 palmitoylation on cysteine residues in their hv regions catalyzed by ER PATs (protein acyltransferases). In KRAS4B, the second membrane localization signal can be provided by a lysine rich polybasic amino acid sequence in its hv region that can facilitate an interaction with the negatively charged head groups of and phosphatidylinositol (PI) on the inner surface of the plasma membrane. PIP3 can be clustered in lipid raft nanodomains together with high levels of PI3K protein, to give regions of high signaling activity. The binding of the CNKSR1 PH-domain to PIP3 could serve to position the KRAS nanocluster in close proximity to the PI3K signaling nanodomain leading to activation of PI3K, a downstream signaling effector for KRAS. Some forms of mut-KRAS can have a higher affinity for binding to PI3K than wt-KRAS, due to a mutation induced change in the structure of the KRAS switch 1 and 2 binding regions that form direct contact with the PI-3-K catalytic domain causing allosteric activation. This could explain the greater sensitivity of mut-KRAS to inhibition by siRNA knockdown of CNKSR1 or PH-domain inhibition, than wt-KRAS.

The PH-domain is an about 100 to about 120 amino acid three dimensional superfold found in over 500 human proteins. The core of each PH-domain consists of seven β-strands and a C-terminal a-helix. While PH-domains may show a highly conserved 3 dimensional organization, the sequence identities among different proteins are only about 7% to about 23%. This is important because with this sequence diversity, selective agents can be identified that will be specific for each protein. PH-domains can bind to phosphotyrosine and polyproline sequences, Gβγ subunits of heterotrimeric G proteins and phosphoinositides (PIs). While for the majority of PH-domain proteins PI binding is weak and non-specific, the PH-domains of many proteins that are components of signal transduction pathways regulating cancer cell growth and survival show high affinity for PIP3 and sometimes PIP2. CNKSR is one such protein that has high affinity binding for PIP3. In embodiments, the binding of a small molecule to a PH-domain may inhibit protein function.

In other embodiments, identifying small molecule PH-domain inhibitors using a computational platform may speed identification of potential inhibitors and the decrease the costs of optimizing a drug lead. In such embodiments, the in silico molecular docking of libraries of several million chemical structures using the known crystal or homology model structures of the PH-domain of the protein of interest may be used to identify inhibitors of CNKSR1. Surface plasmon resonance (SPR) spectroscopy can measure the extent of binding of the compounds to the PH-domain of the protein, and in vitro cellular assays can determine biological efficacy. Once active moieties are identified there may be recursive refinement of the model through repeated in silico docking and SPR spectroscopic measurements of binding until lead compounds are obtained. Such embodiments may be used to discover highly specific and potent PH-domain inhibitors of CNKSR1.

This role of CNKSR1 as a molecular target for drug development is shown in FIG. 2A where transfection with siRNA to CNKSR1 (siCNKSR1) may inhibit growth of mut-KRAS MiaPaCa-2 pancreatic cells but not the growth of MiaPaCa-2 cells, where an allele of mut-KRAS has been disrupted by homologous recombination. siCNKSR1 may also inhibit growth of mut-KRAS HCT116 colon cancer cells but not the growth of HKE2 HCT116 cells, where mut-KRAS has been disrupted by homologous recombination. Table 1 shows that the selective inhibition of mut-KRAS cell growth can be validated with a second set of 4 individual siCNKSR1s from a second manufacturer.

TABLE 1

| Validated hits with individual siRNAs in mut-KRAS isogenic lines | | | | | |
|---|---|---|---|---|---|
| | | MiaPaCa-2 Pancreatic | | HCT-116 Colon | |
| Gene Symbol | Name | % viability mut-RAS/ wt-KRAS | siRNAs* positive | % viability mut-RAS/ wt-KRAS | siRNAs* positive |
| CNKSR1 | connector enhancer of kinase suppressor of Ras 1 | 43.4 | 3/4 | 52.6 | 3/4 |

*second manufacturers individual siRNAs

The effect of siCNKSR1 is further shown in FIG. 2B where transfection with siCNKSR1 can inhibit the growth of a panel of 10 mut-KRAS non small cell lung cancer (NSCLC) cell lines but not of 4 NSCLC cell lines with wt-KRAS.

In order to demonstrate whether the pleckstrin homology (PH) domain of CNKSR1 plays a role in facilitating the effect of CNKSR1 on mut-KRAS activity we over expressed the PH-domain in H1373 mut-KRAS NSCLC cells and found that it acted as a dominant negative and inhibited cell growth. We suggest that the PH-domain fragment competes with the full length CNKSR1 in the cell (FIG. 2C).

In embodiments, a homology model for the PH-domain of CNSKR1 based on known PH-domain crystal structures can be developed. The docking program PHuDock® can be used to identify potential inhibitors of CNKSR1. Using an in silico library of over 3 million compounds, seven compounds have been identified as potential inhibitors of CNKSR1 and, thus, of mut-KRAS cell lines (FIG. 3A). The binding of the compounds to the expressed PH-domain of CNKSR1 (KDobs) can be measured by surface plasmon resonance (SPR) spectroscopy. Two of the seven identified compounds (compounds #4 and #7) exhibit low micromolar inhibition of mut-KRAS cell growth (FIG. 3B). The most active compound was #7, which inhibited mut-KRAS cell growth as effectively as siRNA to KRAS or CNKSR1 (FIG. 3C).

In embodiments, the binding of identified compounds to the crystal structures of other PH-domain signaling proteins, AKT, PDPK1, Btk, and Tiam1 can be predicted. In such embodiments, the Kds exceed about 100 μM. In other embodiments, SPR can measure the binding of identified compounds to the expressed PH-domains of AKT, PDPK1 and Tiam1. No measurable binding was found for #4 and #7. Thus, the identified compounds appear have, at least, about 50 to about 100 fold selectivity for CNKSR1 compared to the other PH-domains studied.

In embodiments, a homology model can predict small molecules that bind to the PH-domain of CNKSR1, and identify compounds that exhibit selective inhibition of mut-KRAS cell proliferation. CNKSR1 inhabitation of K-RAS signaling can be measured by Western blotting of the down stream target phospho-c-RAF(Ser338) which is specifically phosphorylated by KRAS (FIG. 3D).

In embodiments, identified compounds may be nontoxic at about 200 mg/day for about 20 days with no weight loss and no observable toxic effects for the animal, and may have antitumor activity (FIG. 4 A). Compound #7 may have antitumor activity against a mut-KRAS H2122 NSCLC tumor xenograft in scid mice, where the growth rate of vehicle treated tumors (n=10 mice per group) may be about 55 $mm^3$/day and that of compound 7 treated tumors may be about 30 $mm^3$/day giving a tumor growth rate inhibition of about 45%.

In order to understand better the reasons for the antitumor activity of compound #7 pharmacokinetic studies were conducted. It was found that compound #7, which is an ethyl ester, administered orally at a dose of 200 mg/kg was rapidly de-esterified to the acid metabolite in vivo (FIG. 4B), and also by mouse plasma (Table 1). Following oral administration in vivo plasma concentrations of the parent compound were low, about 3 μg/ml (7 μM) whereas the de-esterified acid form (compound 8) was present at high peak concentrations of around 50 μg/ml (128 μM). When compound 8 was administered orally to mice at the same dose even higher peak concentrations of 90 μg/ml (230 μM) were achieved. Compound #7 was eliminated with a half life of 6 hr and compound 7 with a half life of 13 hr. Because compound #8 is inactive in cells in culture (see FIG. 5) it is likely that the rapid conversion of compound #7 to its inactive metabolite compound 8 limits its in vivo activity.

It is noteworthy that compound #7 was more stable in dog and bovine serum and completely stable in human plasma which might lead to less metabolism in human, although it was broken down by human carboxylesterases 1 and 2 (Table 2) which are found in human intestine, liver and tumor.

In order to develop more stable analogs of compound 7 we further modeled and

TABLE 2

Stability of compound 7 in biological media*

|  | Half life (min) |
| --- | --- |
| Mouse plasma | 6.3 |
| Dog plasma (beagle) | 558 |
| Human plasma | stable |
| 10% fetal bovine serum | 790 |
| rHuman carboxyesterase 1 24 U/ml # | 19 |
| rHuman carboxyesterase 2 24 U/ml # | 99 |

*compound 7 concentration 50 μg/ml, temperature 37° C., # pH 7.4, 1 U = 1 nmol/min synthesized a group of compounds with a rigid non-hydrolysable group in place of the ester functionality (FIG. 5, compounds 9, 10, 11). All three compounds inhibited the growth of mut-KRAS NSCLC cell lines but also inhibited wt-KRAS cell growth. Compound #10 was the most potent and showed approximately two fold selectivity for mut-KRAS cells compared to wt-KRAS cells.

Through further modeling and screening using an optimal CNKR1 model (FIG. 7) a new pharmacophore was identified (Table 3 compound 35) identified as #12 in FIG. 5, that inhibits the growth of wt-KRAS and mut-KRAS cells more potently than compound 7 or its analogs. In this study a ligand-based method that takes into account molecular shape of a query molecule and the pharmacophoric features (acceptor, donor, hydrophobic, aromatic, etc.) of its functional groups was launched. The underlying hypothesis is that molecular entities such as inositol X-phosphate may bind in the pocket of the PH-domain. Thus, providing a competing molecule for that site could diminish its activity in a noticeable manner.

The X-Ray structure of a PH-domain target bound to inositol tetraphosphate (IP4) was retrieved from the RCSB (code: 1UNQ) and prepared within MAESTRO utilizing the Protein Preparation Wizard module. The ligand was extracted and used as a query for virtual screening using the shape screening module of the aforementioned software. Databases of commercial vendors were downloaded as SDF files and converted into 3D structures with Ligprep at pH 7 and calculating protomers and tautomers using EPIK. Basic Lipinski's rules of drug-likeness were used to filter out offending compounds. The phase shape program within MAESTRO was employed to screen the aforementioned databases. Briefly, conformers were generated "on the fly" and up to 1000 low energy conformations per each entry in the commercial databases were retained and screened. The atom type used was Phase QSAR Model due to its remarkable good shape screening capabilities seen in previous cases. Conformers with similarity below 0.7 were discarded and the results ranked based on shape similarity. A large database of approximately 3000 compounds was retrieved from the method and every single compound was visually inspected to maximize hydrogen bond pattern, maximum overlap of functional groups and overall shape and geometry of the molecules. A subset of these compounds were tested; the compounds are as follows;

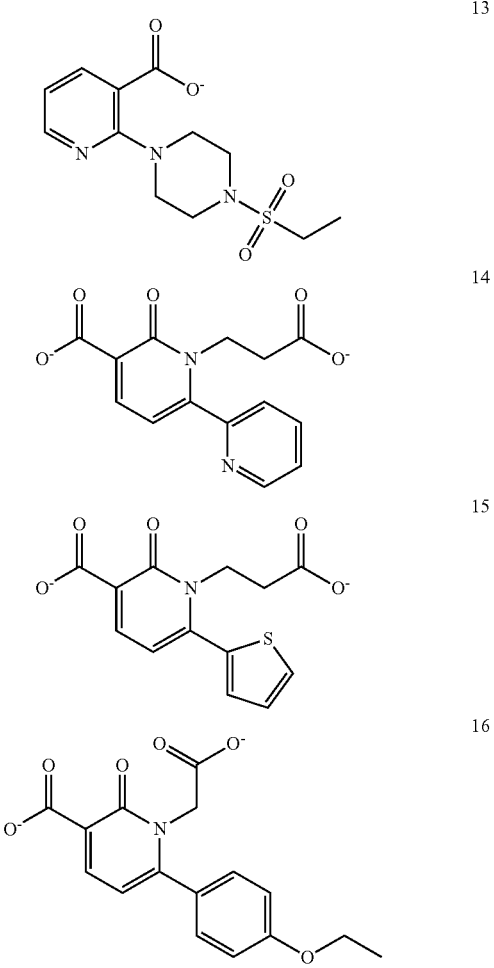

17 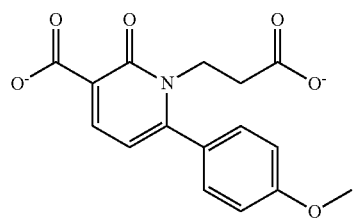
18 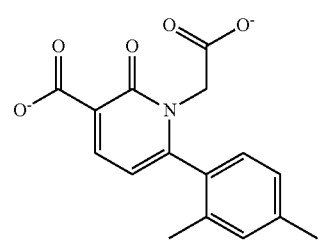
19 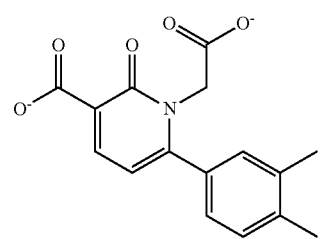
20 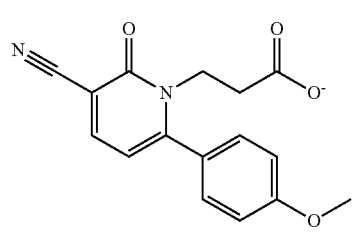
21 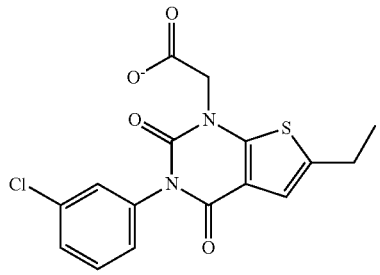
22 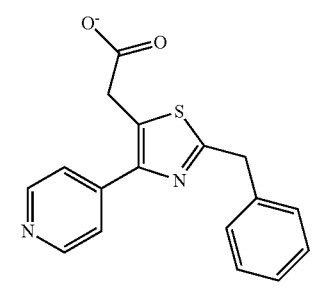
23 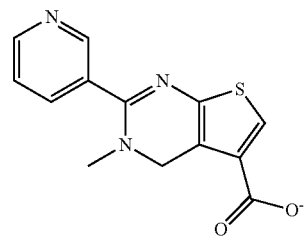
24 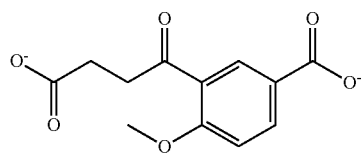
25 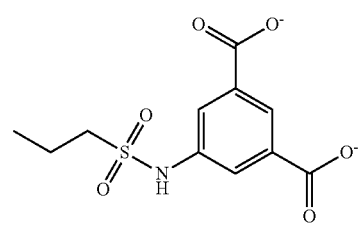
26 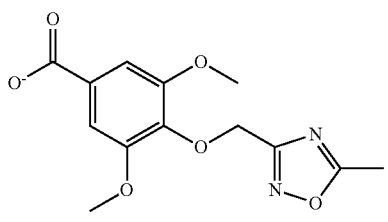
27 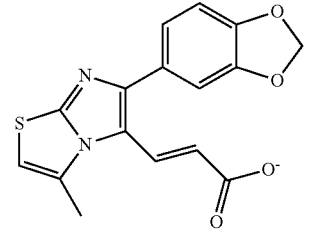
28 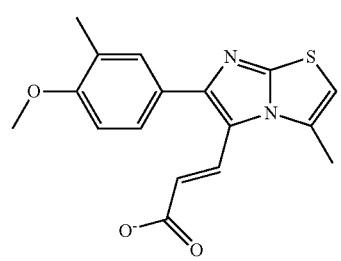
29 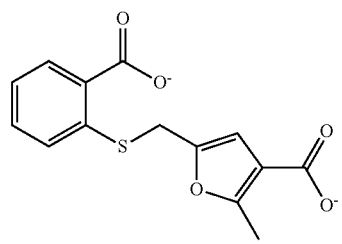

30
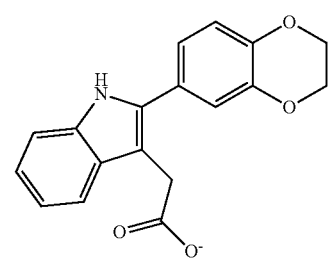
31
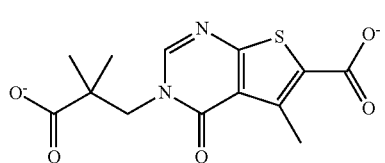
32
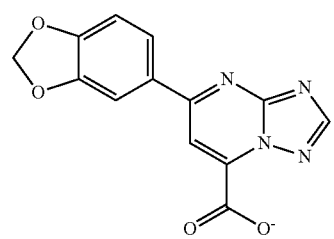
33
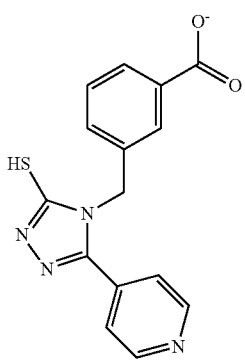
34
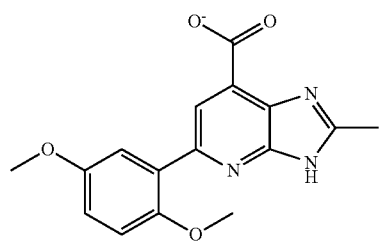
35
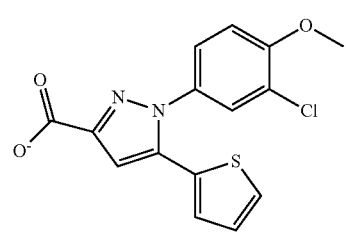
36
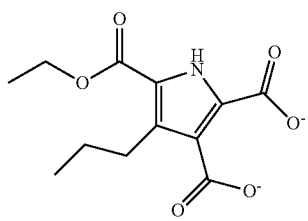
37
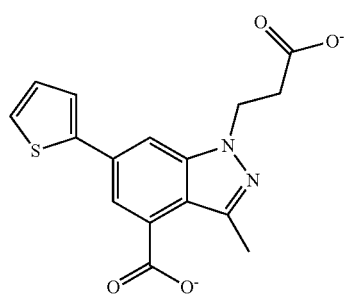
38
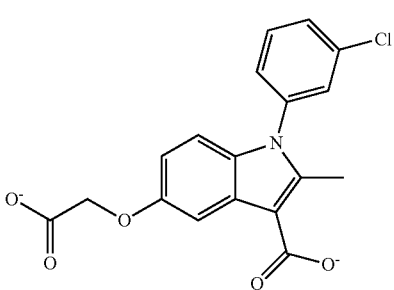
39
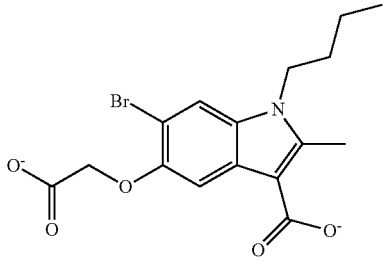
40
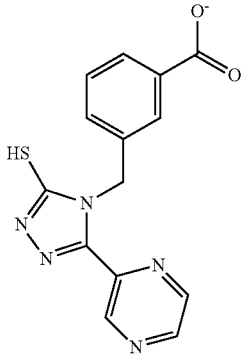

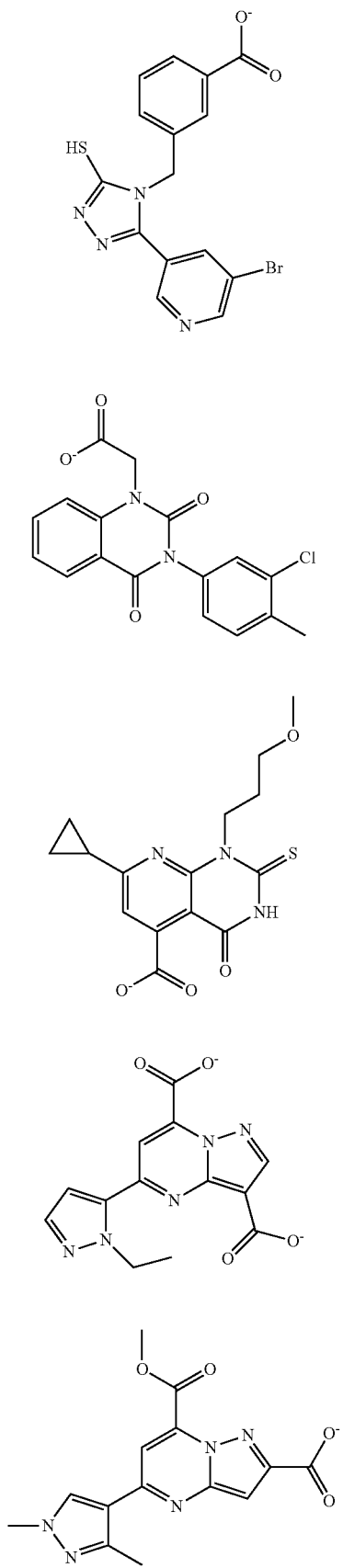
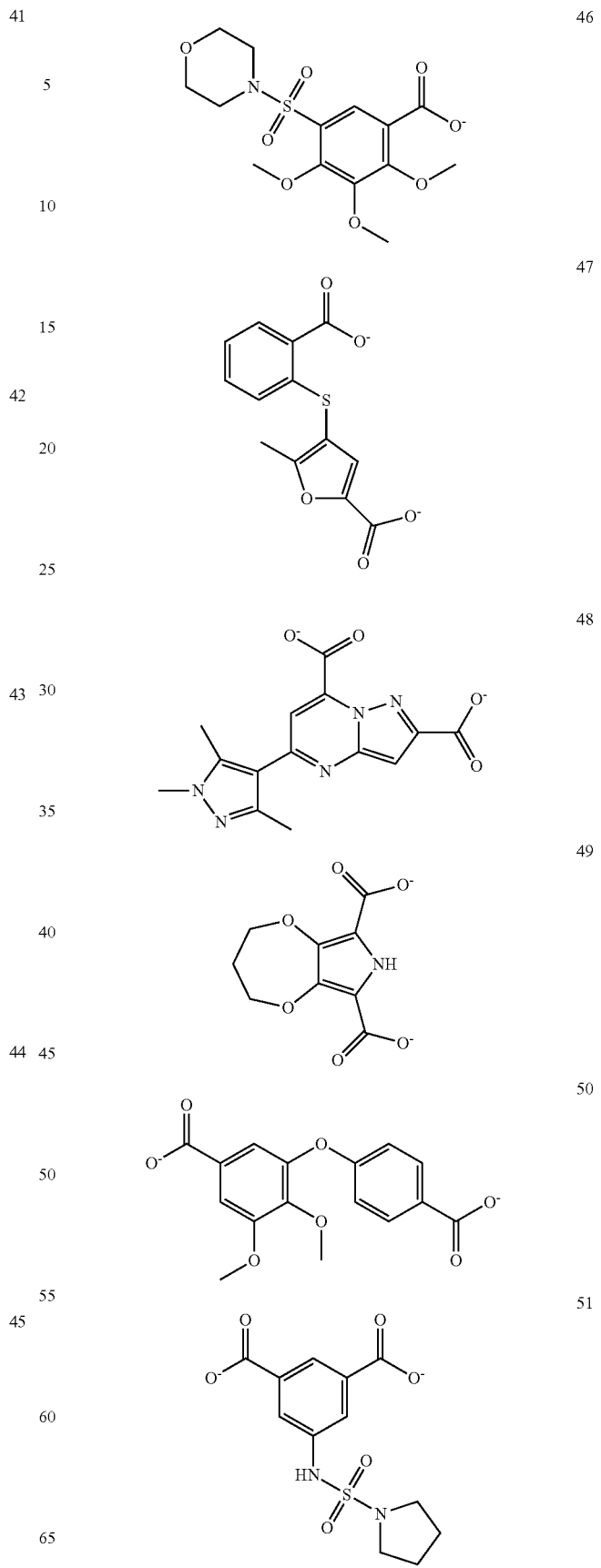

52
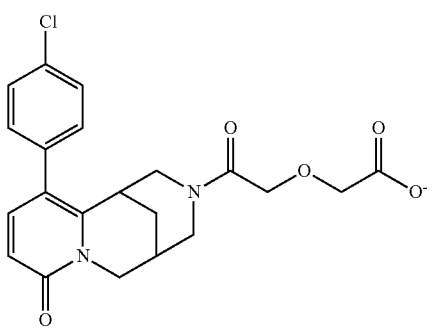
53
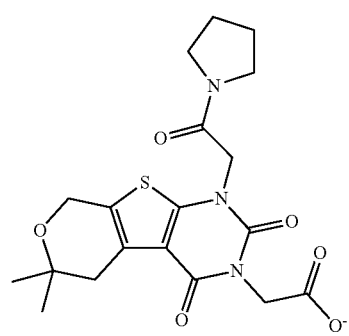
54
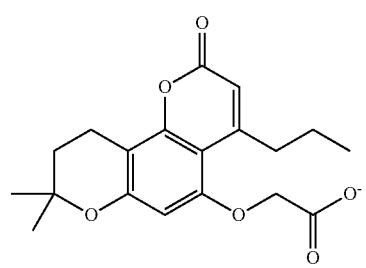
55
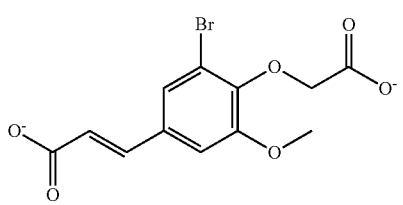
56
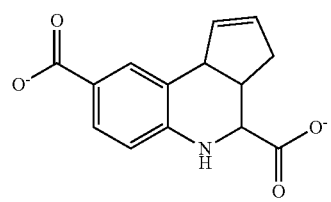
57
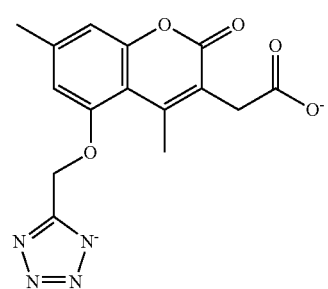
58
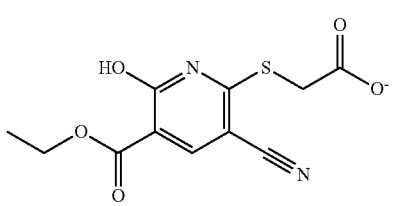
59
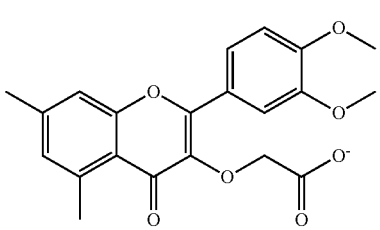
60
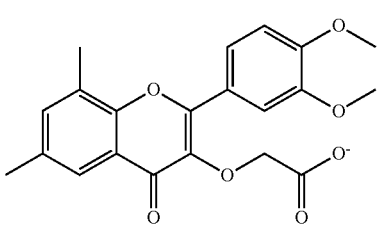
61
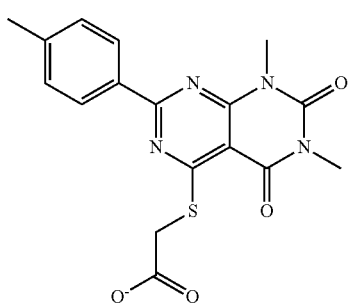
62
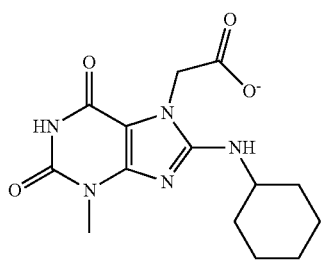
63
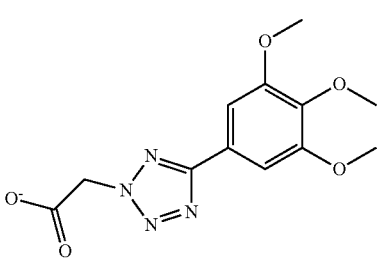

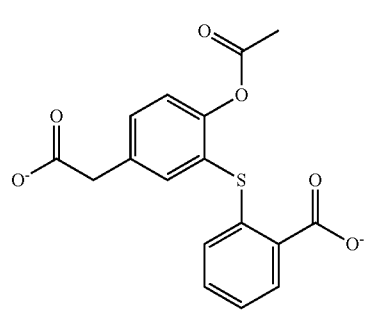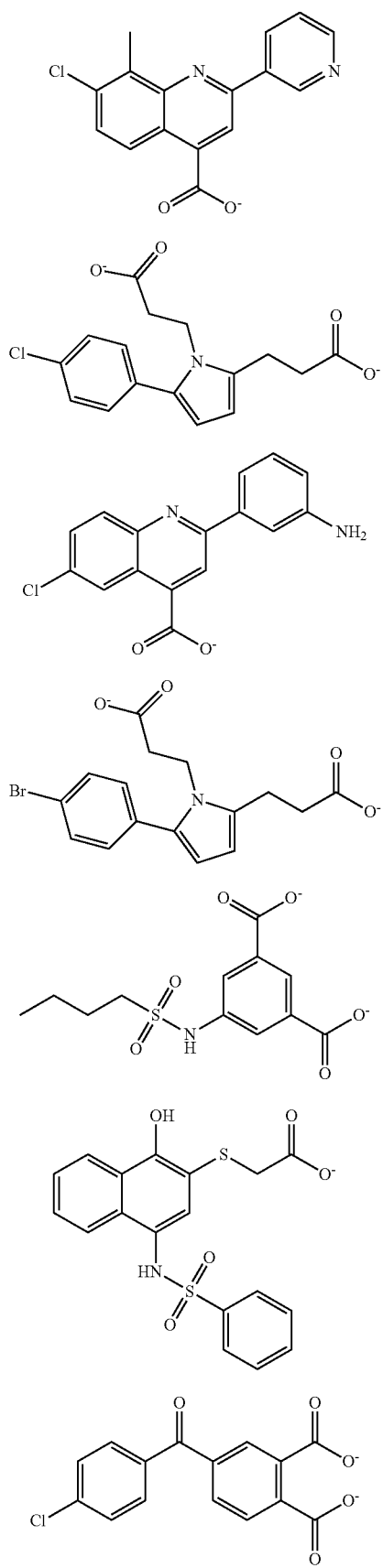

-continued

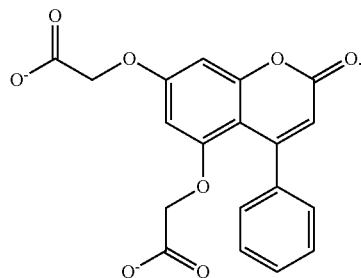

A particularly active compound was found (FIG. 5 Compound 12). An additional subset of these compounds were purchased and tested including: 1,2,4-trihydroxyanthracene-9,10-dione, benzimidazole-5,6-dicarboxylic acid, 4-(aminocarbonylamino)benzoic acid, 2-(5-methyl-3-nitropyrazolyl)-N-(4-sulfamoylphenyl)acetamide, N-(1-acetyl-4-oxo-5-hydroimidazo[5,4-d]pyridin-6-yl)acetamide, N-[4-(hydrazinosulfonyl)phenyl]acetamide, 3,5-di(acetylamino)-2-methylbenzoic acid, 2-[(2-hydroxy-tert-butyl)amino]-N-(4-sulfamoylphenyl)acetamide, 2-{[(N-(3-pyridyl)carbamoyl)methyl]cyclopentyl}acetic acid, N-(3-hydroxy(2-pyridyl))[4-(morpholin-4-ylsulfonyl)(2-thienyl)]carboxamide, 4-(benzo[d]furan-2-ylcarbonylamino)benzoic acid, 2-chloro-5-{[N-(3-chlorophenyl)carbamoyl]amino}benzoic acid, 4-[(1-methylpyrazol-3-yl)carbonylamino]benzoic acid, 4-{[5-(methoxymethyl)-2-furyl]carbonylamino}benzoic acid, benzo[d]furan-2-yl-N-(4-sulfamoylphenyl)carboxamide, 3-[N-(4-{[(2,4-dimethylphenyl)amino]sulfonyl}phenyl)carbamoyl]propanoic acid, 3-[N-(4-{[4-(3-carboxypropanoylamino)-3-hydroxyphenyl]methyl}-2-hydroxyphenyl)carbamoyl]propanoic acid, N-benzothiazol-2-yl-3-(phenylsulfonyl)propanamide, 2-benzimidazol-2-ylthioacetohydrazide, N-(4-chlorophenyl)[(4-sulfamoylphenyl)amino]carboxamide, 4-{[N-(3-chlorophenyl)carbamoyl]amino}benzamide, 3-((2E)-3-carboxyprop-2-enoylamino)benzoic acid, N-(3,4-dichlorophenyl) {[4-(N-methylcarbamoyl)phenyl]amino}carboxamide, 2-furyl-N-(4-sulfamoylphenyl)carboxamide, 2-naphthyl-N-(4-sulfamoylphenyl)carboxamide, [1-(methylsulfonyl)indolin-5-yl]-N-(2-pyridyl)carboxamide, N-(3-chlorophenyl)[(6-methoxy(3-pyridyl))amino]carboxamide, 2-(7H-1,2,4-triazolo[4,5-d]1,2,4-triazolin-3-ylthio)-N-(2-pyridyl)acetamide, 2-(2-methoxyphenoxy)-N-(4-sulfamoylphenyl)acetamide, N-[5-(acetylamino)-2-hydroxy-3-methylphenyl]acetamide, 2-(3-iodo(1,2,4-triazolyl))-N-(3,4,5-trimethoxyphenyl)acetamide, 2-morpholin-4-yl-N-(4-sulfamoylphenyl)acetamide, N-(benzimidazol-2-ylmethyl)-2-(4-hydroxyquinazolin-2-ylthio)acetamide, N-(3-methylphenyl)-2-[9-(4-methylphenyl)-6-oxohydropurin-8-ylthio]acetamide, N-{4-[(naphthylamino)sulfonyl]phenyl}(phenylamino)carboxamide, 2-hydroxy-6-methoxyquinoline-4-carboxylic acid, 4-[N-(4-{N-[(1E)-2-(4-methoxyphenyl)-1-azavinyl]carbamoyl}phenyl)carbamoyl]butanoic acid, 6H,7H-1,4-dioxino[5,6-f]benzimidazol-2-ylmethan-1-ol, N-[(2-fluorophenyl)methyl]{[3-({N-[(2-fluorophenyl)methyl]carbamoyl}amino)phenyl]amino}carboxamide, benzo[d]furan-2-yl-N-(3-ethyl-4-oxo(3-hydroquinazolin-7-yl))carboxamide, 2-(2-oxo(3-hydrobenzoxazol-3-yl))-N-(1,3-thiazol-2-yl)acetamide, N-(2H-benzo[3,4-d]1,3-dioxolan-5-yl)-N'-(2H-benzo[3,4-d]1,3-dioxolen-5-yl)ethane-1,2-diamide, 2H,3H-furano[3,4-e]1,4-dioxane-5,7-dicarboxylic acid, ethyl 11-amino-12-cyano-8-(methoxymethyl)spiro [2H-3,4,5,6-tetrahydropyran-4,7'-4,7-dihydroimidazo[5,4-b]pyridine]-10-carboxylate, 2-(1,3-dimethyl-2,6-dioxo(1,3,7-trihydropurin-7-yl))-N-[5-(trifluoromethyl)(1,3,4-thiadiazol-2-yl)]acetamide, N-benzothiazol-2-yl(3-methyl-4-oxo(3-hydrophthalazinyl))carboxamide, (4-fluorophenyl)-N-(1-oxo(3-hydroisobenzofuran-5-yl))carboxamide, N-(3-fluoro-4-methylphenyl)-2-(6-oxo-9-phenylhydropurin-8-ylthio)acetamide, 2H-benzo[3,4-d]1,3-dioxolen-5-yl-N-(5-ethylthio(1,3,4-thiadiazol-2-yl))carboxamide, 6-(hydrazinecarbonyl)-4-oxo-3,4-dihydrophthalazin-1-olate, 2-(7-amino(1,2,4-triazolo[4,5-d]1,2,4-triazolin-3-ylthio))-N-(5-ethyl(1,3,4-thiadiazol-2-yl))acetamide, 2-amino-5-methyl-4-oxo-5-hydro-1,3-thiazolo[5,4-d]pyridazine-7-carbonitrile, hydro-5H-1,2,3-triazolo[4,5-f]benzotriazole-4,8-dione, N-(2-hydroxyphenyl) {3-[N-(2-hydroxyphenyl)carbamoyl]-5-(phenylcarbonylamino)phenyl}carboxamide, N-(2H,3H-benzo[3,4-e]1,4-dioxan-6-yl)-8-hydro-1,2,4-triazolo[1,5-a]pyrimidin-2-ylcarboxamide, 4-hydrazinecarbonyl-3-methylbenzo[4,5-d]pyrido[1,2-a]imidazole-1-olate, N-methyl-2-oxo-1,2-dihydrobenzo[cd]indole-6-sulfonamide, N-(2H,3H-benzo[3,4-e]1,4-dioxin-6-yl)-2-[1-(2-methoxyphenyl)-5,7-dimethyl-2,4-dioxo(1,3-dihydropyridino[2,3-d]pyrimidin-3-yl)]acetamide, 2-amino-5-(2,6-diamino-4-oxo(3-hydropyrimidin-5-yl))-6-(5-chloro(2-thienyl))-3-hydropyrrolo[2,3-d]pyrimidin-4-one, 5-hydroxy-1,3-dimethyl-1,3,8-trihydropyridino[2,3-d]pyrimidine-2,4,7-trione, 6-hydroxy-5-[(6-hydroxy-4-oxo-2-thioxo(1,3-dihydropyrimidin-5-yl))methyl]-2-thioxo-1,3-dihydropyrimidin-4-one, methyl 5-(2-furylcarbonylamino)-3-(methoxycarbonyl)benzoate, 2-{[N-(9,10-dioxoanthryl)carbamoyl]methylthio}acetic acid, 2-(2,4-dibromophenoxy)-N-(4-{[(4-sulfamoylphenyl)amino]sulfonyl}phenyl)acetamide, 1,3-bis(hydroxymethyl)-5-methoxy-3-hydrobenzimidazol-2-one, 10-[(3-chlorophenyl)amino]-2,3-dimethoxy-5,6,7-trihydropyrimidino[6,1-a]isoquinolin-8-one, 2,4-bis(4-hydroxyphenyl)cyclobutane-1, 3- and dicarboxylic acid.

Further exploration of the active compounds suggested that hybrid molecules based on compounds #7 and #12 may provide more selective novel compounds. Table 4 identifies six hybrid compounds with good retrosynthetic scores. Their PKD properties were calculated including parameters such as Log P, log S and MW of molecules. To undertake the hybridization, novel ligands were generated through the recombination of two active ligand fragments based the known structural information (FIG. 8). The new molecules are a hybrids of two scaffolds or a transfer of a substituent from one scaffold to another. The input geometries are assumed to be significant, thus new structures preserve intramolecular orientations as closely as possible.

Experimental results indicated that compounds #7 and #12 inhibit CNKR1. The striking similarity of the 4-oxophthalazin scaffold of compound #7 with the 2-hydroxynaphtalen of compound #12, combined with the acetate moiety of #7 and the sulfanylacetate of #12 possibly suggests a common binding mode. Thus, the hybridized molecules could provide improved pharmacological features.

Compounds #7 and #12 were loaded as 3D SDfiles into MAESTRO and the BREED python script was run. The default mode was used which briefly the bond overlap criteria was set to a maximum atom-atom distance of 1.0 Å and a maximum angle of 15 degrees was allowed to take place. The number of generations was set to 1. The six compounds shown in Table 4 were obtained.

TABLE 4

Compounds modeled and identified based on hybridization of Compound 7 and 12.

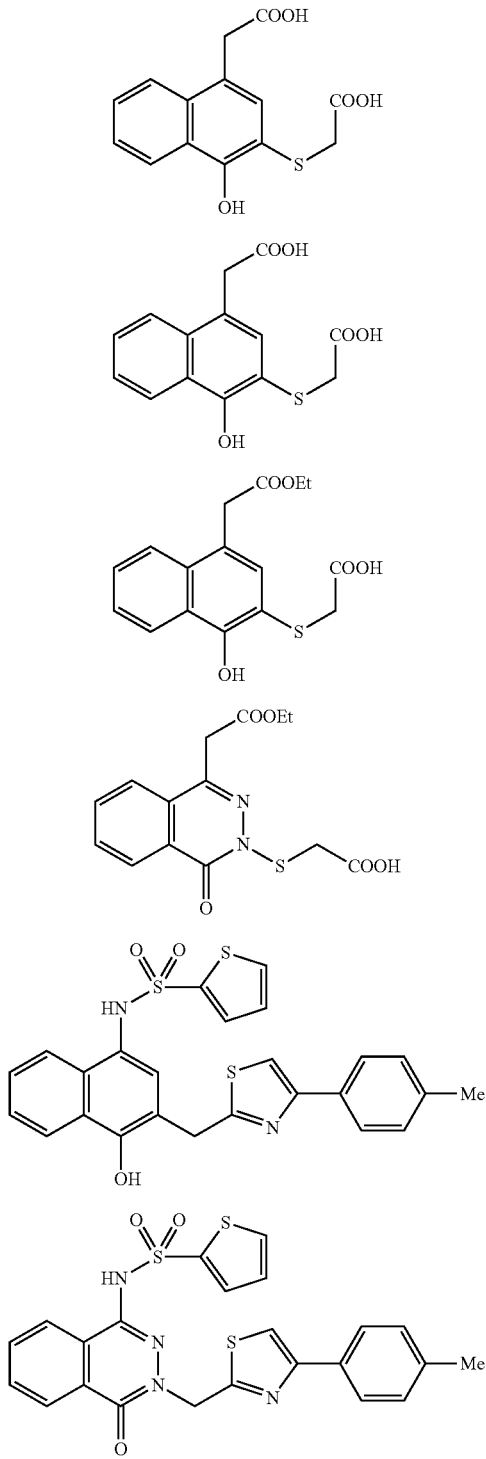

Experimental Description
Screening of Compounds Against Isogenic Mutant KRAS Lines (FIG. 2).

The isogenic KRAS lines harboring G12D, G12C, and G12V were obtained from Horizon Discovery labs on a one year lease. These cells were cultured in McCoys media with 10% FBS to 80% confluency. Cells were then released from flasks via trypsinization and plated into 96-well plates at an initial density range of 2000 cells per well. Cells were allowed 24 hours to attach, and then the agents were added to the culture media at a range of concentrations from 0-100 µM. Cells were incubated for 72 hours with the drugs, and then viability was assessed using an MTS viability assay. Cells were exposed to MTS reagent (Promega) dissolved in PBS (Hyclone) at a concentration of 200 µL reagent/mL media for 2 hours. Absorbance was then read at 490 nm, and viability was expressed as a percentage normalized between the negative control (no cells plated) and the condition of cells with no drug added (100% viability) normalized as the upper limit of viability.

Screening of Compounds Against NSCLC Cell Line Panel (FIGS. 2 and 3B).

Our panel of 30 cell lines and an extensive characterization were obtained from Dr. John Minna (UTSW). All cell lines were cultured in RPMI 1640 with 10% FBS. Cells were treated with concentrations of agents at concentrations 0.01 to 50 µM and evaluated as described above. $IC_{50}$'s were determined using Excelfit.

siRNA Screening

MiaPaCa-2 and M27 were confirmed *mycoplasma* and maintained in DMEM with 10% FBS. Optimization was carried out using in house optimization methods in house. A parallel screen was then carried out with a genome wide siRNA library (Dharmacon).

Individual siRNA and Plasmid Transfection (FIG. 3C).

For transfection in a six well plate, cells were plated at 100,000 cells per well in 2 mls media and allowed to attach overnight. Per well 5 µl of Dharmafect 2 (Dharmacon) was added to 200 µl OptiMEM (Gibco) and 4 µl of the siCNKSR1 smartpool Dharmacon (M-012217-01-0020) or individual siCNKSR1 siRNAs (Qiagen SI02665411) was added to 200 µL to OptiMEM in parallel and allowed to sit for 5 minutes. These tubes were mixed and incubated at room temperature for 20 minutes. 1.6 of the appropriate media was then added to this mixture. and then media in the wells removed. This mixture was then added to the cells in a dropwise fashion and the cells were incubated for 48-72 hours. For the GFP control and CNK1 PH-domain plasmids 175,000 cellsper well plated in a 6 well plate. Per well 2.5 µl of lipofectamine 2000 (Gibco) and 125 µl of OptiMEM were combined and 2.5 µg of the appropriate plasmid and 125 µl of OptiMEM were combined in separate tubes and allowed to incubate at room temperature for 5 minutes. These two tubes were then combined and allowed to incubate for 20 minutes. 200 µl of this mixture was then added to 1 ml of fresh media already in the appropriate well and allowed to incubate for 5 hours. The transfection efficiency was determined through the expression of GFP after 24 hours and the cells were counted with a hemocytometer after 72 hours to determine viability.

Spheroid Formation (FIG. 9)

The plates were optimized for the best cell density and found to be 20,000 cells per mL. The lid was removed from a 96-well Greiner plate and turned upside down. 20 µL of the 20,000 cells per mL suspension was then added directly into the middle of the circles found on the lid of the 96-well plate forming a small drop. 100 µL of media was added into the corresponding wells, used to maintain the temperature of the drops, and the lid was flipped back over carefully placing it back onto the plate without disturbing the drop. The plate was then placed into the incubator for 3 days to allow the cells to migrate to the bottom of the drop due to gravity. After 3 days, 400 µL of media was added to the corresponding wells a SCIVAX 96-well plate. The lid from the Greiner 96-well plate was removed and placed onto the SCIVAX plate allowing the drop to come in contact with the media and placed back into the incubator. After one hour, 200 µL of media was removed from the corresponding wells carefully without disturbing the spheroid and imaged.

Confocal Imaging (FIGS. 10 and 12)

HEK293T cells were co-transfected with CNK and either wild type or G12D mutant KRAS. Twenty-four hours post-transfection, cells were seeded on glass coverslips and allowed to grow a further 24 h and then serum deprived overnight. Cells were fixed with 4% (w/v) paraformaldehyde pH 8.0 for 20 min at room temperature. Following 6-7 washes with PBS (pH 8.0) the coverslip was mounted onto a slide with mounting medium (0.1% p-phenylenediamine/75% glycerol in PBS at pH 7.5-8.0). Confocal laser scanning microscopy was performed with a Leica SP5 confocal microscope system with 63× oil-immersion objective (numerical aperture NA=1.4), a line scan speed of 600 Hz, with image size of 1024×1024 pixels. GFP was excited with an argon-visible light laser tuned to 488 nm, mRFP were excited with a krypton laser tuned to 543 nm GFP and RFP fluorescence emissions were collected using a photomultiplier tube via 514/10 nm and 595/10 nm band selections respectively.

Fluorescence Lifetime Imaging Microscopy (FLIM) (FIGS. 11 and 13)

FLIM experiments were carried out using a Leica TCP SP5 inverted advanced confocal microscope system with internal photomultiplier tube (PMT) detector for TCSPC (time-correlated single-photon counting). The sample was excited with a tunable femtosecond (fs) titanium-sapphire laser with repetition rate of 80 MHz and pulse width less then 80 fs (Spectral Physics, Mai Tai BB). The wavelength used for two-photon excitation was 930 nm and the fluorescence was detected through a 525±25 nm interference filter. Images were obtained with oil-immersion objective (numerical aperture NA=1.4), a line scan speed of 400 Hz, with image size of 512×512 pixels. For FLIM analysis the pixels were reduced to 256×256. FLIM data was collected using Becker & Hickl SPC830 data and image acquisition card for TCSPC. The fluorescence decays were fitted with a single exponential decay model using Becker and Hickl's SPCImage software and the GFP fluorescence lifetimes were displayed in a false colour map.

Surface Plasmon Resonance Spectroscopy Binding Assays (Binding Scores for all Agents)

All interaction analyses were done with a Biacore T100 Control Software v3.2, and BIAevaluation v4.1 analysis software (Biacore). The PH-domain His-fusion proteins (CNK1 and AKT1) were expressed and immobilized on a NTA chip to a level of 10,000 response units or less. Small molecule analytes at concentrations ranging from 50 µM to 0.010 µM were injected at a high flow rate (30 µL/min) DMSO concentrations in all samples and running buffer were 1-5% (v/v) (30 µL/min) DMSO concentrations in all samples and running buffer were 1-5% (v/v).

Figure 15:
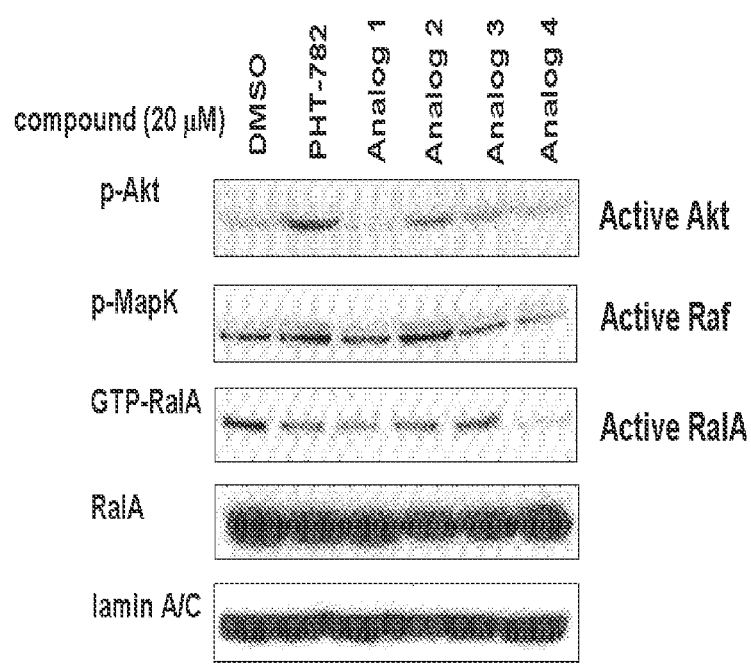
FIG. 15 shows increased activity for compounds in accordance with embodiments, for inhibition of KRas signaling effectors.
Figure 16A:
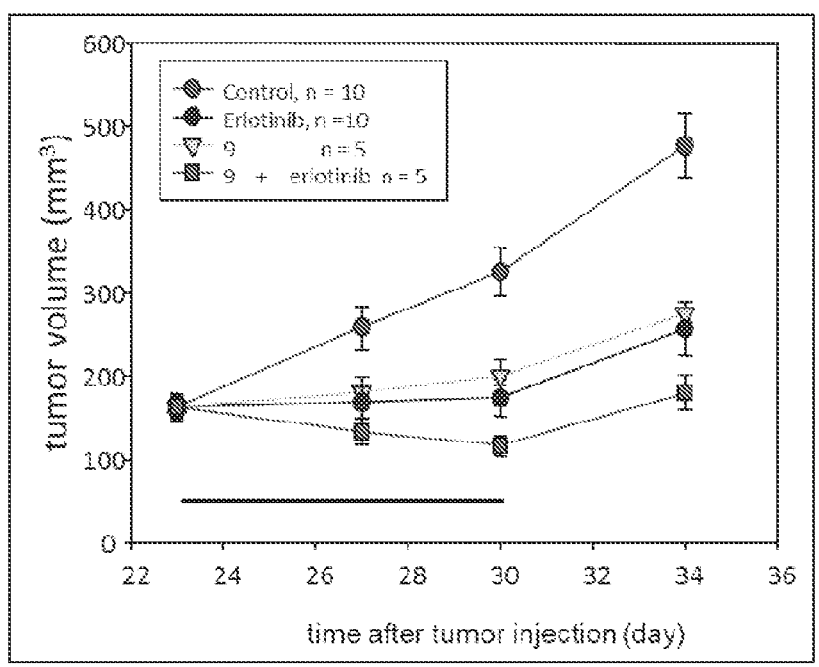
FIG. 16 is a graph showing antitumor activity observed compounds in accordance with embodiments.
Figure 16B:
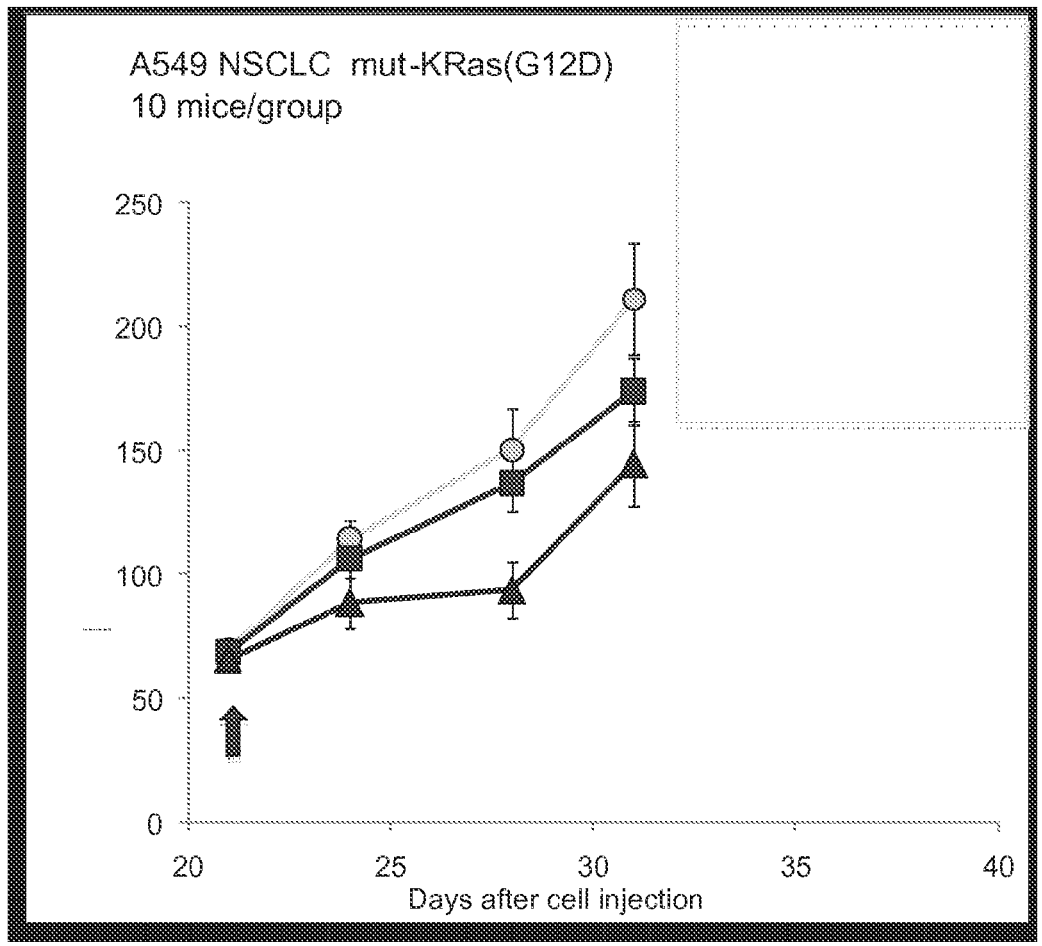
Figure 17:
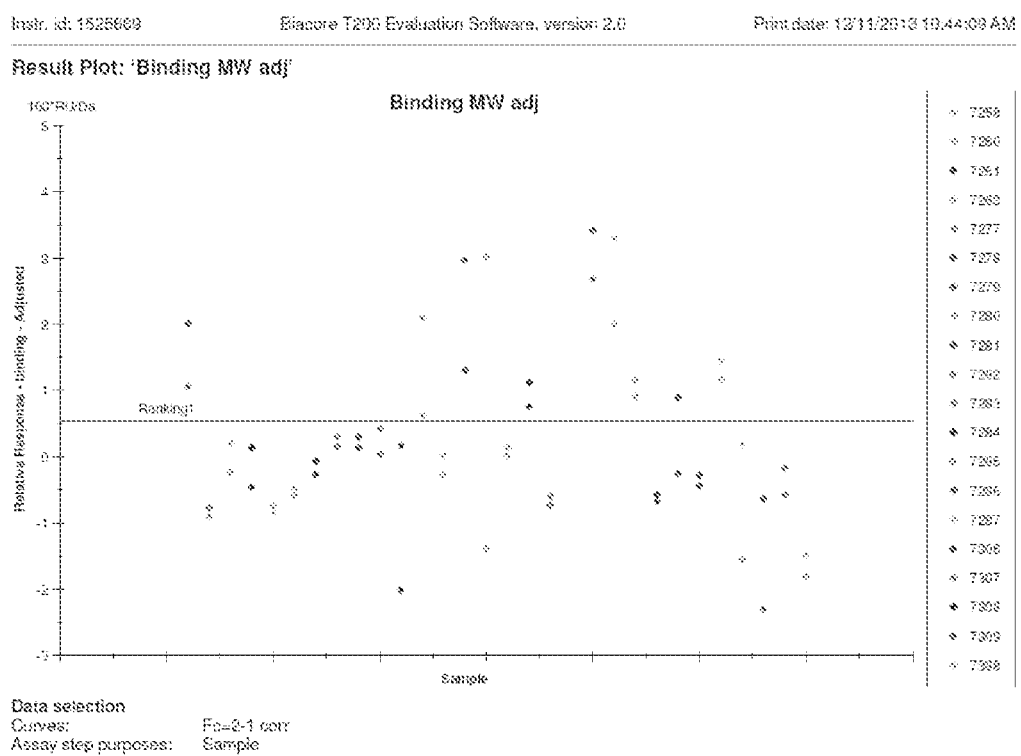
FIG. 17 is a graph depicting binding of selected compounds.
Figure 18:
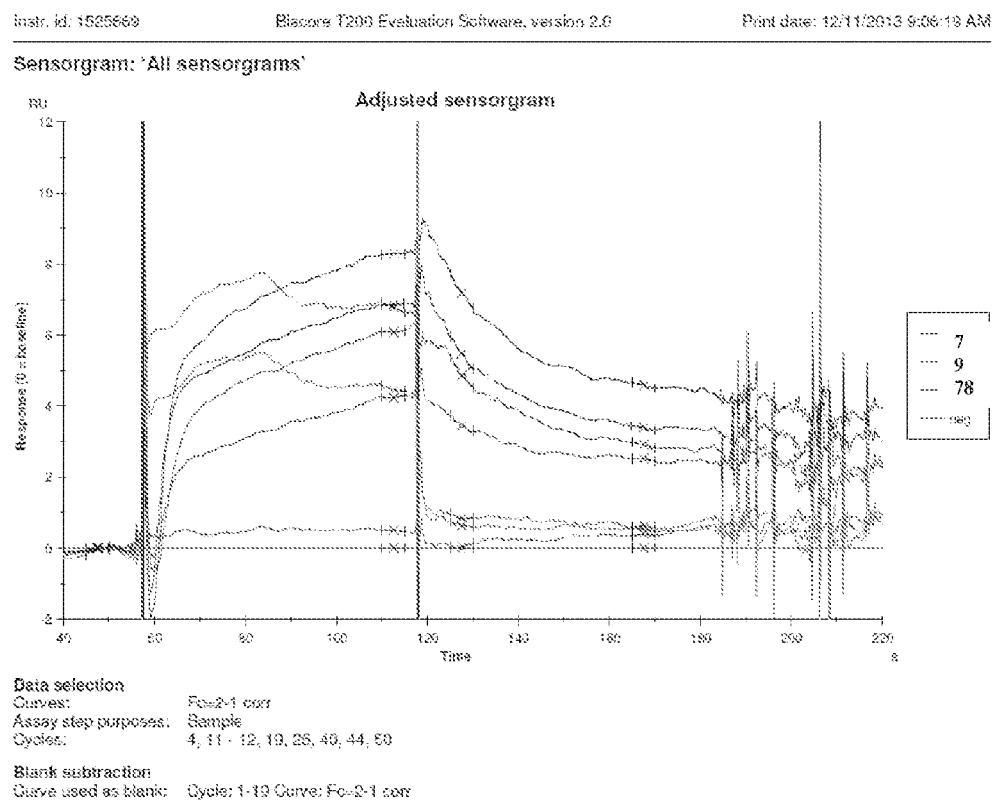
FIG. 18 is a sensogram comparing 3 selected compounds.
Figure 19:
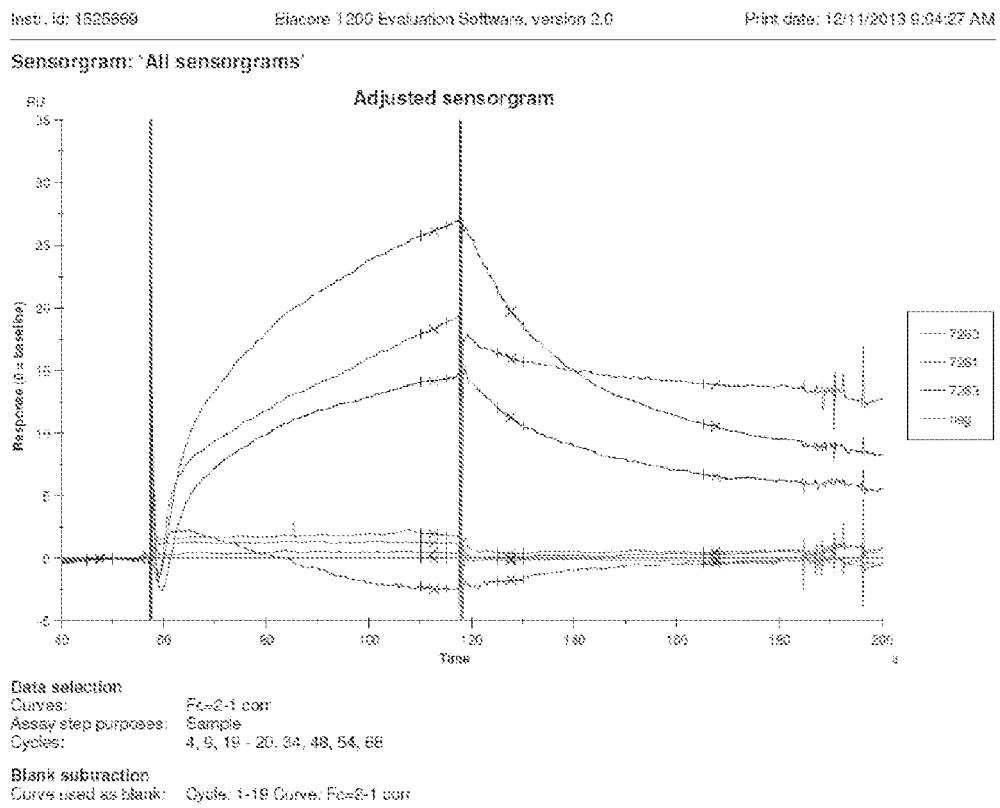
FIG. 19 is a sensogram comparing 3 selected compounds.

Immunoblots and Immunoprecipitations (FIGS. 3D, 14 and 15)

Cells were washed twice with ice-cold PBS and lysis buffer containing 50 mmol/L HEPES (pH 7.5), 50 mmol/L NaCl, 0.2 mmol/L NaF, 0.2 mmol/L sodium orthovanadate, 1 mmol/L phenylmethylsulfonyl fluoride, 20 µg/mL aprotinin, 20 µg/mL leupeptin, 1% NP40, and 0.25% sodium deoxycholate. Protein concentration was determined by bicinchoninic acid assay (Pierce Biotechnology) and 50 µg of cell lysate protein were boiled for 5 min with denaturing buffer containing 0.25 mol/L Tris (pH 6.8), 35% glycerol, 8% SDS, and 10% 2-mercaptoethanol, loaded on a 10% acrylamide/bisacrylamide gel, and separated by electrophoresis at 150 V for 40 min. Proteins were electrophoretically transferred to a nitrocellulose membrane; preincubated with a blocking buffer of 137 mmol/L NaCl, 2.7 mmol/L KCl, 897 mmol/L CaCl2, 491 mmol/L MgCl2, 3.4 mmol/L Na2HPO4, 593 mmol/L KH2PO4, and 5% bovine serum albumin; and incubated overnight with anti-phosphorylated Thr308-Akt, Ser473-Akt, anti-CRaf Ser 338 Mapk Thr202/Tyr204, p70 S6K Thr389 or anti-Akt. (Cell Signaling 1:1000), anti-CNKSR1 (Signal Transduction labs) anti-lamin A/C and anti-β-actin (Santa Cruz Biotechnology 1:2000Donkey anti-rabbit IgG peroxidase-coupled secondary antibody (GE Healthcare) was used for detection). For measurement of active RalA and RalB, Ral and RalB activation kits were used (Biorad). Band density was measured using the Renaissance chemiluminescence system on Kodak X-Omat Blue ML films (Eastman Kodak).

A commercially available docking package, GOLD (GOLD [3.2], CCDC: Cambridge, UK, 2007) was used to evaluate the docking of compounds 1-7 into the binding pocket, see e.g. Table 5. Other docking was performed using modeling algorithms with state-of-the-art commercial drug discovery software (Schrodinger suite). GLIDE was chosen as the docking algorithm used to select and optimize compounds, providing a GlideScore as a rough estimate of binding affinity that was used to rank and select the best compounds. Additionally, ligand-based approaches provided an alternative to structure based drug discovery. Ligand-based virtual screening methodologies can take into account shape and electrostatics (like ROCS) and the pharmacophoric features (acceptor, donor, hydrophobic, aromatic, etc.) of its functional groups. Inositol tetraphosphate (IP4) binding to the PH-domain of CNKSR1 provided a good starting point for shape screening. Both structure-based and ligand-based approaches were used to find novel compounds (Table 7) and to refine and improve lead compounds (Tables 8, and 9). SPR interaction analyses for Compounds 1 through 7 were performed with a Biacore 2000, using Biacore2000 Control Software v3.2 and BIAevaluation v4.1 analysis software (Biacore) as described in Mol Cancer Ther 7:2621 (2008). SPR interaction analyses of all other compounds was undertaken using a Biacore T100 with Control and Evaluation software kit.

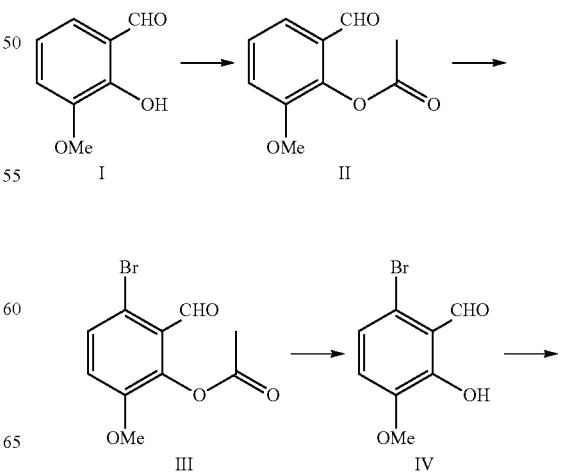

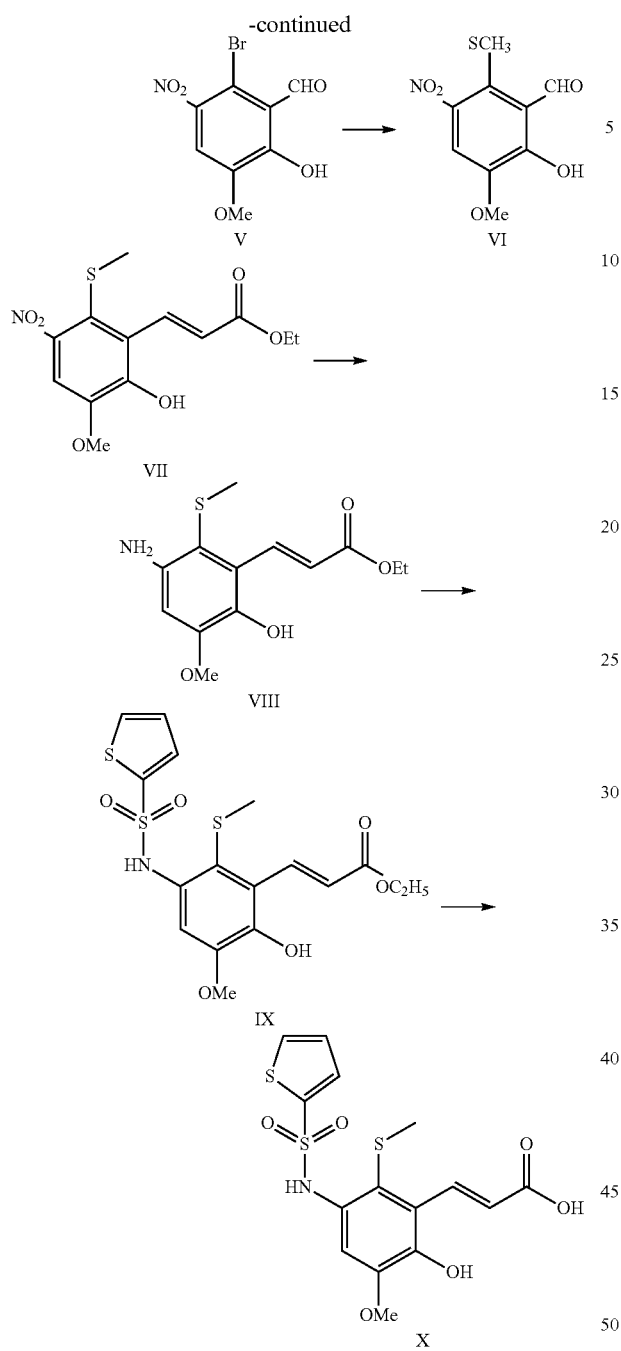
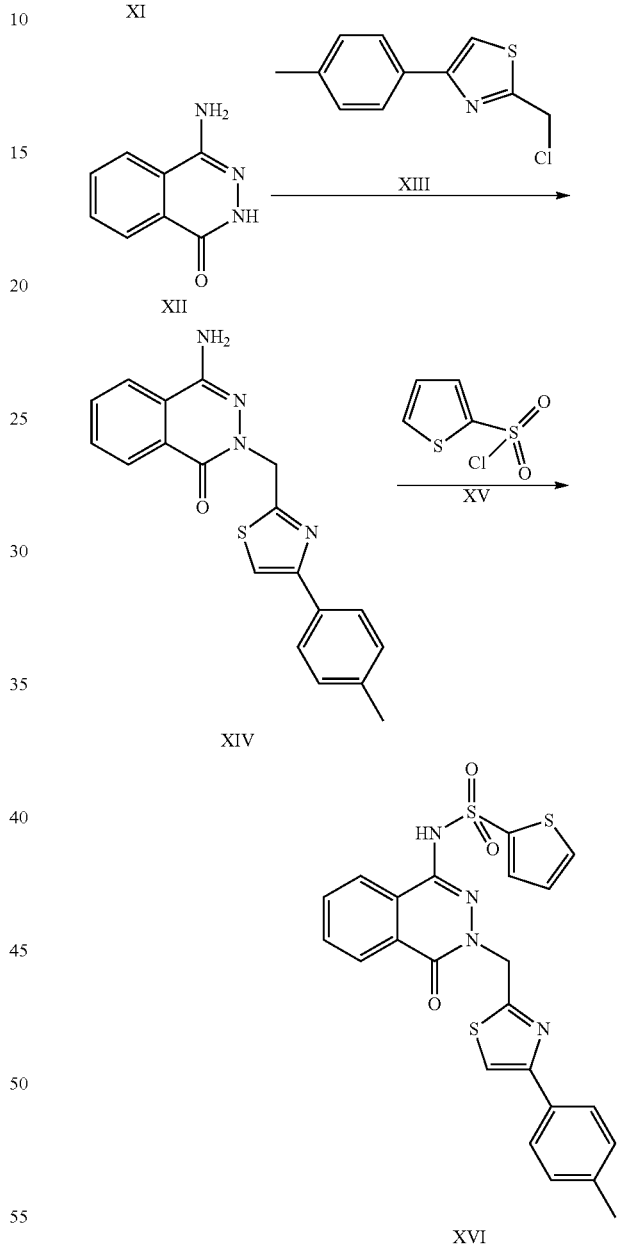

Compounds in accordance with embodiments may be produced as shown in Synthetic Scheme I. The 2-hydroxy-3-methoxybenzaldehyde I was protected by acylation to give compound II, then brominated to give compound III, and deprotected to give compound IV. Nitration of compound IV gave the nitrobenzene V, which reacted with an alkylsulfide to give the thiol ether VI. Wittig reaction of the aldehyde to the unsaturated ester VII followed by a reduction gave the aniline ester VIII (compound 107). The aniline was sulfonylated to give the thioamide IX (compound 103), and the ester hydrolyzed to give acid X (compound 104). Synthesis of analogs 103-110 may be readily prepared by a person of skill in the art of organic synthesis.

Compounds in accordance with embodiments may be produced as shown in Synthetic Scheme II. The methyl 2-cyanobenzoate XI was reacted with a hydrazine equivalent to give the azaisoquinolone XII. The azaisoquinoline was alkylated with the chloride XIII to give the coupled compound XIV. The free amine of the coupled compound XIV was sulfonylated with the acid chloride XV to give the thioamide XVI (compound 5). Synthesis of analogs may be readily prepared by a person of skill in the art of organic synthesis.

Synthetic Scheme III

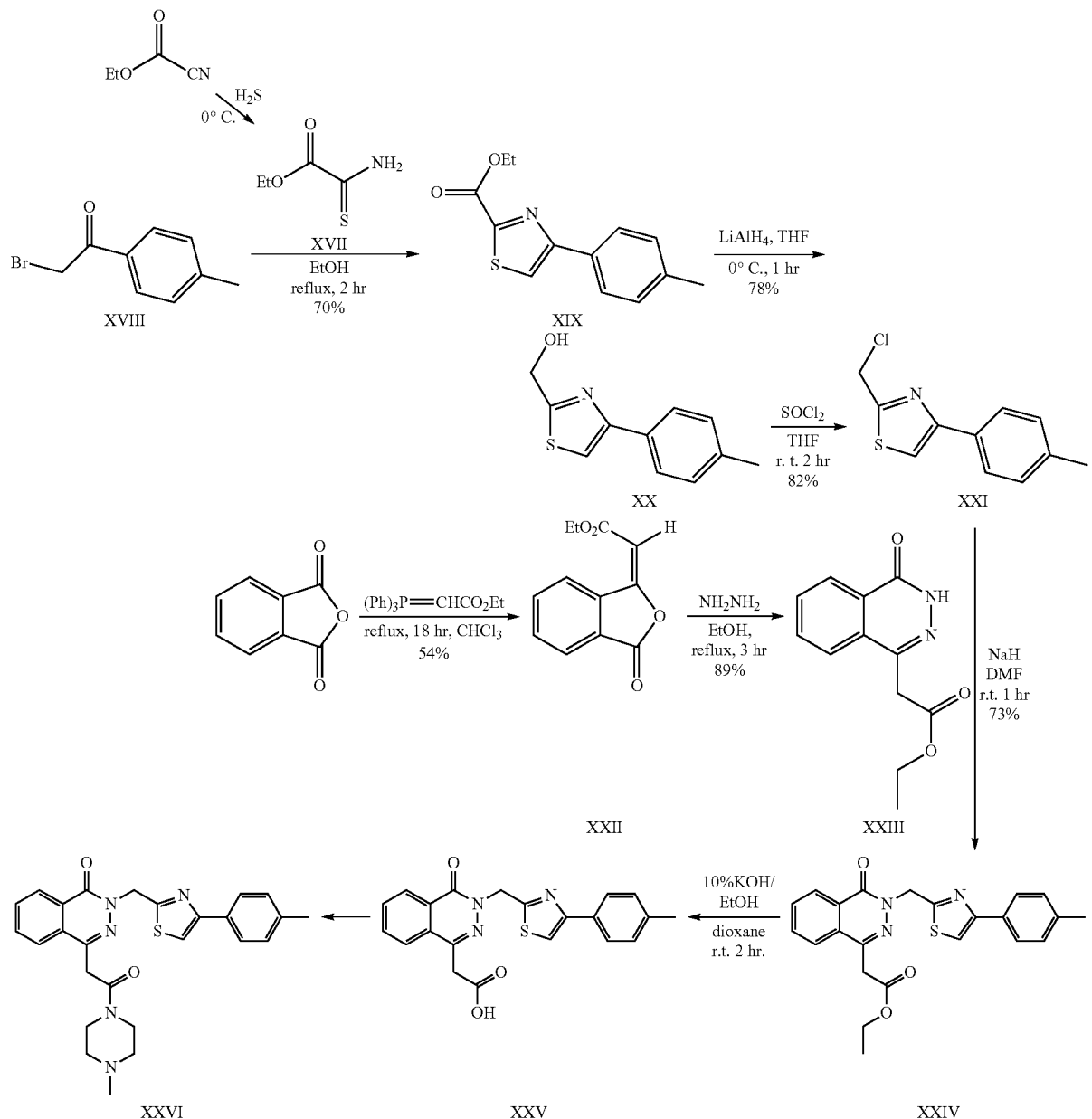

Compounds in accordance with embodiments may be produced as shown in Synthetic Scheme III. The bromoketone XVIII was reacted with the thioamide XVII in ethanol at reflux for two hours to give the thiazole ester XIX in 70% yield. The thiazole ester was reduced with lithium aluminum hydride in tetrahydrofuran at 0° C. for one hour to give the benzylic alcohol XX in 78% yield. The benzylic alcohyl was displaced to give benzylic chloride XXI in 82% yield by reaction with thionyl chloride in tetrahydrofuran at room temperature for two hours. Wittig reaction of phthalic anhydride in chloroform at reflux for 18 hours provided the unsaturated lactone XXII in 54% yield. Reaction of the unsaturated lactone with hydrazine in ethanol at reflux for three hours provided the oxoisoquinazaline XXIII. Coupling the oxoisoquinazaline XXIII with the benzyl chloride XXI was carried out in 73% yield by the action of sodium hydride in dimethylformamide at room temperature for one hour to give the N-alkylated isoquinazaline XXIV. Sapolification with 10% potassium hydroxide in ethanol and dioxane at room temperature for two hours gave the carboxylic acid XXV (compound 8). Amide formation with N-methylpiperazine gave the amide XXVI (compound 123). Compound 123: Molecular Formula $C_{26}H_{27}N_5O_2S$; Melting Point: 135.8° C.; NMR Analysis: $^1$H NMR (600 MHz, CDCl$_3$) δ 8.54 (d, J=7.8, 1H), 8.07 (d, J=7.9, 1H), 7.91 (t, J=7.6, 1H), 7.86 (t, J=7.5, 1H), 7.70 (d, J=7.7, 2H), 7.46 (s, 1H), 7.22 (d, J=7.7, 2H), 5.81 (s, 1H), 5.68 (s, 1H), 4.65 (d, J=12.1, 1H), 4.32 (d, J=12.0, 1H), 4.08 (s, 2H), 3.63 (s, 1H), 3.40 (d, J=10.7, 1H), 3.20 (s, 1H), 3.12 (s, 1H), 2.50 (s, 1H), 2.38 (d, J=14.8, 4H), 2.30 (s, 3H).

Synthetic Scheme IV

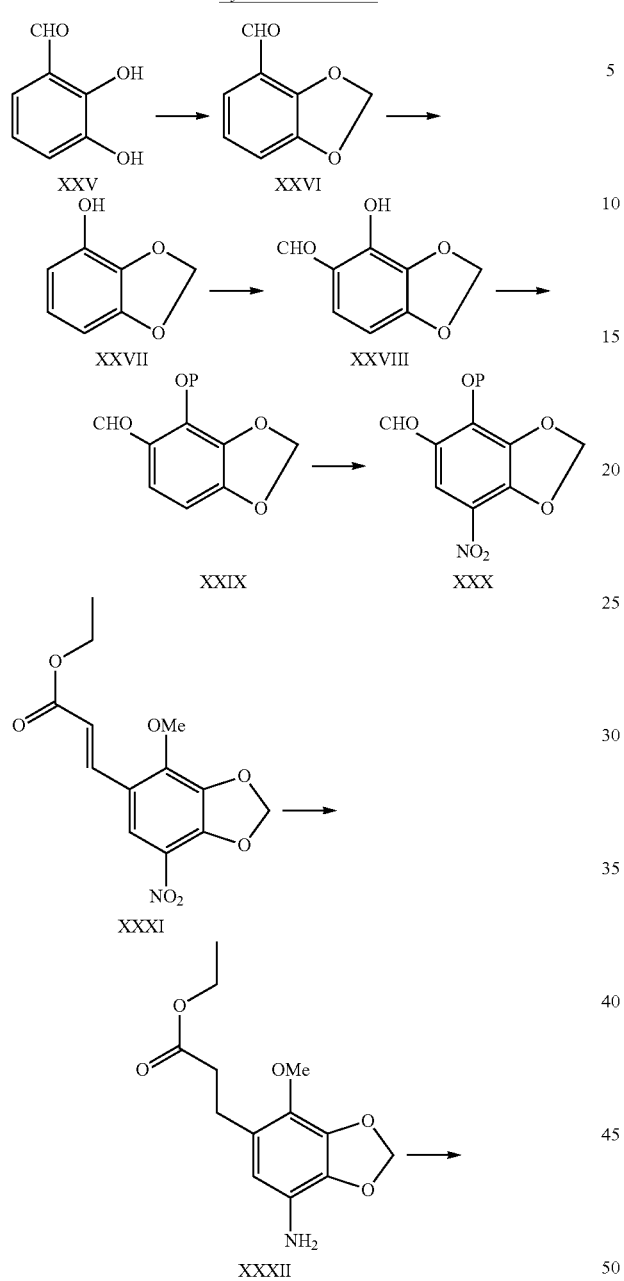

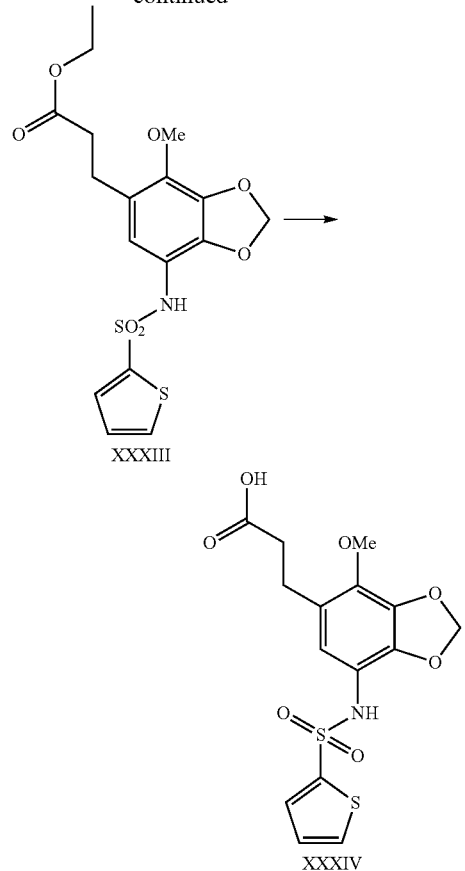

p = Bn

Compounds in accordance with embodiments may be produced as shown in Synthetic Scheme IV. 2,3-Dihydroxybenzaldehyde XXV was ketalized with formaldehyde to give the aryl dioxole XXVI, and the aldehyde oxidized to give the phenol XXVII. Acylation of the benzyl protected phenol with a formate equivalent gave the benzaldehyde XXIX, which was nitrated to give the nitrobenzaldehyde XXX. The aldehyde was conjugated to give the unsaturated ester XXXI, and reduced to the anilino ester XXII. Sulfonylation gave the thioamide XXXIII (compound 85), which was saponified to the carboxylic acid XXXIV (compound 83). Similarly, analogs 80-90 may be prepared by a person of skill in the art of organic synthesis. A person of skill in the art of organic synthesis can readily prepare other claimed compounds by processes similar to those in Schemes I-IV.

TABLE 5

| | | | Initial Screening Hits | | | |
|---|---|---|---|---|---|---|
| Cpd | Gold Fitness | Log P | Structure | Biacore KD (µM) | Mean IC$_{50}$ mut-KRAS (µM) | IC$_{50}$ mut-KRAS/ wtKRAS |
| 117 | 51.97 | 3.89 | | 0.7 ± 0.2 | 21.9 ± 5.7 | 0.9 |

TABLE 5-continued
Initial Screening Hits
| Cpd | Gold Fitness | Log P | Structure | Biacore KD (μM) | Mean IC$_{50}$ mut-KRAS (μM) | IC$_{50}$ mut-KRAS/wtKRAS |
|---|---|---|---|---|---|---|
| 118 | 56.06 | 4.28 | 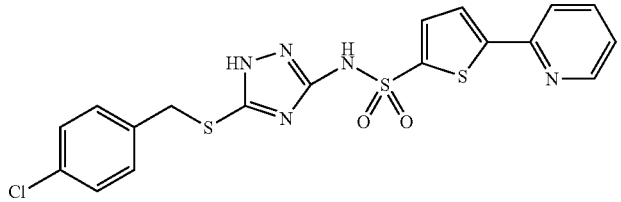 [SMILES: O=S(=O)(Nc1n[nH]c(SCc2ccc(Cl)cc2)n1)c1ccc(-c2ccccn2)s1] | 30.3 ± 1.2 | 49.3 ± 0.6 | 1.0 |
| 119 | 52.68 | 5.21 | 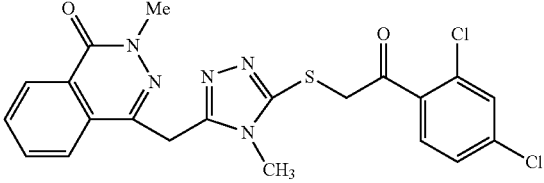 [SMILES: Cn1c(Cc2nn(C)c(=O)c3ccccc23)nnc1SCC(=O)c1ccc(Cl)cc1Cl] | 0.3 ± 0.1 | >50 | 1.0 |
| 120 | 52.33 | 2.26 | 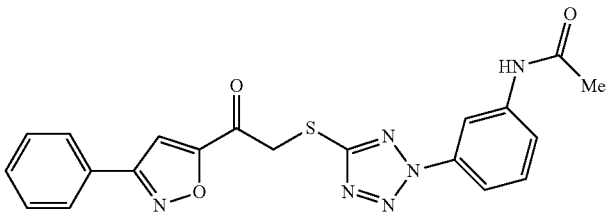 [SMILES: CC(=O)Nc1cccc(-n2nnc(SCC(=O)c3cc(-c4ccccc4)no3)n2)c1] | 3.3 ± 1.2 | 47.0 ± 5.2 | 0.9 |
| 121 | 51.98 | 3.43 | 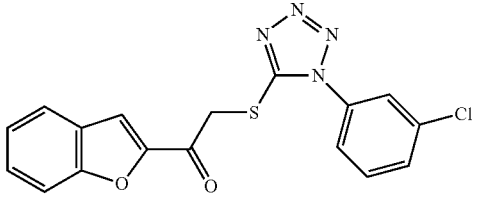 [SMILES: O=C(CSc1nnnn1-c1cccc(Cl)c1)c1cc2ccccc2o1] | 5.2 ± 2.6 | 46.7 ± 3.3 | 0.9 |
| 122 | 50.16 | 3.92 | 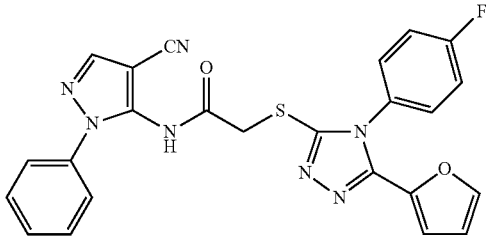 [SMILES: N#Cc1cnn(-c2ccccc2)c1NC(=O)CSc1nnc(-c2ccco2)n1-c1ccc(F)cc1] | 20.2 ± 0.8 | >50 | 1.0 |
| 7 | 51.72 | 4.57 | 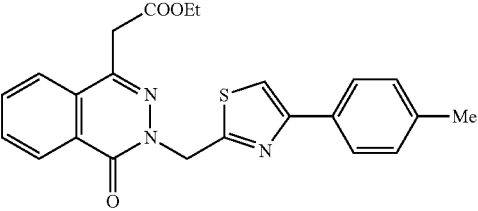 [SMILES: CCOC(=O)Cc1nn(Cc2nc(-c3ccc(C)cc3)cs2)c(=O)c2ccccc12] | 1.8 ± 0.6 | 23.9 ± 2.5 | 0.5 |

TABLE 6

Analogs of Compound 7

| Cpd | Structure | CNKS $K_D$ (μM) | AKT $K_D$ (μM) | NSCL cell line cytotoxicity* $IC_{50}$ (μM) | | Mouse Pharmkinetics (Iv) | |
|---|---|---|---|---|---|---|---|
| | | | | wt-KRAS | mut-KRAS | $t_{1/2}\beta$ min | Cl ml/min/Kg |
| 7 | 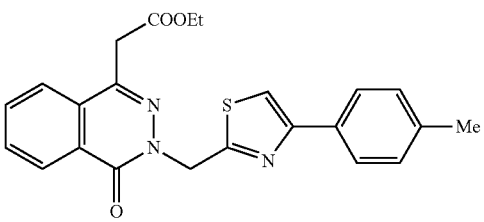 ethyl 2-(4-oxo-3-((4-p-tolylthiazol-2-yl)methyl)-3,4-dihydrophthalazin-1-yl)acetate | 3.2 | 17.3 | >100 | 49 | 3 UN | |
| 8 | 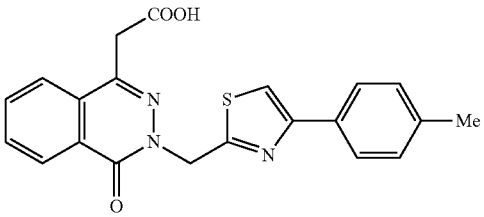 2-(4-oxo-3-((4-p-tolylthiazol-2-yl)methyl)-3,4-dihydrophthalazin-1-yl)acetic acid | >100 | 51.6 | >100 | >100 | 72 | 4745 |
| 9 | 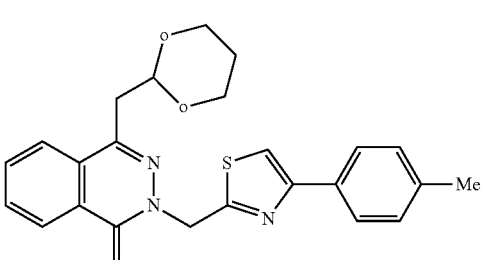 4-((1,3-dioxan-2-yl)methyl)-2-((4-p-tolylthiazol-2-yl)methyl)phthalazin-1(2H)-one | 0.026 | 66.3 | 55 | 25 | 260 | 133 |
| 10 | 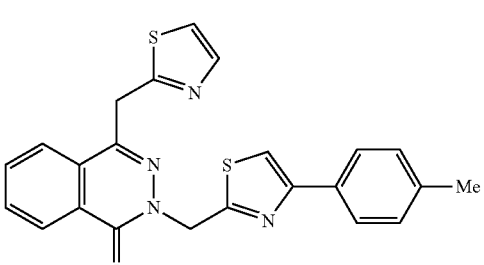 4-(thiazol-2-ylmethyl)-2-((4-p-tolylthiazol-2-yl)methyl)phthalazin-1(2H)-one | 4.12 | ND | 46 | 34 | 245 | 119 |

TABLE 6-continued

Analogs of Compound 7

| Cpd | Structure | CNKS $K_D$ (μM) | AKT $K_D$ (μM) | NSCL cell line cytotoxicity* $IC_{50}$ (μM) wt-KRAS | mut-KRAS | Mouse Pharmkinetics (Iv) $t_{1/2}\beta$ min | Cl ml/min/Kg |
|---|---|---|---|---|---|---|---|
| 11 | 4-((4-oxo-1,3-dioxolan-2-yl)methyl)-2-((4-p-tolylthiazol-2-yl)methyl)phthalazin-1(2H)-one | 0.27 | 2.53 | 56 | 45 | ND | ND |
| 78 | N-ethyl-2-(4-oxo-3-((4-p-tolylthiazol-2-yl)methyl)-3,4-dihydrophthalazin-1-yl)acetamide | 0.65 | 2.53 | na | na | 28 | 34 |
| 5 | N-(4-oxo-3-((4-p-tolylthiazol-2-yl)methyl)-3,4-dihydrophthalazin-1-yl)thiophene-2-sulfonamide | 51.3 | 34.2 | na | Na | na | na |
| 79 | 2-(4-oxo-3-((4-p-tolylthiazol-2-yl)methyl)-3,4-dihydrophthalazin-1-yl)acetaldehyde | 4.2 | ND | na | na | 35 | 30 |

TABLE 6-continued

Analogs of Compound 7

| Cpd | Structure | CNKS $K_D$ (µM) | AKT $K_D$ (µM) | NSCL cell line cytotoxicity* IC$_{50}$ (µM) | | Mouse Pharmkinetics (Iv) | |
|---|---|---|---|---|---|---|---|
| | | | | wt-KRAS | mut-KRAS | $t_{1/2}\beta$ min | Cl ml/min/Kg |
| 80 | 4-((3,6-dihydro-2H-1,4-oxazin-2-yl)methyl)-2-((4-p-tolylthiazol-2-yl)methyl)phthalazin-1(2H)-one | >100 | ND | na | na | ND | ND |
| 81 | 3-(2-(4-oxo-3-((4-p-tolylthiazol-2-yl)methyl)-3,4-dihydrophthalazin-1-yl)acetamido)propanamide | 109 | ND | na | na | na | na |
| 82 | N-(2-amino-2-oxoethyl)-2-(4-oxo-3-((4-p-tolylthiazol-2-yl)methyl)-3,4-dihydrophthalazin-1-yl)acetamide | ND | ND | na | na | na | na |

TABLE 6-continued

Analogs of Compound 7

| Cpd | Structure | CNKS $K_D$ (μM) | AKT $K_D$ (μM) | NSCL cell line cytotoxicity* $IC_{50}$ (μM) wt-KRAS | NSCL cell line cytotoxicity* $IC_{50}$ (μM) mut-KRAS | Mouse Pharmkinetics (Iv) $t_{1/2}\beta$ min | Mouse Pharmkinetics (Iv) Cl ml/min/Kg |
|---|---|---|---|---|---|---|---|
| 123 | 4-(2-(4-methylpiperazin-1-yl)-2-oxoethyl)-2-((4-p-tolylthiazol-2-yl)methyl)phthalazin-1(2H)-one | ND | ND | na | na | 327 | 31 |

ND no binding determined;
iv intravenous;
UN unstable is plasma;
* mean of 3 wt-KRAS and 3 mut-KRAS;
no not analyzed

TABLE 7

Curated Diversity Set

| Compound | CNK KD μM | U-Value | AKT KD μM | U-Value | $IC_{50}$ mut-KRAS | $IC_{50}$ WT-KRAS |
|---|---|---|---|---|---|---|
| 61 | $1.01 * 10^{-6}$ | 12 | $1.28 * 10^{-6}$ | 43 | >100 | >100 |
| 34 | ND | 95 | Bound | Bound | | |
| 67 | $1.96 * 10^{-4}$ | 43 | Bound | Bound | | |
| 64 | ND | 95 | Bound | Bound | | |
| 66 | ND | 73 | Bound | Bound | | |
| 76 | $1.13 * 10^{-6}$ | 20 | Bound | Bound | >100 | >100 |
| 12 | $3.64 * 10^{-6}$ | 4 | Bound | Bound | 17 | 12 |
| 56 | $5.34 * 10^{-6}$ | 2 | $4.74 * 10^{-4}$ | 2 | >100 | >100 |

ND = no binding determined

TABLE 8

Analogs modeled from Second Series Hits

| Structure | CV No | Mol WT | CNK $K_D$ (μM) | PLE $K_D$ (μM) | AKT $K_D$ (μM) | IUPAC Name |
|---|---|---|---|---|---|---|
| | 83 | 385 | na | na | na | 3-(4-methoxy-7-(thiophene-2-sulfonamido)benzo[d][1,3]dioxol-5-yl)propanoic acid |

TABLE 8-continued

Analogs modeled from Second Series Hits

| Structure | CV No | Mol WT | CNK $K_D$ (μM) | PLE $K_D$ (μM) | AKT $K_D$ (μM) | IUPAC Name |
|---|---|---|---|---|---|---|
| 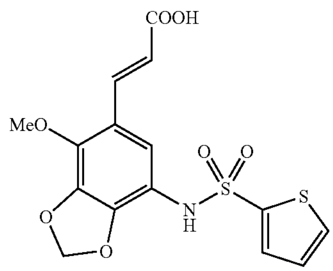 | 84 | 383 | No binding | na | No binding | (E)-3-(4-methoxy-7-(thiophene-2-sulfonamido)benzo[d][1,3]dioxol-5-yl)acrylic acid |
| 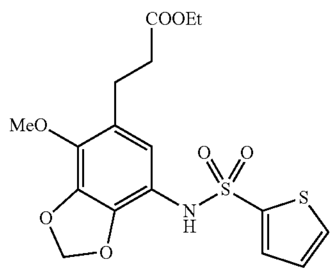 [SMILES: COc1c(CCC(=O)O)cc(NS(=O)(=O)c2cccs2)c2c1OCO2] | 85 | 413 | >500 | na | >500 | ethyl 3-(4-methoxy-7-(thiophene-2-sulfonamido)benzo[d][1,3]dioxol-5-yl)propanoate |
| 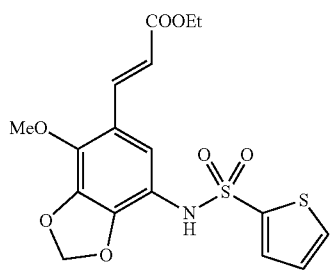 [SMILES: CCOC(=O)/C=C/c1cc(NS(=O)(=O)c2cccs2)c2c(c1OC)OCO2] | 86 | 411 | 123 | na | >500 | (E)-ethyl 3-(4-methoxy-7-(thiophene-2-sulfonamido)benzo[d][1,3]dioxol-5-yl)acrylate |
| 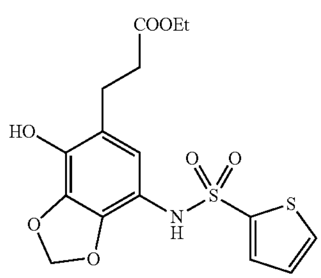 | 87 | 399 | na | na | na | ethyl 3-(4-hydroxy-7-(thiophene-2-sulfonamido)benzo[d][1,3]dioxol-5-yl)propanoate |
| 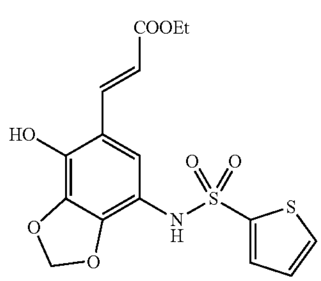 [SMILES: O=C(O)/C=C/c1cc(NS(=O)(=O)c2cccs2)c2c(c1O)OCO2] | 88 | 397 | 0.186 | 261.3 | 75.2 | (E)-ethyl 3-(4-hydroxy-7-(thiophene-2-sulfonamido)benzo[d][1,3]dioxol-5-yl)acrylate |

TABLE 8-continued

Analogs modeled from Second Series Hits

| Structure | CV No | Mol WT | CNK $K_D$ (μM) | PLE $K_D$ (μM) | AKT $K_D$ (μM) | IUPAC Name |
|---|---|---|---|---|---|---|
| (structure) | 89 | 369 | 3.37 | na | ND | (E)-3-(4-hydroxy-7-(thiophene-2-sulfonamido)benzo[d][1,3]dioxol-5-yl)acrylic acid |
| (structure) | 90 | 371 | ND | na | ND | 3-(4-hydroxy-7-(thiophene-2-sulfonamido)benzo[d][1,3]dioxol-5-yl)propanoic acid |
| (structure) | 103 | 429.53 | 0.157 | 300 | 330 | ethyl (2E)-3-[2-hydroxy-3-methoxy-6-(methylsulfanyl)-5-(thiopliene-2-sulfonamido)phenyl]prop-2-enoate |
| (structure) | 104 | 401.48 | 1.56 | na | 4.8 | (2E)-3-[2-hydroxy-3-methoxy-6-(methylsulfanyl)-5-(thiophene-2-sulfonamido)phenyl]prop-2-enoic acid |
| (structure) | 105 | 415.51 | 2.86 | na | 6.22 | ethyl (2E)-3-[2,3-dihydroxy-6-(methylsulfanyl)-5-(thiophene-2-sulfonamido)phenyl]prop-2-enoate |
| (structure) | 106 | 387.45 | 0.614 | na | 13.5 | (2E)-3-[2,3-dihydroxy-6-(methylsulfanyl)-5-(thiopliene-2-sulfonamido)phenyl]prop-2-enoic acid |

TABLE 8-continued

Analogs modeled from Second Series Hits

| Structure | CV No | Mol WT | CNK $K_D$ (µM) | PLE $K_D$ (µM) | AKT $K_D$ (µM) | IUPAC Name |
|---|---|---|---|---|---|---|
| 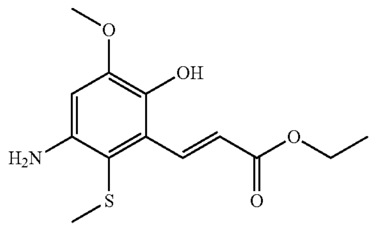 [SMILES: CCOC(=O)/C=C/c1c(O)c(OC)cc(N)c1SC] | 107 | 283.34 | 125 | na | 286 | ethyl (E)-3-(5-amino-2-hydroxy-3-methoxy-6-methylsulfanylphenyl)prop-2-enoate |
| 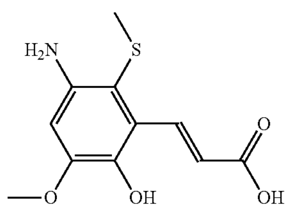 [SMILES: COc1cc(N)c(SC)c(/C=C/C(=O)O)c1O] | 108 | 255.29 | 72.5 | na | 133 | (2E)-3-[3-amino-6-hydroxy-5-methoxy-2-(methylsulfanyl)phenyl]prop-2-enoic acid |
| 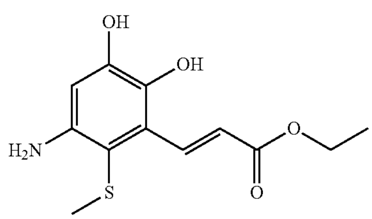 [SMILES: CCOC(=O)/C=C/c1c(O)c(O)cc(N)c1SC] | 109 | 269.32 | 19.2 | na | 140 | ethyl (2E)-3-[3-amino-5,6-dihydroxy-2-(methylsulfanyl)phenyl]prop-2-enoate |
| 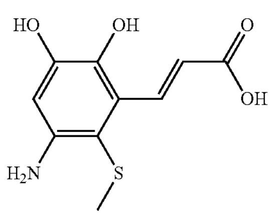 [SMILES: CSc1c(N)cc(O)c(O)c1/C=C/C(=O)O] | 110 | 241.26 | ND | na | 178 | (2E)-3-[3-amino-5,6-dihydroxy-2-(methylsulfanyl)phenyl]prop-2-enoic acid |
| 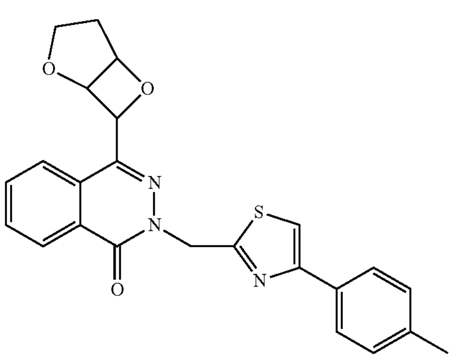 [SMILES: Cc1ccc(-c2csc(Cn3nc(C4OC5CCOC54)c4ccccc4c3=O)n2)cc1] | 124 | 431 | | | | |

TABLE 8-continued

Analogs modeled from Second Series Hits

| Structure | CV No | Mol WT | CNK K$_D$ (μM) | PLE K$_D$ (μM) | AKT K$_D$ (μM) | IUPAC Name |
|---|---|---|---|---|---|---|
| 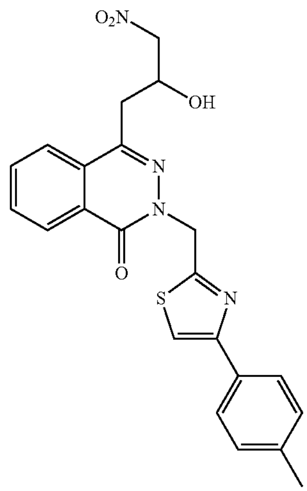 | 125 | 436 | | | | |
| 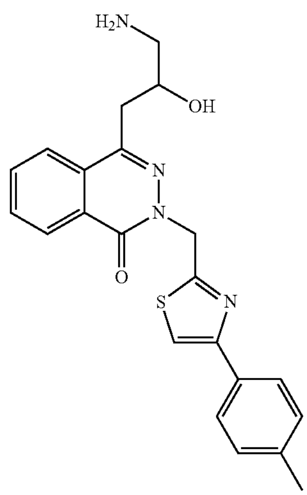 [SMILES: Cc1ccc(-c2csc(Cn3nc(CC(O)C[N+](=O)[O-])c4ccccc4c3=O)n2)cc1] | 126 | 406 | | | | |
| 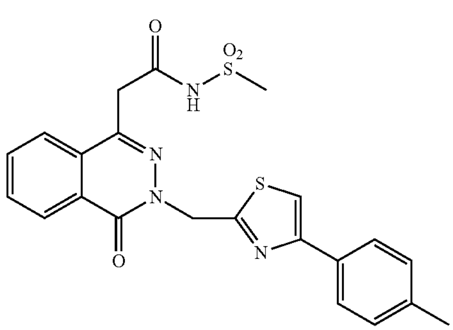 [SMILES: Cc1ccc(-c2csc(Cn3nc(CC(=O)NS(C)(=O)=O)c4ccccc4c3=O)n2)cc1] | 127 | 469 | | | | |

TABLE 8-continued

Analogs modeled from Second Series Hits

| Structure | CV No | Mol WT | CNK $K_D$ (μM) | PLE $K_D$ (μM) | AKT $K_D$ (μM) | IUPAC Name |
|---|---|---|---|---|---|---|
| 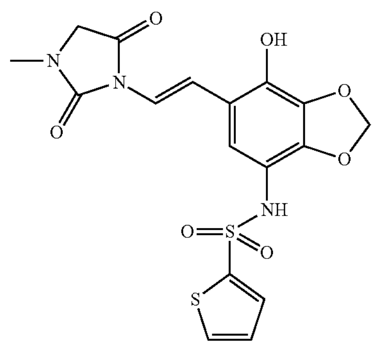 [SMILES: CN1CC(=O)N(/C=C/c2cc(NS(=O)(=O)c3cccs3)c3c(c2O)OCO3)C1=O] | 91 | 437 | | | | |
| 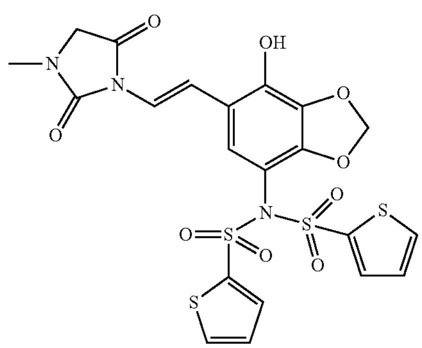 [SMILES: CN1CC(=O)N(/C=C/c2cc(N(S(=O)(=O)c3cccs3)S(=O)(=O)c3cccs3)c3c(c2O)OCO3)C1=O] | 128 | 568 | | | | |
| 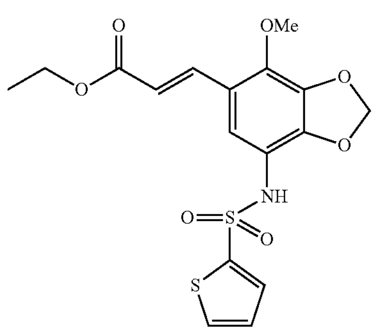 [SMILES: CCOC(=O)/C=C/c1cc(NS(=O)(=O)c2cccs2)c2c(c1OC)OCO2] | 129 | 411 | | | | |
| 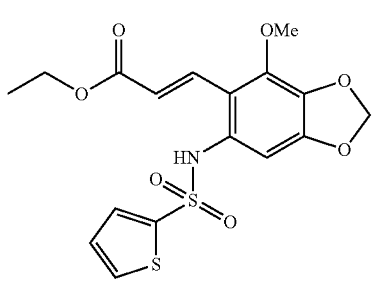 [SMILES: CCOC(=O)/C=C/c1c(NS(=O)(=O)c2cccs2)cc2c(c1OC)OCO2] | 130 | 411 | | | | |

TABLE 8-continued
Analogs modeled from Second Series Hits
| Structure | CV No | Mol WT | CNK K$_D$ (μM) | PLE K$_D$ (μM) | AKT K$_D$ (μM) | IUPAC Name |
|---|---|---|---|---|---|---|
| 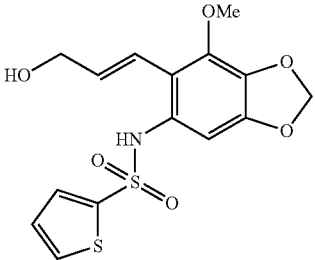 [SMILES: COc1c(/C=C/CO)c(NS(=O)(=O)c2cccs2)cc2c1OCO2] | 131 | 369 | | | | |
| 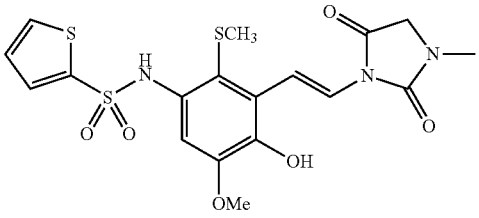 [SMILES: COc1cc(NS(=O)(=O)c2cccs2)c(SC)c(/C=C/N2C(=O)CN(C)C2=O)c1O] | 132 | 470 | | | | |
| 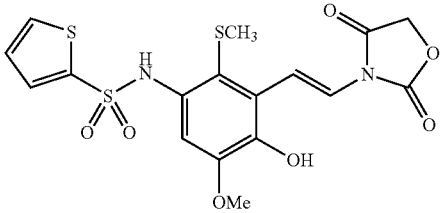 [SMILES: COc1cc(NS(=O)(=O)c2cccs2)c(SC)c(/C=C/N2C(=O)COC2=O)c1O] | 133 | 457 | | | | |
| 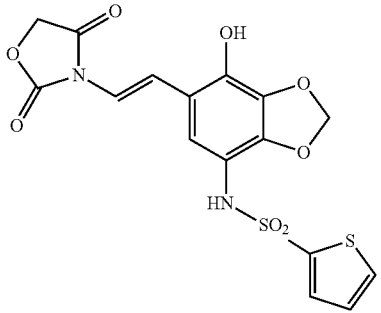 [SMILES: O=C1COC(=O)N1/C=C/c1cc(NS(=O)(=O)c2cccs2)c2c(c1O)OCO2] | 100 | 424 | | | | |

TABLE 9

| Cpd | | Mol WT | Log P | r_qp_Q PlogHE RG | r_qp_QP PCaco | r_qp_% Human Oral Absorption |
|---|---|---|---|---|---|---|
| 91 | (E)-N-(7-hydroxy-6-(2-(3-methyl-2,5-dioxoimidazolidin-1-yl)vinyl)benzo[d][1,3]dioxol-4-yl)thiophene-2-sulfonamide | 436.45 | 0.85 | −5.26 | 74.60 | 66.54 |
| 92 | (E)-N-(6-(2-(5-chloro-3-methyl-2-oxo-2,3-dihydro-1H-imidazol-1-yl)vinyl)-7-hydroxybenzo[d][1,3]dioxol-4-yl)thiophene-2-sulfonamide | 454.89 | 2.44 | −5.48 | 203.24 | 81.64 |
| 93 | (E)-N-(7-hydroxy-6-(2-(3-methyl-2-oxoimidazolidin-1-yl)vinyl)benzo[d][1,3]dioxol-4-yl)thiophene-2-sulfonamide | 422.46 | 1.02 | −5.19 | 242.80 | 80.98 |

TABLE 9-continued

| Cpd | | Mol WT | Log P | r_qp_Q PlogHE RG | r_qp_QP PCaco | r_qp_% Human Oral Absorption |
|---|---|---|---|---|---|---|
| 94 | (E)-N-(7-hydroxy-6-(2-(4-methyl-2-oxothiazol-3(2H)-yl)vinyl)benzo[d][1,3]dioxol-4-yl)thiophene-2-sulfonamide | 437.5 | 2.44 | −5.07 | 222.80 | 80.30 |
| 95 | (E)-N-(6-(2-(2,5-dioxo-2,5-dihydro-1H-pyrrol-1-yl)vinyl)-7-hydroxybenzo[d][1,3]dioxol-4-yl)thiophene-2-sulfonamide | 419.41 | 1.53 | −5.30 | 62.10 | 64.54 |
| 96 | (E)-N-(6-(2-(4-chloro-2-oxothiazol-3(2H)-yl)vinyl)-7-hydroxybenzo[d][1,3]dioxol-4-yl)thiophene-2-sulfonamide | 457.92 | 3.19 | −5.16 | 219.25 | 81.09 |

TABLE 9-continued

| Cpd | Structure | Mol WT | Log P | r_qp_Q PlogHE RG | r_qp_QP PCaco | r_qp_% Human Oral Absorption |
|---|---|---|---|---|---|---|
| 97 | (E)-N-(6-(2-(5-chloro-4-methyl-2-oxo-2,3-dihydro-1H-imidazol-1-yl)vinyl)-7-hydroxybenzo[d][1,3]dioxol-4-yl)thiophene-2-sulfonamide | 454.89 | 2.52 | −5.19 | 134.92 | 76.65 |
| 98 | (E)-N-(6-(2-(5-ethyl-2-oxo-2,3-dihydro-1H-imidazol-1-yl)vinyl)-7-hydroxybenzo[d][1,3]dioxol-4-yl)thiophene-2-sulfonamide | 434.47 | 1.88 | −5.44 | 97.28 | 72.29 |
| 99 | (E)-N-(6-(2-(2,5-dioxo-2,5-dihydro-1H-pyrrol-3-ylimino)ethyl)-7-hydroxybenzo[d][1,3]dioxol-4-yl)thiophene-2-sulfonamide | 434.43 | 0.56 | −4.34 | 21.39 | 51.02 |

TABLE 9-continued

| Cpd | | Mol WT | Log P | r_qp_Q PlogHE RG | r_qp_QP PCaco | r_qp_% Human Oral Absorption |
|---|---|---|---|---|---|---|
| 100 | (E)-N-(6-(2-(2,4-dioxooxazolidin-3-yl)vinyl)-7-hydroxybenzo[d][1,3]dioxol-4-yl)thiophene-2-sulfonamide | 423.4 | 1.1 | −4.64 | 60.93 | 59.71 |
| 101 | (E)-1-(2-(4-hydroxy-7-(thiophene-2-sulfonamido)benzo[d][1,3]dioxol-5-yl)vinyl)-1H-1,2,3-triazole-5-carboxamide | 434.43 | 0.17 | −5.46 | 14.91 | 34.24 |
| 102 | (E)-N-(6-(2-(1,3-dioxan-2-yl)vinyl)-7-hydroxybenzo[d][1,3]dioxol-4-yl)thiophene-2-sulfonamide | 410.44 | | | | |

TABLE 9-continued

| Cpd | | Mol WT | Log P | r_qp_Q PlogHE RG | r_qp_QP PCaco | r_qp_% Human Oral Absorption |
|---|---|---|---|---|---|---|
| 111 | (E)-N-(3-(2-(3,5-dioxo-1,2,4-oxadiazolidin-4-yl)vinyl)-4-hydroxy-5-methoxy-2-(methylthio)phenyl)thiophene-2-sulfonamide | 456.5 | 1.41 | −5.28 | 24.63 | |
| 112 | (E)-N-(4-hydroxy-5-methoxy-2-(methylthio)-3-(2-(2,4,5-trioxoimidazolidin-1-yl)vinyl)phenyl)thiophene-2-sulfonamide | 467.5 | 1.19 | −5.18 | 17.43 | |
| 113 | (E)-N-(3-(2-(2,4-dimethyl-5-oxo-2,5-dihydro-1H-pyrazol-1-yl)vinyl)-4-hydroxy-5-methoxy-2-(methylthio)phenyl)thiophene-2-sulfonamide | 466.6 | 2.73 | −5.264 | 245.69 | |
| 114 | (E)-5-(2-hydroxy-3-methoxy-6-(methylthio)-5-(thiophene-2-sulfonamido)styryl)-1,3,4-oxadiazole-2-carboxamide | 467.5 | 1.96 | −5.412 | 16.29 | |

TABLE 9-continued

| Cpd | | Mol WT | Log P | r_qp_Q PlogHERG | r_qp_QP PCaco | r_qp_% Human Oral Absorption |
|---|---|---|---|---|---|---|
| 115 | 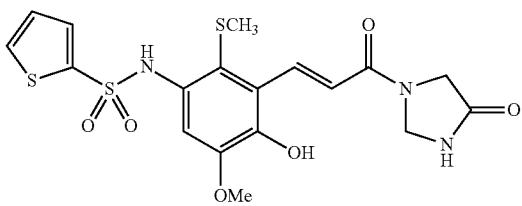 (E)-N-(4-hydroxy-5-methoxy-2-(methylthio)-3-(3-oxo-3-(4-oxoimidazolidin-1-yl)prop-1-enyl)phenyl)thiophene-2-sulfonamide | 468.6 | 1.56 | −4.21 | | 23.28 |
| 116 | 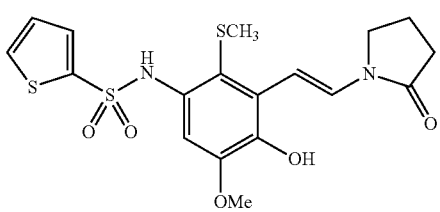 (E)-N-(4-hydroxy-5-methoxy-2-(methylthio)-3-(2-(2-oxopyrrolidin-1-yl)vinyl)phenyl)thiophene-2-sulfonamide | 439.6 | 2.25 | −5.22 | | 242.52 |

The table below shows results from a Proliferation Assay and Surface Plasmon Resonance data for selected compounds.

Summary Table 10 for CNKSR1 inhibitors

| | Proliferation Assay (IC50) μM | | | | | Surface Plasmon Resonance RU * 100/Da | | | |
|---|---|---|---|---|---|---|---|---|---|
| | KRAS mutant cell lines | | | KRAS wildtype cell lines | | CNKSR1 11 26 13 | | CNKSR1 12 09 13 | |
| compound | A549 | H1373 | H2122 | H1975 | H226 | binding | stability | binding | stability |
| DMSO | >100 | >100 | | >100 | >100 | $a$ | | −0.845 | −0.305 |
| 5 | 90 | >100 | | 80 | >100 | | | −0.695 | −0.158 |
| 7 | 15 | >100 | | 45 | >100 | 5.019 | 0.761 | 0.205 | 0.798 |
| 9 | 42 | >100 | | 100 | >100 | 3.979 | 1.960 | 0.936 | 1.183 |
| 78 | 25 | 45 | | 60 | 60 | | | 0.224 | −0.065 |
| 81 | 100 | 95 | | 80 | >100 | | | 0.316 | 0.154 |
| 82 | 51 | 65 | | 70 | >100 | | | 1.304 | 0.544 |
| 84 | >100 | >100 | | >100 | >100 | | | −1.473 | −0.196 |
| 85 | >100 | >100 | | >100 | >100 | | | 1.026 | 1.515 |
| 86 | >100 | >100 | | >100 | >100 | | | −0.807 | −0.197 |
| 88 | >100 | >100 | | >100 | >100 | | | 0.817 | 1.138 |
| 89 | >100 | >100 | | >100 | >100 | | | 1.350 | 1.401 |
| 90 | >100 | >100 | | >100 | >100 | | | −7.809 | −3.766 |
| 91 | >100 | >100 | | >100 | >100 | −1.867 | 0.288 | | |
| 100 | >100 | >100 | | >100 | >100 | −1.240 | −0.026 | | |
| 103 | 75 | >100 | | >100 | >100 | | | 2.635 | 3.148 |
| 104 | 60 | 82 | | >100 | 75 | | | 2.132 | 2.049 |
| 105 | 100 | 42 | | >100 | 70 | | | −0.676 | −0.197 |
| 106 | 55 | 58 | | >100 | 70 | | | −0.928 | 0.511 |
| 107 | 45 | 45 | | 95 | 60 | | | −0.174 | −0.083 |
| 108 | 30 | 38 | | 100 | 55 | | | −0.024 | 0.056 |
| 109 | >100 | >100 | | >100 | >100 | | | 1.527 | 0.168 |
| 110 | 27 | 28 | | >100 | 65 | | | 0.217 | 0.032 |
| 124 | 50 | 50 | | >100 | 95 | | | −0.369 | −0.053 |
| 125 | 38 | 60 | | 40 | 65 | | | −0.380 | −0.127 |
| 126 | 27 | 16 | | 27 | 19 | | | −0.166 | −0.031 |
| 127 | >100 | >100 | | >100 | >100 | | | 3.050 | 2.868 |

Summary Table 10 for CNKSR1 inhibitors

| | Proliferation Assay (IC50) μM | | | | | Surface Plasmon Resonance RU * 100/Da | | | |
|---|---|---|---|---|---|---|---|---|---|
| | KRAS mutant cell lines | | | KRAS wildtype cell lines | | CNKSR1 11 26 13 | | CNKSR1 12 09 13 | |
| compound | A549 | H1373 | H2122 | H1975 | H226 | binding | stability | binding | stability |
| 128 | >100 | >100 | | >100 | >100 | 1.409 | 0.456 | −0.541 | −0.304 |
| 129 | >100 | >100 | | >100 | >100 | −0.133 | −0.041 | | |
| 130 | 3 | >100 | | >100 | >100 | −0.251 | −0.180 | | |
| 131 | 2 | >100 | | >100 | >100 | −0.789 | −0.044 | | |
| 132 | 72 | 60 | | >100 | 60 | 0.457 | 0.906 | | |
| 133 | >100 | >100 | | >100 | 95 | −1.537 | −0.123 | | |
| 134 | >100 | >100 | | >100 | >100 | 0.383 | 0.152 | | |
| 135 | >100 | >100 | | >100 | >100 | −0.005 | 0.046 | | |
| 136 | 45 | >100 | | >100 | >100 | −2.252 | −0.079 | 0.072 | 0.065 |
| 137 | 100 | >100 | | >100 | >100 | −0.712 | 0.076 | | |
| 138 | >100 | >100 | | >100 | >100 | 1.874 | −0.085 | | |
| 139 | >100 | >100 | | >100 | >100 | 3.026 | 0.151 | | |
| 140 | >100 | >100 | | >100 | >100 | 4.572 | 0.065 | | |
| 141 | >100 | >100 | | >100 | >100 | 4.246 | 0.239 | | |
| 142 | >100 | >100 | | 23 | >100 | 2.690 | 0.124 | | |
| 143 | >100 | >100 | | >100 | >100 | 2.620 | 0.013 | | |
| 144 | >100 | >100 | | 75 | >100 | 0.205 | 0.122 | | |
| 145 | >100 | >100 | | >100 | >100 | 2.973 | 0.108 | | |
| 146 | >100 | >100 | | >100 | >100 | 2.842 | 0.017 | | |
| 147 | 75 | >100 | | >100 | >100 | 3.085 | −0.087 | | |
| 148 | 47 | 77 | | >100 | 75 | 2.304 | 0.167 | | |
| 149 | 80 | 40 | | >100 | >100 | 4.228 | 1.520 | | |
| 150 | >100 | 100 | | >100 | >100 | 3.695 | 0.236 | | |
| 151 | >100 | >100 | | >100 | >100 | 0.585 | 0.485 | | |
| 152 | >100 | >100 | | 19 | >100 | 4.808 | 0.458 | | |
| 153 | 20 | 45 | | 11 | 72 | 11.460 | 0.245 | | |

Proliferation: N = 2 experiments per cell line (except H226 and H1975 are n = 1 currently)
binding = RU max,
stability = RU max post-injection
*SPR RU data obtained under different conditions on each date.
<sup>a</sup>blank cell means not evaluated that day.

What is claimed is:

1. A compound of Formula IIA:

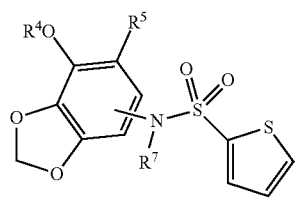

Formula IIA wherein $R^4$ is —H, —$C_1$-$C_4$alkyl, $R^5$ is —$C_1$-$C_4$alkyl-OH, —$C_2$-$C_6$alkenyl-OH, $C_1$-$C_4$alkykl-C(O)—$C_1$-$C_4$alkyl, —$C_2$-$C_6$alkenyl-C(O)—$C_1$-$C_4$alkyl, —$C_1$-$C_4$alkykl-C(O)—$C_3$-$C_5$cycloalkyl, —$C_2$-$C_6$alkenyl-C(O)—$C_3$-$C_5$cycloalkyl,

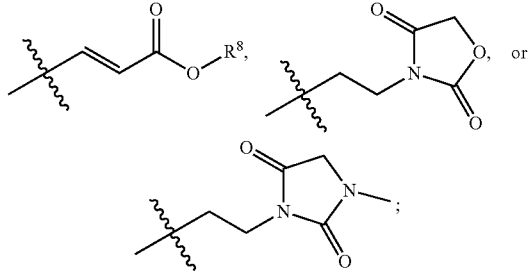

$R^8$ is $C_1$-$C_4$alkyl, or —$C_3$-$C_5$ cycloalkyl;

$R^7$ is H or

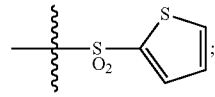

or a pharmaceutically acceptable salt thereof.

2. The compound of claim 1, wherein $R^4$ is methyl.

3. The compound of claim 1, wherein $R^7$ is

[structure: -SO₂-thiophene]

4. The compound of claim 1, wherein $R^5$ is —$C_2$-$C_6$alkenyl-OH, or —$C_2$ $C_6$alkenyl-C(O)—$C_1$-$C_4$alkyl.

5. The compound of claim 1, wherein $R^5$ is

[structure: allylic ester with $R^8$]

6. The compound of claim 5, wherein $R^8$ is cyclopropyl or cyclobutyl.

7. The compound of claim 1, wherein $R^7$ is H.

8. The compound of claim 1, wherein $R^5$ is

[structure: alkyl-oxazolidinedione]

9. The compound of claim 1, wherein $R^5$ is

[structure: alkyl-methylhydantoin]

10. The compound of claim 1, selected from:

[structures 83–89 depicting various substituted benzodioxole-thiophenesulfonamide compounds]

145
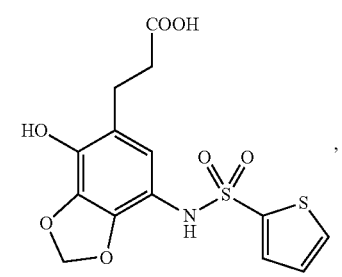
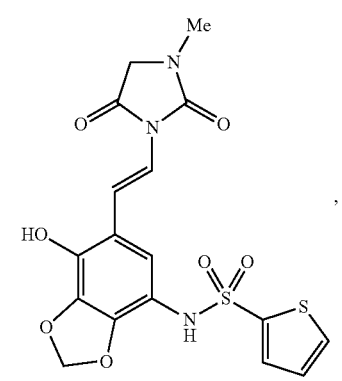
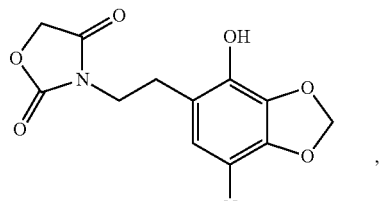
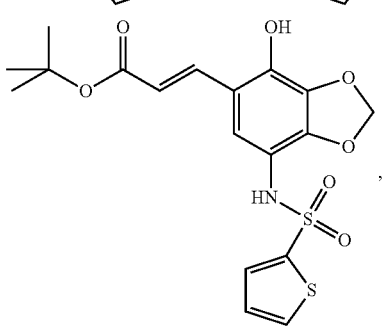
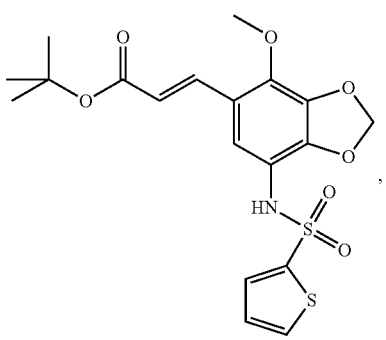
146
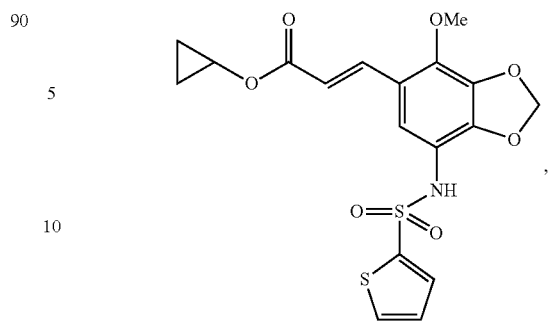
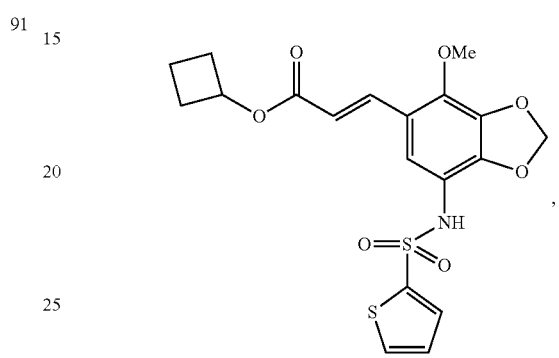
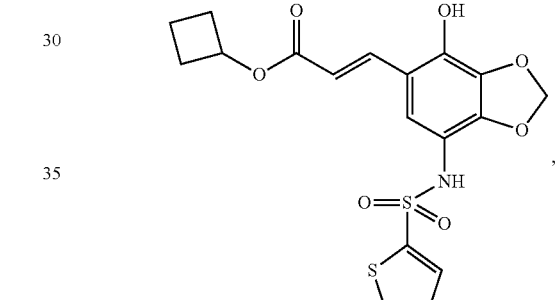
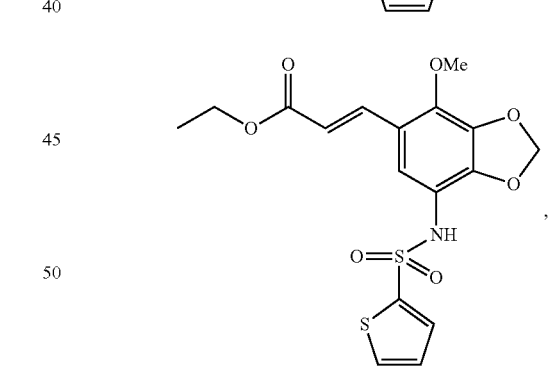
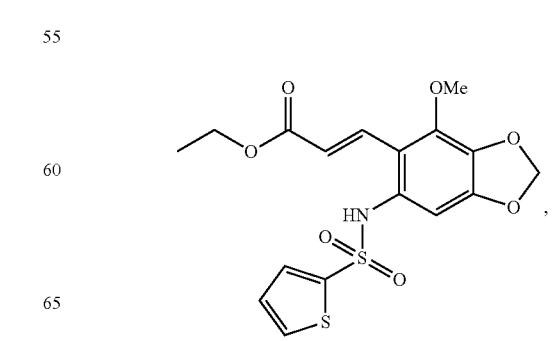

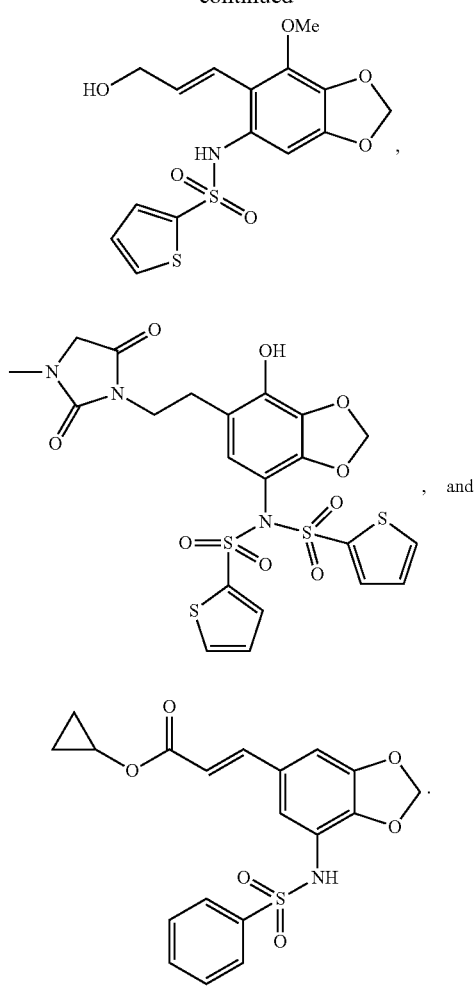

, and

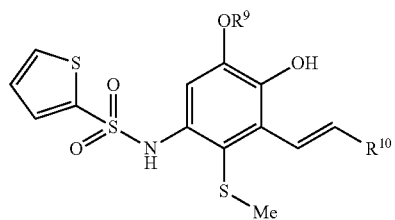

.

11. A compound of Formula IIIA:

Formula IIIA

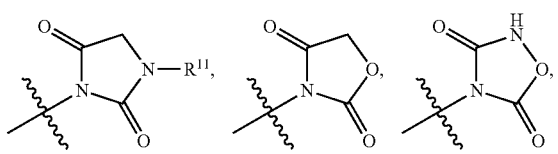

wherein

R⁹ is —H or —C₁-C₄alkyl;

R¹⁰ is —C(O)O C₁-C₄alkyl, —C(O)OH,

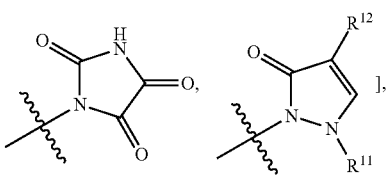,

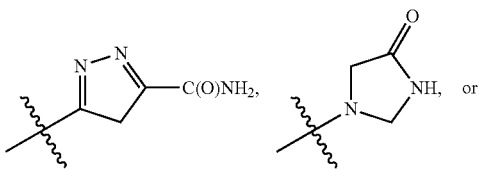

R¹¹ is H or C₁-C₄alkyl;

R¹² is C₁-C₄alkyl;

or a pharmaceutically acceptable salt thereof.

12. The compound of claim 11, wherein R⁹ is methyl.

13. The compound of claim 11, wherein R¹⁰ is —C(O)O C₁-C₄alkyl.

14. The compound of claim 13, wherein the C₁-C₄ alkyl is ethyl.

15. The compound of claim 11, wherein R¹⁰ is

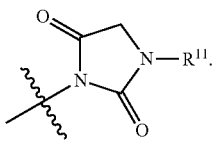.

16. The compound of claim 11, wherein R¹⁰ is

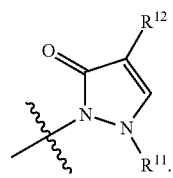.

17. The compound of claim 11, wherein R¹⁰ is

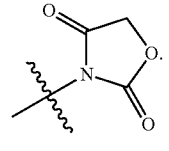 [SMILES: *N1C(=O)COC1=O].

18. The compound of claim 11 selected from:
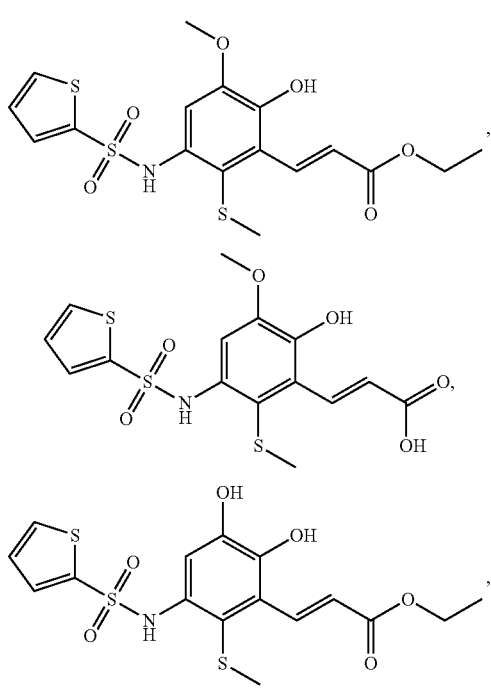
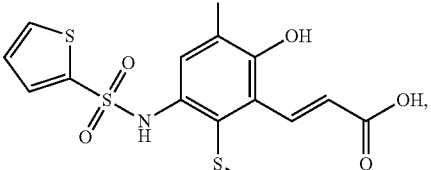
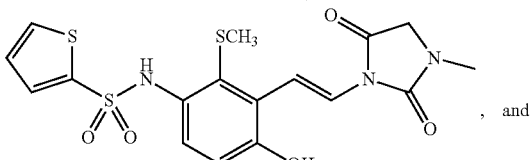
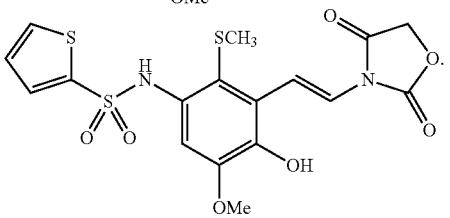
19. The compound of claim 1, wherein $R^5$ is —$C_1$-$C_4$alkyl-OH, or —$C_1$-$C_4$alkyl-C(O)—$C_1$-$C_4$alkyl.
* * * * *